US012600992B2

(12) United States Patent (10) Patent No.: US 12,600,992 B2

Jin et al. (45) Date of Patent: Apr. 14, 2026

(54) 2,3-BUTANEDIOL PRODUCTION, METHYL ETHYL KETONE PRODUCTION, AND INDUCTION OF DROUGHT TOLERANCE IN PLANTS

(71) Applicant: The Board of Trustees of the University of Illinois, Urbana, IL (US)

(72) Inventors: Yong-Su Jin, Champaign, IL (US); Jae Won Lee, Champaign, IL (US); Young B. Cho, Savoy, IL (US); Ye-Gi Lee, Savoy, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 482 days.

(21) Appl. No.: 18/347,473

(22) Filed: Jul. 5, 2023

(65) Prior Publication Data

US 2024/0011056 A1 Jan. 11, 2024

Related U.S. Application Data

(60) Provisional application No. 63/358,527, filed on Jul. 6, 2022.

(51) Int. Cl.
| | |
|---|---|
| *C12P 7/04* | (2006.01) |
| *A01N 63/32* | (2020.01) |
| *A01P 21/00* | (2006.01) |
| *C12N 9/02* | (2006.01) |
| *C12N 9/04* | (2006.01) |
| *C12N 9/12* | (2006.01) |
| *C12N 9/16* | (2006.01) |
| *C12N 9/88* | (2006.01) |

(52) U.S. Cl.
CPC .............. *C12P 7/04* (2013.01); *A01N 63/32* (2020.01); *A01P 21/00* (2021.08); *C12N 9/0006* (2013.01); *C12N 9/0008* (2013.01); *C12N 9/1205* (2013.01); *C12N 9/16* (2013.01); *C12N 9/88* (2013.01); *C12Y 101/01001* (2013.01); *C12Y 101/01009* (2013.01); *C12Y 101/01037* (2013.01); *C12Y 207/01017* (2013.01); *C12Y 401/01001* (2013.01)

(58) Field of Classification Search
CPC ....................................................... C12P 7/04
See application file for complete search history.

(56) References Cited

U.S. PATENT DOCUMENTS

| | | |
|---|---|---|
| 9,328,358 B2 | 5/2016 | Ho et al. |
| 10,982,236 B2 | 4/2021 | Ho et al. |
| 2005/0003500 A1 | 1/2005 | Masatake et al. |

FOREIGN PATENT DOCUMENTS

| | | |
|---|---|---|
| EP | 2783007 B1 | 8/2017 |
| ES | 2776361 T3 | 7/2020 |

OTHER PUBLICATIONS

Adom et al., "Life-Cycle Fossil Energy Consumption and Greenhouse Gas Emissions of Bioderived Chemicals and Their Conventional Counterparts", Environ. Sci. Technol., Dec. 16, 2014, 48(24): 14624-14631.

Ansell et al., "The two isoenzymes for yeast NAD+-dependent glycerol 3-phosphate dehydrogenase encoded by GPD1 and GPD2 have distinct roles in osmoadaptation and redox regulation", EMBO J., May 1, 1997, 16(9): 2179-2187.

Araus et al., "Breeding for Yield Potential and Stress Adaptation in Cereals", CRC Crit Rev Plant Sci., 2008, 27(6): 377-412.

Argonne National Laboratory, "Life-cycle Analysis of Bioproducts and Their Conventional Counterparts in GREET", Technical Report No. ANL/ESD-14/9 Rev.; 121327, Sep. 1, 2015.

Argonne National Laboratory, "Summary of Expansions and Updates in GREET 2020", Technical Report No. ANL/ESD-20/9; 163298, Oct. 1, 2020.

Bhagwat et al., "Sustainable Production of Acrylic Acid via 3-Hydroxypropionic Acid from Lignocellulosic Biomass", ACS Sustainable Chem., Nov. 29, 2021, 9(49): 16659-16669.

BioSTEAM Development Group, "BioSTEAM: The Biorefinery Simulation and Techno-Economic Analysis Modules", Accessed Apr. 17, 2020 from: https://github.com/BioSTEAMDevelopmentGroup/biosteam.

BioSTEAM Development Group, Bioindustrial-Park: BioSTEAM's Premier Repository for Biorefinery Models and Results. Accessed Apr. 17, 2020 from: https://github.com/BioSTEAMDevelopmentGroup/Bioindustrial-Park.

Celinska et al., "Biotechnological production of 2,3-butanediol-Current state and prospects", Biotechnol. Adv., Nov./Dec. 2009, 27(6): 715-725.

Cho et al., "2R,3R-Butanediol, a Bacterial Volatile Produced by Pseudomonas chlororaphis O6, Is Involved in Induction of Systemic Tolerance to Drought in *Arabidopsis thaliana*", Mol. Plant Microbe Interact., Aug. 2008, 21(8): 1067-1075.

Comas et al., "Root traits contributing to plant productivity under drought", Front. Plant Sci., Nov. 5, 2013, 4: 442.

Cortes-Pena et al., "BioSTEAM: A Fast and Flexible Platform for the Design, Simulation, and Techno-Economic Analysis of Biorefineries under Uncertainty", ACS Sustain. Chem. & Eng., Jan. 30, 2020, 8(8): 3302-3310.

(Continued)

*Primary Examiner* — Suzanne M Noakes

(74) *Attorney, Agent, or Firm* — Lathrop GPM LLP; Lisa Hillman

(57) ABSTRACT

Provided herein are compositions and methods for the fermentative production of 2,3-butanediol (2,3-BDO), compositions and methods for making methyl ethyl ketone (MEK), and methods of inducing drought tolerance in plants.

20 Claims, 13 Drawing Sheets

Figure 1:
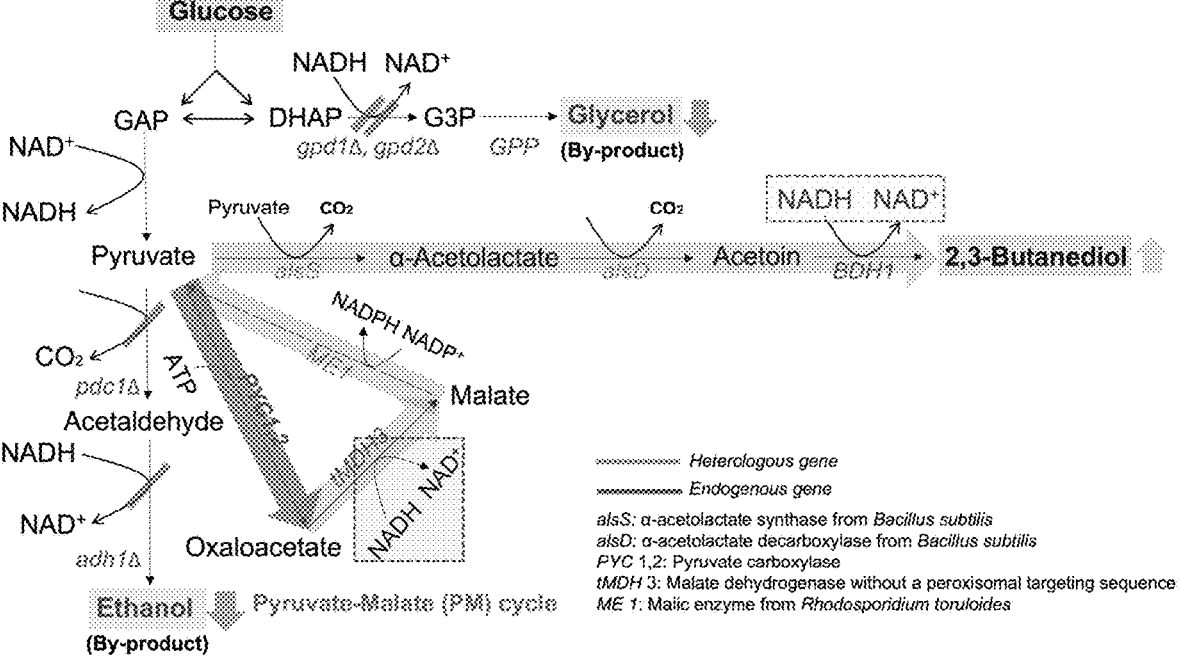

Specification includes a Sequence Listing.

(56) References Cited

OTHER PUBLICATIONS

Davis et al., "Process Design and Economics for the Conversion of Lignocellulosic Biomass to Hydrocarbon Fuels and Coproducts: 2018 Biochemical Design Case Update; Biochemical Deconstruction and Conversion of Biomass to Fuels and Products via Integrated Biorefinery Pathways"; Technical Report No. NREL/TP-5100-71949, Nov. 19, 2018.
De Deken, "The Crabtree effect: a regulatory system in yeast", J. Gen. Microbiol., Aug. 1966, 44(2): 149-156.
De Smidt et al., "Molecular and physiological aspects of alcohol dehydrogenases in the ethanol metabolism of Saccharomyces cerevisiae", FEMS Yeast Res., Feb. 2012, 12(1): 33-47.
Emerson et al., "Kinetics of dehydration of aqueous 2,3-butanediol to methyl ethyl ketone", Ind. Eng. Chem. Res., Sep. 1, 1982, 21(3): 473-477.
Farooq et al., "Drought Stress in Plants: An Overview", Plant Responses to Drought Stress: From Morphological to Molecular Features, Oct. 2012, pp. 1-33.
Flikweert, "Pyruvate decarboxylase: An indispensable enzyme for growth of Saccharomyces cerevisiae on glucose", Yeast, Mar. 15, 1996, 12(3): 247-257.
Gietz et al., "High-efficiency yeast transformation using the LiAc/SS carrier DNA/PEG method", Nat. Protoc., Jan. 31, 2007, 2(1): 31-34.
Grand View Research, Methyl Ethyl Ketone Market Size, Share & Trends Analysis Report by Application (Paints & Coatings, Printing Inks, Adhesive), by Region (North America, Europe, APAC, MEA, CSA), and Segment Forecasts, 2016-2024, Report ID: 978-1-68038-209-9, 2016, Accessed Dec. 7, 2021 from: https://www.grandviewresearch.com/industry-analysis/methyl-ethyl-ketone-mek- market.
Hahm et al., "Biological control and plant growth promoting capacity of rhizobacteria on pepper under greenhouse and field conditions", J. Microbiol., Jun. 2012, 50(3): 380-385.
Hakizimana et al., "The current strategies and parameters for the enhanced microbial production of 2,3-butanediol", Biotechnol Rep (Amst)., Nov. 13, 2019, 25:e00397.
Han et al., "GacS-dependent production of 2R, 3R-butanediol by Pseudomonas chlororaphis O6 is a major determinant for eliciting systemic resistance against Erwinia carotovora but not against Pseudomonas syringae pv. tabaci in tobacco", Mol Plant Microbe Interact., Aug. 2006, 19(8): 924-930.
Harvianto et al., "Purification of 2,3-butanediol from fermentation broth: process development and techno-economic analysis", Biotechnol. Biofuels, Jan. 25, 2018, 11(1): 18.
Hoppe, et al., "Tailor-made fuels for future engine concepts", Int. J. Engine Res., Sep. 7, 2015, 17(1): 16-27.
Idaho National Laboratory, "Herbaceous Feedstock 2018 State of Technology Report", Milestone Completion Report, No. INL/EXT-18-51654-Rev000, Sep. 30, 2018.
Ishida et al., "The Effect of Pyruvate Decarboxylase Gene Knockout in Saccharomyces cerevisiae on L-Lactic Acid Production", Biosci. Biotechnol. Biochem., May 2006, 70(5): 1148-1153.
Ishii et al., "A pyruvate carbon flux tugging strategy for increasing 2,3-butanediol production and reducing ethanol subgeneration in the yeast Saccharomyces cerevisiae", Biotechnol. Biofuels, Jun. 26, 2018, 11(1): 180.
Ji et al., "Microbial 2,3-butanediol production: A state-of-the-art review", Biotechnol. Adv., May/Jun. 2011, 29(3): 351-364.
Kaliyan et al., "Economic and Environmental Analysis for Corn Stover and Switchgrass Supply Logistics", Bioenergy Res., Mar. 31, 2015, 8(3): 1433-1448.
Kim et al., "Efficient production of 2,3-butanediol in Saccharomyces cerevisiae by eliminating ethanol and glycerol production and redox rebalancing", Metab. Eng., Sep. 2015, 31: 94-101.
Kim et al., "Production of 2,3-butanediol by engineered Saccharomyces cerevisiae", Bioresour. Technol., Oct. 2013, 146: 274-281.

Kim et al., "Production of 2,3-butanediol from xylose by engineered Saccharomyces cerevisiae", J. Biotechnol., Dec. 20, 2014, 192(Pt. B): 376-382.
Kim, et al., "Deletion of glycerol-3-phosphate dehydrogenase genes improved 2,3- butanediol production by reducing glycerol production in pyruvate decarboxylase-deficient Saccharomyces cerevisiae", J. Biotechnol., Oct. 10, 2019, 304: 31-37.
Kim, et al., "Enhanced production of 2,3-butanediol by engineered Saccharomyces cerevisiae through fine-tuning of pyruvate decarboxylase and NADH oxidase activities", Biotechnol. Biofuels, Dec. 9, 2016, 9: 265.
Kim, et al., "Expression of Lactococcus lactis NADH oxidase increases 2,3-butanediol production in Pdc-deficient Saccharomyces cerevisiae", Bioresour. Technol., Sep. 2015, 191: 512-519.
Kong et al., "Stereoisomers of the Bacterial Volatile Compound 2,3-Butanediol Differently Elicit Systemic Defense Responses of Pepper against Multiple Viruses in the Field, Front". Plant Sci., Feb. 22, 2018, 9: 90.
Kruyer et al., "Designing the bioproduction of Martian rocket propellant via a biotechnology-enabled in situ resource utilization strategy", Nat. Commun., Oct. 25, 2021, 12(1): 6166.
Kwak et al., "Enhanced isoprenoid production from xylose by engineered Saccharomyces cerevisiae", Biotechnol. Bioeng., Nov. 2017, 114(11): 2581-2591.
Lee et al., "Enhanced 2'-Fucosyllactose production by engineered Saccharomyces cerevisiae using xylose as a co-substrate", Metab. Eng., Nov. 2020, 62: 322-329.
Lee, et al., "Metabolic engineering of non-pathogenic microorganisms for 2,3-butanediol production", Appl. Microbiol. Biotechnol., Jul. 21, 2021, 105(14-15): 5751-5767.
Lee, et al., "Production of 2,3-butanediol from glucose and cassava hydrolysates by metabolically engineered industrial polyploid Saccharomyces cerevisiae", Biotechnol. Biofuels, Aug. 29, 2019, 12(1): 204.
Li et al., "Sustainable Lactic Acid Production from Lignocellulosic Biomass, ACS Sustain". Chem. Eng., Jan. 12, 2021, 9(3): 1341-1351.
Lian et al., "Metabolic engineering of a Saccharomyces cerevisiae strain capable of simultaneously utilizing glucose and galactose to produce enantiopure (2R,3R)-butanediol", Metab Eng., May 23, 2014, 23: 92-99, Published Feb. 10, 2014.
Lian et al., "Recent advances in metabolic engineering of Saccharomyces cerevisiae: new tools and their applications", Metab. Eng., Nov. 2018, 50: 85-108. Epub Apr. 25, 2018.
Liu et al., "Development and Commercial Application of Methyl-ethyl-ketone Production Technology", Chin. J. Chem. Eng., Oct. 2006, 14(5): 676-684.
Maina et al., "Bioprocess Development for 2,3-Butanediol Production from Crude Glycerol and Conceptual Process Design for Aqueous Conversion into Methyl Ethyl Ketone", ACS Sustain. Chem. Eng., Jun. 21, 2021, 9(26): 8692-8705.
Menéndez et al., "Regulatory regions in the promoters of the Saccharomyces cerevisiae PYC1 and PYC2 genes encoding isoenzymes of pyruvate carboxylase", FEMS Microbiol. Lett., Jul. 15, 1998, 164(2): 345-352.
Multer et al., "Production of Methyl Ethyl Ketone from Biomass Using a Hybrid Biochemical/Catalytic Approach", Ind. Eng. Chem. Res., Aug. 31, 2012, 52(1): 56-60.
Mumberg et al., "Yeast vectors for the controlled expression of heterologous proteins in different genetic backgrounds", Gene, Apr. 14, 1995, 156(1): 119-122.
Murashige et al., "Revised Medium for Rapid Growth and Bio Assays with Tobacco Tissue Cultures", Physiol. Plant., Jul. 1962, 15(3): 473-497.
National Renewable Energy Lab (NREL), "Lignocellulosic Biomass to Ethanol Process Design and Economics Utilizing Co-Current Dilute Acid Prehydrolysis and Enzymatic Hydrolysis for Corn Stover", Technical Report No. NREL/TP-510-32438, Jun. 2002. Accessed from: https://www.nrel.gov/docs/fy02osti/32438.pdf.
National Renewable Energy Lab (NREL), "Process Design and Economics for Biochemical Conversion of Lignocellulosic Biomass

(56)          References Cited

OTHER PUBLICATIONS to Ethanol: Dilute-Acid Pretreatment and Enzymatic Hydrolysis of Corn Stover" NREL/TP-5100-47764, May 2011 Accessed from: https://www.nrel.gov/docs/fy11osti/47764.pdf.

Ng et al., "Production of 2,3-butanediol in *Saccharomyces cerevisiae* by in silico aided metabolic engineering", Microb Cell Fact., May 28, 2012, 11: 68.

Peng et al., "Controlling heterologous gene expression in yeast cell factories on different carbon substrates and across the diauxic shift: a comparison of yeast promoter activities", Microb. Cell Fact., Jun. 26, 2015, 14: 91.

Penner, "Conceptual Design of Methyl Ethyl Ketone Production via 2,3-Butanediol for Fuels and Chemicals", Ind. Eng. Chem. Res., Mar. 2, 2017, 56(14): 3947-3957.

Pronk et al., "Pyruvate Metabolism in *Saccharomyces cerevisiae*", Yeast, Dec. 1996, 12(16): 1607-1633.

Shi et al., "Butanediol-enhanced heat tolerance in Agrostis stolonifera in association with alteration in stress-related gene expression and metabolic profiles", Environ. Exp. Bot., Sep. 2018, 153: 209-217.

Shi et al., "Transcriptional Responses of Creeping Bentgrass to 2,3-Butanediol, a Bacterial Volatile Compound (BVC) Analogue", Molecules, Aug. 16. 2017, 22(8): 1318.

Silva Dias et al., "C4 Bacterial Volatiles Improve Plant Health", Pathogens, May 31, 2021, 10(6): 682.

Skory, "Isolation and Expression of Lactate Dehydrogenase Genes from *Rhizopus oryzae*", Appl. Environ. Microbiol., Jun. 2000, 66(6): 2343-2348.

Syu, "Biological production of 2,3-butanediol", Appl. Microbiol. Biotechnol., Jan. 2001, 55(1): 10-18.

Torres-Vinces et al., "Methyl Ethyl Ketone Production through an Intensified Process", Chem. Eng. Technol., Mar. 30, 2020, 43(7): 1433-1441.

Tsai et al., "Rapid and marker-free refactoring of xylose-fermenting yeast strains with Cas9/CRISPR", Biotechnol. Bioeng., Nov. 2015, 112(11): 2406-2411.

Turner et al., "Lactic acid production from cellobiose and xylose by engineered *Saccharomyces cerevisiae*", Biotechnol. Bioeng., May 2016, 113(5): 1075-1083.

U.S. Bureau of Labor Statistics, "Producer Price Index by Commodity: Chemicals and Allied Products: Sulfuric Acid (WPU0613020T1)", Federal Reserve Bank of St. Louis, 2020. Accessed from: https://alfred.stlouisfed.org/series?seid=WPU0613020T1.

U.S. Energy Information Administration, "Annual Energy Outlook 2019: with projections to 2050", Jan. 24, 2019, Accessed May 22, 2019, from: https://www.eia.gov/outlooks/aeo/.

U.S. EPA, "Lifecycle Analysis of Greenhouse Gas Emissions under the Renewable Fuel Standard", last updated Nov. 27, 2023, Accessed May 2, 2021, from: https://www.epa.gov/renewable-fuel-standard-program/lifecycle-analysis-greenhouse-gas-emissions-under-renewable-fuel.

U.S. Geological Survey, "Mineral Commodity Summaries 2020", U.S. Geological Survey, 2020, 200 p.

Wernet et al., "The ecoinvent database version 3 (part I): overview and methodology", Int. J. Life Cycle Assess., Apr. 21, 2016, 21(9): 1218-1230.

Wu et al., "Acetoin and 2,3-butanediol from Bacillus amyloliquefaciens induce stomatal closure in *Arabidopsis thaliana* and Nicotiana benthamiana", J. Exp. Bot., Nov. 26, 2018, 69(22): 5625-5635.

Yu, et al., "Reprogramming Yeast Metabolism from Alcoholic Fermentation to Lipogenesis", Cell, Sep. 6, 2018, 174(6): 1549-1558.e14.

Zelle et al., "Malic Acid Production by *Saccharomyces cerevisiae*: Engineering of Pyruvate Carboxylation, Oxaloacetate Reduction, and Malate Export", Appl. Environ. Microbiol., May 2008, 74(9): 2766-2777.

Zeng et al., "Microbial production of diols as platform chemicals: Recent progresses", Curr. Opin. Biotechnol., Dec. 2011, 22(6): 749-757.

Zhang et al., "Construction of a quadruple auxotrophic mutant of an industrial polyploid *Saccharomyces cerevisiae* strain by using RNA-guided Cas9 nuclease", Appl. Environ. Microbiol., Dec. 2014, 80(24): 7694-7701.

Zhang et al., "Production of C2—C4 diols from renewable bioresources: new metabolic pathways and metabolic engineering strategies", Biotechnol. Biofuels, Dec. 13, 2017, 10(1): 299.

Zhao et al., "Catalytic dehydration of 2,3-butanediol over P/HZSM-5: effect of catalyst, reaction temperature and reactant configuration on rearrangement products", RSC Adv., Jan. 26, 2016, 6(21): 16988-16995.

Zhou et al., "Hydrogenation of aldehydes catalyzed by kieselguhr-supported carboxymethylcellulose-nickel complex", Polym. Adv. Technol., Apr. 2, 2004, 15(4): 218-220.

*Feedstock (corn stover) farming, harvesting, transportation, storage, handling, and pre-processing. Credit for fixed carbon is not depicted as this is equal to the sum of direct biogenic emissions and end-of-life acrylic acid degradation (assumed to be entirely $CO_2$).

(a)

Pdc deficient (Pdc⁻) strain

(b)

Pdc1 and Adh1 deleted strain

SEQUENCE LISTING

```
Sequence total quantity: 79
SEQ ID NO: 1              moltype = DNA  length = 24
FEATURE                  Location/Qualifiers
source                   1..24
                         mol_type = other DNA
                         organism = synthetic construct
SEQUENCE: 1
gctgcaggaa ttcgatatca agct                                        24

SEQ ID NO: 2              moltype = DNA  length = 24
FEATURE                  Location/Qualifiers
source                   1..24
                         mol_type = other DNA
                         organism = synthetic construct
SEQUENCE: 2
ccgggggatc cactagttct agaa                                        24
```

```
SEQ ID NO: 3            moltype = DNA   length = 74
FEATURE                 Location/Qualifiers
source                  1..74
                        mol_type = other DNA
                        organism = synthetic construct
SEQUENCE: 3
aaacaccaga acttagtttc gacggattct agaactagtg gatcccccgg atggtcaaag  60
tcgcaattct tggc                                                     74

SEQ ID NO: 4            moltype = DNA   length = 77
FEATURE                 Location/Qualifiers
source                  1..77
                        mol_type = other DNA
                        organism = synthetic construct
SEQUENCE: 4
atgactcgag gtcgacggta tcgataagct tgatatcgaa ttcctgcagc ttaagagtct  60
aggatgaaac tcttgcc                                                  77

SEQ ID NO: 5            moltype = DNA   length = 36
FEATURE                 Location/Qualifiers
source                  1..36
                        mol_type = other DNA
                        organism = synthetic construct
SEQUENCE: 5
cccgagctct ctttgaaaag ataatgtatg attatg                             36

SEQ ID NO: 6            moltype = DNA   length = 38
FEATURE                 Location/Qualifiers
source                  1..38
                        mol_type = other DNA
                        organism = synthetic construct
SEQUENCE: 6
aactgcaggg atccagacat aaaaaacaaa aaaagcac                           38

SEQ ID NO: 7            moltype = DNA   length = 60
FEATURE                 Location/Qualifiers
source                  1..60
                        mol_type = other DNA
                        organism = synthetic construct
SEQUENCE: 7
tcataacctc acgcaaaata acacagtcaa atcaatcaaa atggtattac actcaaaggt  60

SEQ ID NO: 8            moltype = DNA   length = 60
FEATURE                 Location/Qualifiers
source                  1..60
                        mol_type = other DNA
                        organism = synthetic construct
SEQUENCE: 8
tgcttataaa actttaacta ataattagag attaaatcgc tcctcaacag ctacttttag  60

SEQ ID NO: 9            moltype = DNA   length = 25
FEATURE                 Location/Qualifiers
source                  1..25
                        mol_type = other DNA
                        organism = synthetic construct
SEQUENCE: 9
ctgcacaata tttcaagcta tacca                                         25

SEQ ID NO: 10           moltype = DNA   length = 28
FEATURE                 Location/Qualifiers
source                  1..28
                        mol_type = other DNA
                        organism = synthetic construct
SEQUENCE: 10
cataagaaat tcgcttattt agaagtgt                                      28

SEQ ID NO: 11           moltype = DNA   length = 60
FEATURE                 Location/Qualifiers
source                  1..60
                        mol_type = other DNA
                        organism = synthetic construct
SEQUENCE: 11
gccaaggaaa taaagcaaat aacaataaca ccattatttt gcataacctt gaaggttaac  60

SEQ ID NO: 12           moltype = DNA   length = 60
FEATURE                 Location/Qualifiers
source                  1..60
                        mol_type = other DNA
                        organism = synthetic construct
```

-continued

```
SEQUENCE: 12
tcaatctttc aaataaatat ttacctaagg ttatttcaga catgccgaat agttcacttg  60

SEQ ID NO: 13              moltype = DNA   length = 60
FEATURE                    Location/Qualifiers
source                     1..60
                           mol_type = other DNA
                           organism = synthetic construct
SEQUENCE: 13
aacctcgagg agaagttttt ttacccctct ccacagatcc aggaaacagc tatgaccatg  60

SEQ ID NO: 14              moltype = DNA   length = 60
FEATURE                    Location/Qualifiers
source                     1..60
                           mol_type = other DNA
                           organism = synthetic construct
SEQUENCE: 14
taattaggta gaccgggtag atttttccgt aaccttggtg tctgtaaaac gacggccagt  60

SEQ ID NO: 15              moltype = DNA   length = 71
FEATURE                    Location/Qualifiers
source                     1..71
                           mol_type = other DNA
                           organism = synthetic construct
SEQUENCE: 15
caaaattacc tacggtaatt agtgaaaggc caaaatctaa tgttacaata aattaaccct  60
cactaaaggg a                                                        71

SEQ ID NO: 16              moltype = DNA   length = 72
FEATURE                    Location/Qualifiers
source                     1..72
                           mol_type = other DNA
                           organism = synthetic construct
SEQUENCE: 16
gaccgttccc ttgtgttgta ccagtggtag ggttcttctc ggtagcttct gtaatacgac  60
tcactatagg gc                                                       72

SEQ ID NO: 17              moltype = DNA   length = 25
FEATURE                    Location/Qualifiers
source                     1..25
                           mol_type = other DNA
                           organism = synthetic construct
SEQUENCE: 17
ttaattttct tttatcttac tctcc                                         25

SEQ ID NO: 18              moltype = DNA   length = 24
FEATURE                    Location/Qualifiers
source                     1..24
                           mol_type = other DNA
                           organism = synthetic construct
SEQUENCE: 18
tagttatgag aaatgacata atgc                                          24

SEQ ID NO: 19              moltype = DNA   length = 22
FEATURE                    Location/Qualifiers
source                     1..22
                           mol_type = other DNA
                           organism = synthetic construct
SEQUENCE: 19
cgctcccctt ccttatcaat gc                                            22

SEQ ID NO: 20              moltype = DNA   length = 22
FEATURE                    Location/Qualifiers
source                     1..22
                           mol_type = other DNA
                           organism = synthetic construct
SEQUENCE: 20
ggagagtgtc tattcgtcat cg                                            22

SEQ ID NO: 21              moltype = DNA   length = 71
FEATURE                    Location/Qualifiers
source                     1..71
                           mol_type = other DNA
                           organism = synthetic construct
SEQUENCE: 21
aggattcatt agtggaaaag ttcagtgaca aaatctagaa aataaatatga aattaaccct  60
cactaaaggg a                                                        71

SEQ ID NO: 22              moltype = DNA   length = 72
```

-continued

```
FEATURE                    Location/Qualifiers
source                     1..72
                           mol_type = other DNA
                           organism = synthetic construct
SEQUENCE: 22
gaatatagcg tattttatt taatcacggt acaatggaga tatttgcatg gtaatacgac    60
tcactatagg gc                                                       72

SEQ ID NO: 23              moltype = DNA   length = 80
FEATURE                    Location/Qualifiers
source                     1..80
                           mol_type = other DNA
                           organism = synthetic construct
SEQUENCE: 23
tctcaattat tattttctac tcataacctc acgcaaaata acacagtcaa atcaatcaaa    60
atgccagcac attttgcccc                                                80

SEQ ID NO: 24              moltype = DNA   length = 80
FEATURE                    Location/Qualifiers
source                     1..80
                           mol_type = other DNA
                           organism = synthetic construct
SEQUENCE: 24
tatttttcgt tacataaaaa tgcttataaa actttaacta ataattagag attaaatcgc    60
ctactgtgcc tgctgttccg                                                80

SEQ ID NO: 25              moltype = DNA   length = 60
FEATURE                    Location/Qualifiers
source                     1..60
                           mol_type = other DNA
                           organism = synthetic construct
SEQUENCE: 25
ccgtacttgc agcccgttgc caattgccgc ctaatattgt catagcttca aaatgtttct    60

SEQ ID NO: 26              moltype = DNA   length = 60
FEATURE                    Location/Qualifiers
source                     1..60
                           mol_type = other DNA
                           organism = synthetic construct
SEQUENCE: 26
tgaagttatc tctcaagccg gcgaattttc tttgcgacat cttagattag attgctatgc    60

SEQ ID NO: 27              moltype = DNA   length = 60
FEATURE                    Location/Qualifiers
source                     1..60
                           mol_type = other DNA
                           organism = synthetic construct
SEQUENCE: 27
cctcaaacaa gaattgtacg acattacgtt caagaaaatt aagaaattac cgtcgctcgt    60

SEQ ID NO: 28              moltype = DNA   length = 60
FEATURE                    Location/Qualifiers
source                     1..60
                           mol_type = other DNA
                           organism = synthetic construct
SEQUENCE: 28
aattgtccct aagaccggcc aatttcttgc tactgctcat agacattgtt ttatatttgt    60

SEQ ID NO: 29              moltype = DNA   length = 25
FEATURE                    Location/Qualifiers
source                     1..25
                           mol_type = other DNA
                           organism = synthetic construct
SEQUENCE: 29
ttcataattg cataatattg tccgc                                          25

SEQ ID NO: 30              moltype = DNA   length = 23
FEATURE                    Location/Qualifiers
source                     1..23
                           mol_type = other DNA
                           organism = synthetic construct
SEQUENCE: 30
ttgcaatgtg tgtcaagata tcg                                            23

SEQ ID NO: 31              moltype = DNA   length = 23
FEATURE                    Location/Qualifiers
source                     1..23
                           mol_type = other DNA
                           organism = synthetic construct
```

-continued

```
SEQUENCE: 31
ttacactgcc tcattgatgg tgg                                             23

SEQ ID NO: 32           moltype = DNA   length = 24
FEATURE                 Location/Qualifiers
source                  1..24
                        mol_type = other DNA
                        organism = synthetic construct
SEQUENCE: 32
tacaattggg tgaaatgggg agcg                                            24

SEQ ID NO: 33           moltype = DNA   length = 25
FEATURE                 Location/Qualifiers
source                  1..25
                        mol_type = other DNA
                        organism = synthetic construct
SEQUENCE: 33
ggtgagaatc cttctgatgc atact                                           25

SEQ ID NO: 34           moltype = DNA   length = 25
FEATURE                 Location/Qualifiers
source                  1..25
                        mol_type = other DNA
                        organism = synthetic construct
SEQUENCE: 34
gtgctctact ggtgattttt catcg                                           25

SEQ ID NO: 35           moltype = DNA   length = 18
FEATURE                 Location/Qualifiers
source                  1..18
                        mol_type = other DNA
                        organism = synthetic construct
SEQUENCE: 35
gtctgccgaa attctgtg                                                   18

SEQ ID NO: 36           moltype = DNA   length = 18
FEATURE                 Location/Qualifiers
source                  1..18
                        mol_type = other DNA
                        organism = synthetic construct
SEQUENCE: 36
cggtcagaaa gggaaatg                                                   18

SEQ ID NO: 37           moltype = DNA   length = 18
FEATURE                 Location/Qualifiers
source                  1..18
                        mol_type = other DNA
                        organism = synthetic construct
SEQUENCE: 37
agtggaacat agaagggg                                                   18

SEQ ID NO: 38           moltype = DNA   length = 17
FEATURE                 Location/Qualifiers
source                  1..17
                        mol_type = other DNA
                        organism = synthetic construct
SEQUENCE: 38
taagcagccc agtgaac                                                    17

SEQ ID NO: 39           moltype = DNA   length = 22
FEATURE                 Location/Qualifiers
source                  1..22
                        mol_type = other DNA
                        organism = synthetic construct
SEQUENCE: 39
cctactgtcc ctatgtctct gg                                              22

SEQ ID NO: 40           moltype = DNA   length = 22
FEATURE                 Location/Qualifiers
source                  1..22
                        mol_type = other DNA
                        organism = synthetic construct
SEQUENCE: 40
ccaaagtaca tccttgtcga gc                                              22

SEQ ID NO: 41           moltype = DNA   length = 30
FEATURE                 Location/Qualifiers
source                  1..30
                        mol_type = other DNA
```

```
                             organism = synthetic construct
SEQUENCE: 41
aagagtgttt agcttacgga cctattgcca                                        30

SEQ ID NO: 42               moltype = DNA   length = 30
FEATURE                     Location/Qualifiers
source                      1..30
                            mol_type = other DNA
                            organism = synthetic construct
SEQUENCE: 42
cagtagtgac taacatagcg ctcttatctc                                        30

SEQ ID NO: 43               moltype = DNA   length = 18
FEATURE                     Location/Qualifiers
source                      1..18
                            mol_type = other DNA
                            organism = synthetic construct
SEQUENCE: 43
tggtaatgag gaatgcgt                                                     18

SEQ ID NO: 44               moltype = DNA   length = 18
FEATURE                     Location/Qualifiers
source                      1..18
                            mol_type = other DNA
                            organism = synthetic construct
SEQUENCE: 44
cgggcattat gcgtagat                                                     18

SEQ ID NO: 45               moltype = DNA   length = 25
FEATURE                     Location/Qualifiers
source                      1..25
                            mol_type = other DNA
                            organism = synthetic construct
SEQUENCE: 45
ttcataattg cataatattg tccgc                                             25

SEQ ID NO: 46               moltype = DNA   length = 24
FEATURE                     Location/Qualifiers
source                      1..24
                            mol_type = other DNA
                            organism = synthetic construct
SEQUENCE: 46
gacagtgcag taataatatg aacc                                              24

SEQ ID NO: 47               moltype = DNA   length = 20
FEATURE                     Location/Qualifiers
source                      1..20
                            mol_type = other DNA
                            organism = synthetic construct
SEQUENCE: 47
tcgacgaatg gtagcgcttg                                                   20

SEQ ID NO: 48               moltype = DNA   length = 20
FEATURE                     Location/Qualifiers
source                      1..20
                            mol_type = other DNA
                            organism = synthetic construct
SEQUENCE: 48
cttagattag attgctatgc                                                   20

SEQ ID NO: 49               moltype = DNA   length = 20
FEATURE                     Location/Qualifiers
source                      1..20
                            mol_type = other DNA
                            organism = synthetic construct
SEQUENCE: 49
cctcaaacaa gaattgtacg                                                   20

SEQ ID NO: 50               moltype = DNA   length = 20
FEATURE                     Location/Qualifiers
source                      1..20
                            mol_type = other DNA
                            organism = synthetic construct
SEQUENCE: 50
aattgtccct aagaccggcc                                                   20

SEQ ID NO: 51               moltype = DNA   length = 20
FEATURE                     Location/Qualifiers
source                      1..20
```

-continued

```
                            mol_type = other DNA
                            organism = synthetic construct
SEQUENCE: 51
gatacttatc attaagaaaa                                              20

SEQ ID NO: 52          moltype = DNA  length = 20
FEATURE                Location/Qualifiers
source                 1..20
                       mol_type = other DNA
                       organism = synthetic construct
SEQUENCE: 52
tgattcaatc attcttattg                                             20

SEQ ID NO: 53          moltype = DNA  length = 20
FEATURE                Location/Qualifiers
source                 1..20
                       mol_type = other DNA
                       organism = synthetic construct
SEQUENCE: 53
taactattac ttgtttctat                                             20

SEQ ID NO: 54          moltype = DNA  length = 20
FEATURE                Location/Qualifiers
source                 1..20
                       mol_type = other DNA
                       organism = synthetic construct
SEQUENCE: 54
tctgtcaatt tcagctgggg                                             20

SEQ ID NO: 55          moltype = DNA  length = 20
FEATURE                Location/Qualifiers
source                 1..20
                       mol_type = other DNA
                       organism = synthetic construct
SEQUENCE: 55
ccatcttgtg tgctggtatc                                             20

SEQ ID NO: 56          moltype = DNA  length = 20
FEATURE                Location/Qualifiers
source                 1..20
                       mol_type = other DNA
                       organism = synthetic construct
SEQUENCE: 56
ggaaaagcct ccatatccaa                                             20

SEQ ID NO: 57          moltype = DNA  length = 20
FEATURE                Location/Qualifiers
source                 1..20
                       mol_type = other DNA
                       organism = synthetic construct
SEQUENCE: 57
ggctgccgaa aagcctttca                                             20

SEQ ID NO: 58          moltype = DNA  length = 20
FEATURE                Location/Qualifiers
source                 1..20
                       mol_type = other DNA
                       organism = synthetic construct
SEQUENCE: 58
tgcaaacttg gcaccggaag                                             20

SEQ ID NO: 59          moltype = DNA  length = 20
FEATURE                Location/Qualifiers
source                 1..20
                       mol_type = other DNA
                       organism = synthetic construct
SEQUENCE: 59
agtcacacgc ccatccgagc                                             20

SEQ ID NO: 60          moltype = DNA  length = 20
FEATURE                Location/Qualifiers
source                 1..20
                       mol_type = other DNA
                       organism = synthetic construct
SEQUENCE: 60
tagagggacc tgtgtttgac                                             20

SEQ ID NO: 61          moltype = DNA  length = 20
FEATURE                Location/Qualifiers
```

-continued

```
source                    1..20
                          mol_type = other DNA
                          organism = synthetic construct
SEQUENCE: 61
attactatat tgcaaaataa                                            20

SEQ ID NO: 62             moltype = DNA   length = 1032
FEATURE                   Location/Qualifiers
source                    1..1032
                          mol_type = other DNA
                          organism = synthetic construct
SEQUENCE: 62
atggtcaaag tcgcaattct tggcgcttct ggtggcgtgg gacaaccgct atcattactg   60
ctaaaattaa gcccttacgt ttccgagctg gcgttgtacg atatccgagc tgcggaaggc   120
attggtaagg atttatctca catcaacacc aactcaagtt gtgtcggtta tgataaggat   180
agtattgaga acaccttgtc aaatgctcag gtggtgctaa taccggctgg tgttcccaga   240
aagcccggtt taactagaga tgatttgttc aagatgaacg ccggtattgt caaaagcctg   300
gtaaccgctg ttggaaagtt cgcaccaaat gcgaggattt tagtcatttc aaaccctgta   360
aacagtttgg tccctattgc tgtggaaact ttgaagaaaa tgggtaagtt caaacctgga   420
aacgttatgg tgtgtgacgaa ccttgacctg gtacgtgcag aaacctttt ggtagattat   480
ttgatgctaa aaaaccccaa aattggacaa gaacaagaca aaactacaat gcacagaaag   540
gtcactgtta ttgggggtca ttcagggga accattatcc caataatcac cgacaaatcg   600
ctggtatttc aacttgataa gcagtacgag cacttcattc ataggtcca gttcggaggt   660
gatgaaattg tcaaagctaa acagggcgcc ggttccgcca cgttgtccat ggcgttcgcg   720
ggggccaagt ttgctgaaga agtttttgagg agcttccata atgagaaacc agaaacggag   780
tcactttccg cattcgttta tttaccaggc ttaaaaaacg gtaagaaagc gcagcaatta   840
gttggcgaca actctattga gtatttttcc ttgccaattg ttttgagaaa tggtagcgta   900
gtatccatcg ataccagtgt tctggaaaaa ctgtctccga gagaggaaca actcgttaat   960
actgcggtca aagagctacg caagaatatt gaaaaaggca agagtttcat cctagactct  1020
tccaagctat ga                                                     1032

SEQ ID NO: 63             moltype = DNA   length = 201
FEATURE                   Location/Qualifiers
source                    1..201
                          mol_type = other DNA
                          organism = synthetic construct
SEQUENCE: 63
ctgcacaata tttcaagcta taccaagcat acaatcaact atctcatata caatgtctat   60
cccagaaact caaaaggtg ttatcttcta cgaatcccac gtcggcttgt ctaccttgcc   120
agaaatttac gaaaagatgg aaaagggtca aatcgttggt agatacgttg ttgacacttc   180
taaataagcg aatttcttat g                                            201

SEQ ID NO: 64             moltype = DNA   length = 200
FEATURE                   Location/Qualifiers
source                    1..200
                          mol_type = other DNA
                          organism = synthetic construct
SEQUENCE: 64
ttaattttct tttatcttac tctcctacat aagacatcaa gaaacaattg tatattgtac   60
accccccccc tccacaaaca caaatattga taatataaag atttattgga gaaagataac   120
atatcatact ttcccccact tttttcgagg ctcttctata tcatattcat aaattagcat   180
tatgtcattt ctcataacta                                              200

SEQ ID NO: 65             moltype = DNA   length = 200
FEATURE                   Location/Qualifiers
source                    1..200
                          mol_type = other DNA
                          organism = synthetic construct
SEQUENCE: 65
cgctcccctt ccttatcaat gcttgctgtc agaagattaa caagatacac attccttaag   60
cgaacgcatc cggtgttata tactcgtcgt gcatataaaa attcgaggca gtctaccaga   120
tagtctacaa caacgtccgc atggaagacc taccggagat gattgaagag ctagacatcg   180
atgacgaata gacactctcc                                              200

SEQ ID NO: 66             moltype = DNA   length = 885
FEATURE                   Location/Qualifiers
source                    1..885
                          mol_type = other DNA
                          organism = synthetic construct
SEQUENCE: 66
atgccagcac attttgcccc atcccaacca ttacaaggtg ggccaagccc cagccaactg   60
ggaccaaaag aactgctgat tgagagggct cttaccagac tacgttccat ccccaacgac   120
ttagaaaaat acacattttt agcggggcta agaggaagaa atccagacgt tttttatgga   180
ttagtcgggg gaaatatgaa agagtgttgc ccgattatat ataccccagt gataggcgtt   240
gcctgtcaaa attggtcctt aatccatccg cctcccctg aatccgaccc aacgattgac   300
gctctttact tgagttatag cgatcttcca aacctacccc agcttatcgg tgggttaaag   360
acaaggttac ctcatgatca gatgcagatc agcgttgtca ctgacggtag ccgtgtcctt   420
ggcttaggtg atctggggt tggcggaatg gggatatccc aaggaaagct atcactgtat   480
gtcgccgcag ggggtgtgaa tcctaaagcc actttgccta tagcaattga tttcggcaca   540
```

```
gataatgaga ctctgctagc cgatccgttg tacgtaggtc aaaggattcg tagattgagc  600
caggagaagt gcttagagtt catggaggtc tttatgcgtt gcatgcatga gacttttccc  660
aatatggtaa tccaacacga agattggcaa actccgctgg ccttccctct attacacaaa  720
aaccgtgatc tatacccatg cttcaacgat gatatccaag gaaccggcgc tgtagtactg  780
gccggcgcca taagagcatt ccatctgaac ggcgtcgcac tgaaagacca gaaaattttg  840
ttctttggcg cggggtcaag tggcgtgggt gtcgcggaga cgatc              885
```

```
SEQ ID NO: 67          moltype = DNA   length = 792
FEATURE                Location/Qualifiers
source                 1..792
                       mol_type = other DNA
                       organism = synthetic construct
SEQUENCE: 67
ggcgcggggt caagtggcgt gggtgtcgcg gagacgatct gcaaatactt tgagctacag  60
gggatgagtg aagatgaagc taaaagcaaa ttctggttgg ttgatagtaa ggggctagtt  120
gctcacaatc gtggcgatac tttacctagc cacaaaaagt accttgcaag aagtgagcct  180
gatgcgccta aattgaggac gctaaaggaa gtcgtagaac atgtacaacc cacggccttg  240
ttagggctta gcacagttgg gggtacattc acaaaggaaa tcttgaagc aatggccact  300
tataacaaac gtcctattgt ctttgcactt agcaatccag tagcgcaagc tgaatgcacg  360
ttcgaggaag ctgtggaggg aaccgacgga agggtcttat atgccagtgg aagtcccttt  420
gaccccgtgg agtacaaagg caaaaggtat gaaccaggac agggcaacaa tatgtacatc  480
ttccccggcc tgggtatagg tgccattttg gcgagggtga gtaaaatccc ggaagagctg  540
gttcatgcat cagcacaagg gcttgcggac tcattaacgc cggaggaaac ggcgcgtcat  600
ttgctgtatc cagatataga acgtataagg gaagttagta ttaagatagc agttaccgta  660
atccaagcgg cacagaagct tggtgttgat agaaacgagg agcttagagg gaaaagcagt  720
gctgaaattg aagcctatgt acgtaaaggg atgtaccatc cattacttga ggcggaacag  780
caggcacagt ag                                              792
```

```
SEQ ID NO: 68          moltype = AA   length = 11
FEATURE                Location/Qualifiers
source                 1..11
                       mol_type = protein
                       organism = synthetic construct
SEQUENCE: 68
PIRPDAVILV V                                               11
```

```
SEQ ID NO: 69          moltype = DNA   length = 33
FEATURE                Location/Qualifiers
source                 1..33
                       mol_type = other DNA
                       organism = synthetic construct
SEQUENCE: 69
cccattcgac cagacgcagt catcttggtg gta                      33
```

```
SEQ ID NO: 70          moltype = AA   length = 570
FEATURE                Location/Qualifiers
source                 1..570
                       mol_type = protein
                       organism = Bacillus subtilis
SEQUENCE: 70
MTKATKEQKS LVKNRGAELV VDCLVEQGVT HVFGIPGAKI DAVFDALQDK GPEIIVARHE  60
QNAAFMAQAV GRLTGKPGVV LVTSGPGASN LATGLLTANT EGDPVVALAG NVIRADRLKR  120
THQSLDNAAL FQPITKYSVE VQDVKNIPEA VTNAFRIASA GQAGAAFVSF PQDVVNEVTN  180
TKNVRAVAAP KLGPAADDAI SAAIAKIQTA KLPVVLVGMK GGRPEAIKAV RKLLKKVQLP  240
FVETYQAAGT LSRDLEDQYF GRIGLFRNQP GDLLLEQADV VLTIGYDPIE YDPKFWNING  300
DRTIIHLDEI IADIDHAYQP DLELIGDIPS TINHIEHDAV KVEFAEREQK ILSDLKQYMH  360
EGEQVPADWK SDRAHPLEIV KELRNAVDDH VTVTCDIGSH AIWMSRYFRS YEPLTLMISN  420
GMQTLGVALP WAIGASLVKP GEKVVSVSGD GGFLFSAMEL ETAVRLKAPI VHIVWNDSTY  480
DMVAFQQLKK YNRTSAVDFG NIDIVKYAES FGATGLRVES PDQLADVLRQ GMNAEGPVII  540
DVPVDYSDNI NLASDKLPKE FGELMKTKAL                            570
```

```
SEQ ID NO: 71          moltype = AA   length = 255
FEATURE                Location/Qualifiers
source                 1..255
                       mol_type = protein
                       organism = Bacillus subtilis
SEQUENCE: 71
MKRESNIQVL SRGQKDQPVS QIYQVSTMTS LLDGVYDGDF ELSEIPKYGD FGIGTFNKLD  60
GELIGFDGEF YRLRSDGTAT PVQNGDRSPF CSFTFFTPDM THKIDAKMTR EDFEKEINSM  120
LPSRNLFYAI RIDGLFKKVQ TRTVELQEKP YVPMVEAVKT QPIFNFDNVR GTIVGFLTPA  180
YANGIAVSGY HLHFIDEGRN SGGHVFDYVL EDCTVTISQK MNMNLRLPNT ADFFNANLDN  240
PDFAKDIETT EGSPE                                          255
```

```
SEQ ID NO: 72          moltype = AA   length = 343
FEATURE                Location/Qualifiers
source                 1..343
                       mol_type = protein
                       organism = Saccharomyces cerevisiae
SEQUENCE: 72
```

```
MVKVAILGAS GGVGQPLSLL LKLSPYVSEL ALYDIRAAEG IGKDLSHINT NSSCVGYDKD   60
SIENTLSNAQ VVLIPAGVPR KPGLTRDDLF KMNAGIVKSL VTAVGKFAPN ARILVISNPV  120
NSLVPIAVET LKKMGKFKPG NVMGVTNLDL VRAETFLVDY LMLKNPKIGQ EQDKTTMHRK  180
VTVIGGHSGE TIIPIITDKS LVFQLDKQYE HFIHRVQFGG DEIVKAKQGA GSATLSMAFA  240
GAKFAEEVLR SFHNEKPETE SLSAFVYLPG LKNGKKAQQL VGDNSIEYFS LPIVLRNGSV  300
VSIDTSVLEK LSPREEQLVN TAVKELRKNI EKGKSFILDS SKL                    343

SEQ ID NO: 73        moltype = AA  length = 545
FEATURE              Location/Qualifiers
source               1..545
                     mol_type = protein
                     organism = Rhodosporidium toruloides
SEQUENCE: 73
MPSTFAPSQP LQGGPSPSQL GPKELLIERA LTRLRSIPSD LEKYTFLAGL RCRNPDVFYG   60
LVGGNMKECC PIIYTPVIGL ACQNWSLIHP PPPESDPTIE ALYLSYSDLP NLPSLIKGLK  120
TRLPHNQMQI SVVTDGSRVL GLGDLGVGGM GISQGKLSLY VAAGGVNPKA TLPIAIDFGT  180
DNEKLLADPL YVGQRMRRLS EEKCLEFMDV FMRCMHETFP NMVIQHEDWQ TPLAFPLLHK  240
NRDLYPCFND DIQGTGAVVL AGAIRAFHLN GVALKDQKIL FFGAGSSGVG VAETICKYFE  300
LQGMSEQEAK SKFWLVDSKG LVAHNRGDTL PSHKKYLARS EPDAPKLRSL KEVVEHVQPT  360
ALLGLSTVGG TFTKEILESM ATYNKRPIVF ALSNPVAQAE CTFEEAIEGT DGRVLYASGS  420
PFDPVEYKEK RYEPGQGNNM YIFPGLGIGA ILARVSKIPE ELVHASAQGL ADSLTPEETA  480
RHLLYPDIER IREVSIKIAV TVIQAAQKLG VDRNEELRGK SSAEIEAYVR KGMYHPLLEA  540
EQQAQ                                                              545

SEQ ID NO: 74        moltype = AA  length = 318
FEATURE              Location/Qualifiers
source               1..318
                     mol_type = protein
                     organism = Scheffersomyces stipitis
SEQUENCE: 74
MPSIKLNSGY DMPAVGFGCW KVDVDTCSEQ IYRAIKTGYR LFDGAEDYAN EKLVGAGVKK   60
AIDEGIVKRE DLFLTSKLWN NYHHPDNVEK ALNRTLSDLQ VDYVDLFLIH FPVTFKFVPL  120
EEKYPPGFYC GKGDNFDYED VPILETWKAL EKLVKAGKIR SIGVSNFPGA LLLDLLRGAT  180
IKPSVLQVEH HPYLQQPRLI EFAQSRGIAV TAYSSFGPQS FVELNQGRAL NTSPLFENET  240
IKAIAAKHGK SPAQVLLRWS SQRGIAIIPK SNTVPRLLEN KDVNSFDLDE QDFADIAKLD  300
INLRFNDPWD WDKIPIFV                                                318

SEQ ID NO: 75        moltype = AA  length = 363
FEATURE              Location/Qualifiers
source               1..363
                     mol_type = protein
                     organism = Scheffersomyces stipitis
SEQUENCE: 75
MTANPSLVLN KIDDISFETY DAPEISEPTD VLVQVKKTGI CGSDIHFYAH GRIGNFVLTK   60
PMVLGHESAG TVVQVGKGVT SLKVGDNVAI EPGIPSRFSD EYKSGHYNLC PHMAFAATPN  120
SKEGEPNPPG TLCKYFKSPE DFLVKLPDHV SLELGALVEP LSVGVHASKL GSVAFGDYVA  180
VFGAGPVGLL AAAVAKTFGA KGVIVVDIFD NKLKMAKDIG AATHTFNSKT GGSEELIKAF  240
GGNVPNVVLE CTGAEPCIKL GVDAIAPGGR FVQVGNAAGP VSFPITVFAM KELTLFGSFR  300
YGFNDYKTAV GIFDTNYQNG RENAPIDFEQ LITHRYKFKD AIEAYDLVRA GKGAVKCLID  360
GPE                                                                363

SEQ ID NO: 76        moltype = AA  length = 683
FEATURE              Location/Qualifiers
source               1..683
                     mol_type = protein
                     organism = Scheffersomyces stipitis
VARIANT              597
                     note = Any amino acid
SEQUENCE: 76
MTANPSLVLN KIDDISFETY DAPEISEPTD VLVQVKKTGI CGSDIHFYAH GRIGNFVLTK   60
MTTTPFDAPD KLFLGFDLST QQLKIIVTDE NLAALKTYNV EFDSINSSVQ KGVIAINDEI  120
SKGAIISPVY MWLDALDHVF EDMKKDGFPF NKVVGISGSC QQHGSVYWSR TAEKVLSELD  180
AESSLSSQMR SAFTFKHAPN WQDHSTGKEL EEFERVIGAD ALADISGSRA HYRFTGLQIR  240
KLSTRFKPEK YNRTARISLV SSFVASVLLG RITSIEEADA CGMNLYDIEK REFNEELLAI  300
AAGVHPELDG VEQDGEIYRA GINELKRKLG PVKPITYESE GDIASYFVTR YGFNPDCKIY  360
SFTGDNLATI ISLPLAPNDA LISLGTSTTV LIITKNYAPS SQYHLFKHPT MPDHYMGMIC  420
YCNGSLAREK VRDEVNEKFN VEDKKSWDKF NEILDKSTDF NNKLGIYFPL GEIVPNAAAQ  480
IKRSVLNSKN EIVDVELGDK NWQPEDDVSS IVESQTLSCR LRTGPMLSKS GDSSASSSAS  540
PQPEGDGTDL HKVYQDLVKK FGDLFTDGKK QTFESLTARP NRCYYVGGAS NNGSIIXKMG  600
SILAPVNGNY KVDIPNACAL GGAYKASWSY ECEAKKEWIG YDQYINRLFE VSDEMNSFEV  660
KDKWLEYANG VGMLAKMESE LKH                                          683

SEQ ID NO: 77        moltype = AA  length = 382
FEATURE              Location/Qualifiers
source               1..382
                     mol_type = protein
                     organism = Saccharomyces cerevisiae
SEQUENCE: 77
MRALAYFKKG DIHFTNDIPR PEIQTDDEVI IDVSWCGICG SDLHEYLDGP IFMPKDGECH   60
```

-continued

```
KLSNAALPLA MGHEMSGIVS KVGPKVTKVK VGDHVVVDAA SSCADLHCWP HSKFYNSKPC   120
DACQRGSENL CTHAGFVGLG VISGGFAEQV VVSQHHIIPV PKEIPLDVAA LVEPLSVTWH   180
AVKISGFKKG SSALVLGAGP IGLCTILVLK GMGASKIVVS EIAERRIEMA KKLGVEVFNP   240
SKHGHKSIEI LRGLTKSHDG FDYSYDCSGI QVTFETSLKA LTFKGTATNI AVWGPKPVPF   300
QPMDVTLQEK VMTGSIGYVV EDFEEVVRAI HNGDIAMEDC KQLITGKQRI EDGWEKGFQE   360
LMDHKESNVK ILLTPNNHGE MK                                            382

SEQ ID NO: 78            moltype = DNA   length = 30
FEATURE                  Location/Qualifiers
source                   1..30
                         mol_type = other DNA
                         organism = synthetic construct
SEQUENCE: 78
cccattcgac cagacgcagt catcttggta                                    30

SEQ ID NO: 79            moltype = AA   length = 10
FEATURE                  Location/Qualifiers
source                   1..10
                         mol_type = protein
                         organism = synthetic construct
SEQUENCE: 79
PIRPDAVILV                                                          10
```

2,3-BUTANEDIOL PRODUCTION, METHYL ETHYL KETONE PRODUCTION, AND INDUCTION OF DROUGHT TOLERANCE IN PLANTS

PRIORITY

This application claims the benefit of U.S. Ser. No. 63/358,527, which was filed on Jul. 6, 2022, which is incorporated by reference herein in its entirety.

GOVERNMENT SUPPORT CLAUSE

This invention was made with government support under contract number DE-SC0018420 awarded by the Department of Energy. The United States Government has certain rights in the invention.

BACKGROUND

Due to global warming and a changing climate, research on the production of biofuels and chemicals from renewable resources has been steadily progressing in recent decades [1, 2]. One such example is the production of 2,3-butanediol (2,3-BDO), a multi-functional chemical with numerous industrial applications such as softening agents, plasticizers, drugs, and cosmetics [3, 4]. Intriguingly, a recent study suggested a potential usage of 2,3-BDO as a Mars-specific rocket propellant [5]. Also, 2,3-BDO can be used as a platform chemical for producing methyl ethyl ketone (MEK). MEK is a common industrial solvent in paints and coating formulations [6]. Moreover, MEK can be used as an efficient fuel additive to produce high-quality aviation fuels because it offers a higher heat of combustion than ethanol [7]. The global MEK market size is anticipated to reach USD 4.01 billion and its production to 2.11 million tons by 2024 [8]. Currently, MEK is mainly produced using a two-step chemical process based on the hydration of butylene to secondary butanol and then dehydration to MEK [9]. However, this process requires high investment costs and poses serious equipment corrosion and environmental issues [10]. As the catalytic dehydration of 2,3-BDO into MEK is reported with yields up to 95% [3, 11], an integrated conversion process consisting of biological 2,3-BDO production and catalytic dehydration of 2,3-BDO would have the potential for greater financial viability and environmental benefits than those of the conventional chemical process [6].

Most studies on the biological production of 2,3-BDO have been limited to bacteria such as *Klebsiella, Enterobacter*, and *Bacillus* species. However, most of these native 2,3-BDO producers are classified as Risk Group 2 pathogens (pathogenic to humans), which hinders their applicability in industrial 2,3-BDO production [3, 4].

In the past 2,3-BDO titers, yields, and productivities by engineered yeast such as *S. cerevisiae* were inferior to bacterial 2,3-BDO producers because of two major metabolic limitations. First, ethanol production is a barrier to efficient 2,3-BDO production by *S. cerevisiae*. To redirect carbon flux toward 2,3-BDO from ethanol production, pyruvate decarboxylase (Pdc) or alcohol dehydrogenase (Adh) isozymes have been deleted in engineered *S. cerevisiae* strains [12-15]. Although Pdc-deficient (Pdc⁻) and Adh-deficient (Adh⁻) strains produced 2,3-BDO as a major product without ethanol production, they exhibited severe growth defects on glucose medium due to a limited synthesis of cytosolic acetyl-CoA [13, 16] or accumulation of toxic intermediates such as acetaldehyde and acetate [14]. Second, redox imbalance caused by eliminating Pdc and Adh isozymes resulted in impaired cell growth and glycerol accumulation during 2,3-BDO production, leading to low 2,3-BDO productivities and yields [13, 15, 16]. The chemical properties of glycerol and 2,3-BDO are similar, so downstream processing for purification could be complicated, increasing the cost. Previously, partial restoration of Pdc activity [17, 18], redirection of pyruvate carbon flux into 2,3-BDO biosynthesis [12], introduction of a heterologous NADH oxidase [13, 15, 17-19], and deletion of the glycerol production pathway [15, 19] have been attempted to improve 2,3-BDO production by engineered *S. cerevisiae*. Nonetheless, insufficient 2,3-BDO productivity and yield as compared to 2,3-BDO titer are still a hurdles for industrial 2,3-BDO production via yeast fermentation [20].

Methods are needed in the art to produce 2,3-BDO.

DETAILED DESCRIPTION OF THE FIGURES

FIG. 1 shows a metabolic pathway for 2,3-butanediol (2,3-BDO) production. Two molecules of pyruvate are converted to one molecule of 2,3-butanediol via α-acetolactate and acetoin by sequential actions of α-acetolactate synthase (AlsS), α-acetolactate decarboxylase (AlsD), and 2,3-butanediol dehydrogenase (Bdh1). Dashed arrows indicate multiple enzymatic steps. GAP, glycerol-3-phosphate; DHAP, dihydroxyacetone phosphate; G3P, glycerol-3-phophate.

Figure 2:
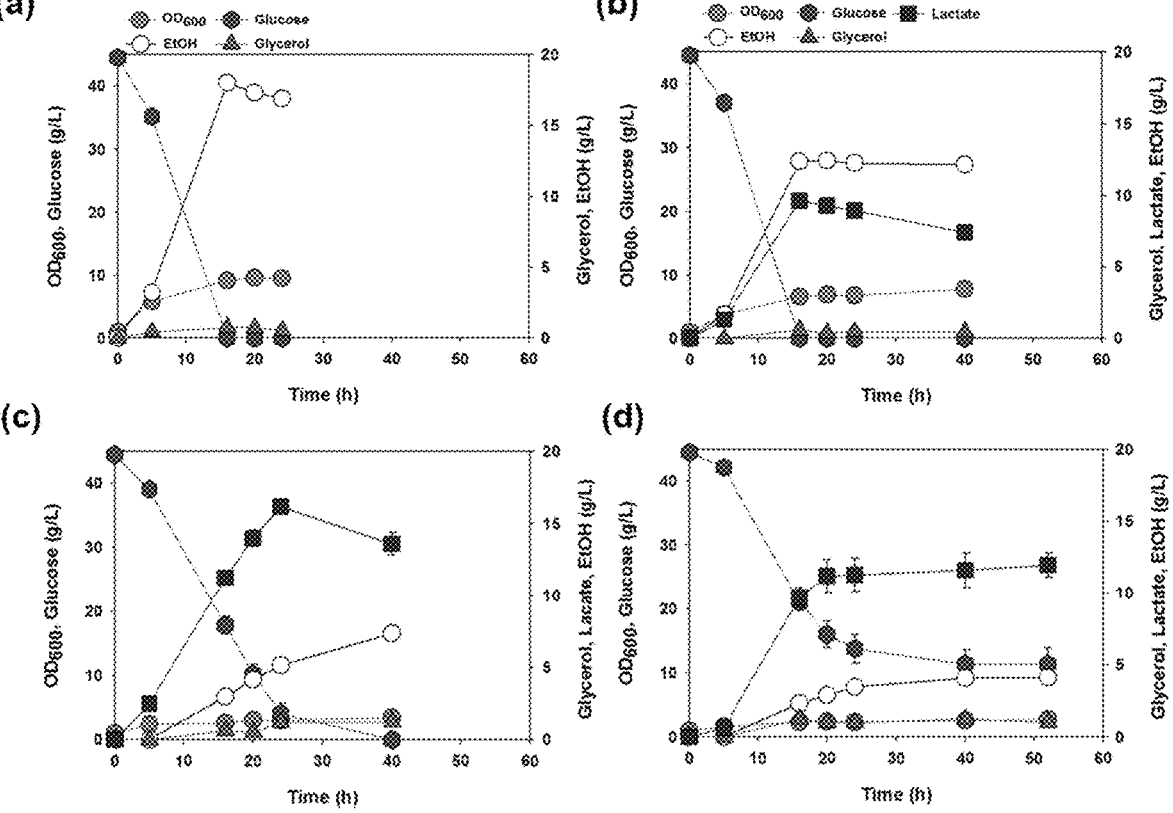

FIG. 2 panels (a)-(d) shows batch fermentation profiles of (a) the CT2 strain, (b) the CTL strain, (c) the CTLA strain, and (d) the CTLAP strain in YPD40 (YP medium with 40 g/L of glucose) under oxygen-limited conditions. Symbols: $OD_{600}$ (closed circle), glucose (hexagon), lactate (rectangular), ethanol (open circle), and glycerol (triangle up). Results are the mean of duplicated experiments and error bars represent standard deviations.

Figure 3:
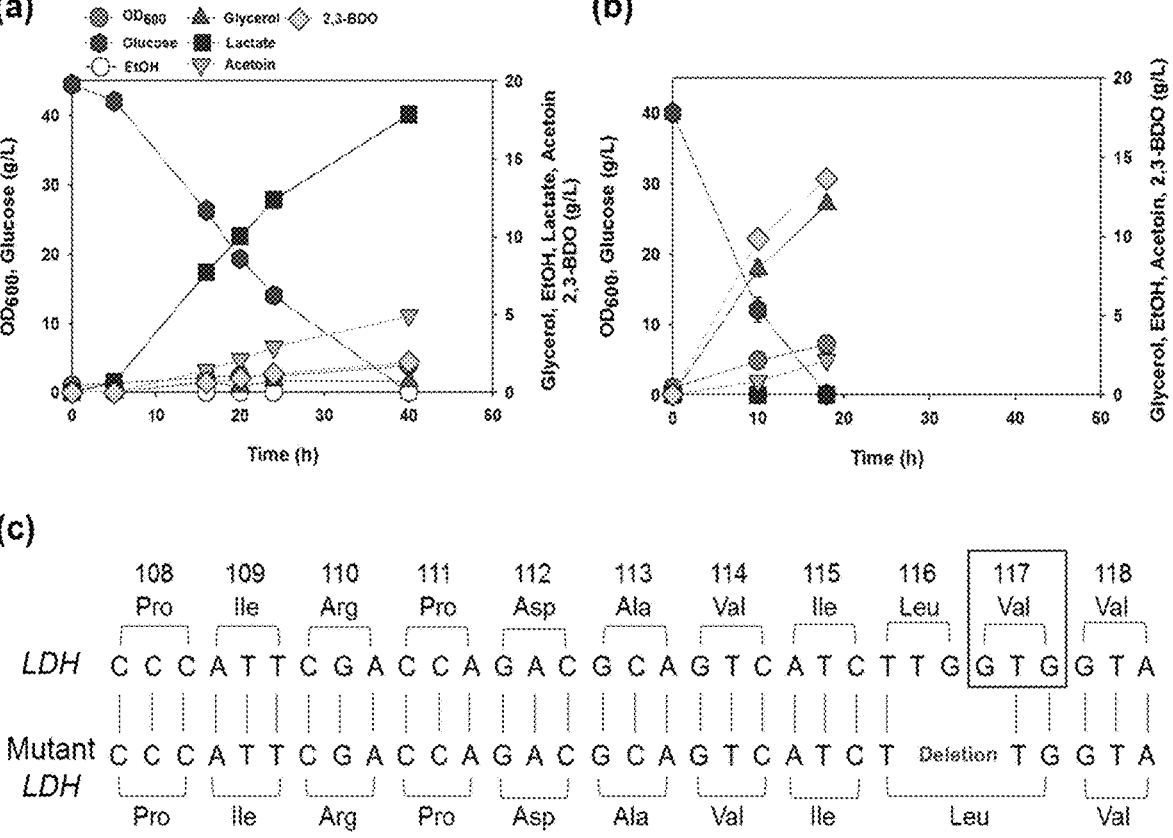

FIG. 3 panels (a)-(c) shows a comparison of phenotypic and genotypic changes between the CTLAB and the CTLABM strains. Batch fermentation profiles of (a) the CTLAB strain and (b) the CTLABM strain in YPD40 under oxygen-limited conditions. (c) The ldhA gene alignments of the CTLAB strain (SEQ ID NO:68) and the CTLABM strain (SEQ ID NO:69). The 117$^{th}$ amino acid (valine) of the lactate dehydrogenase (LDH) is missing in the CTLABM strain. Results are the mean of duplicated experiments and error bars represent standard deviations.

Figure 4:
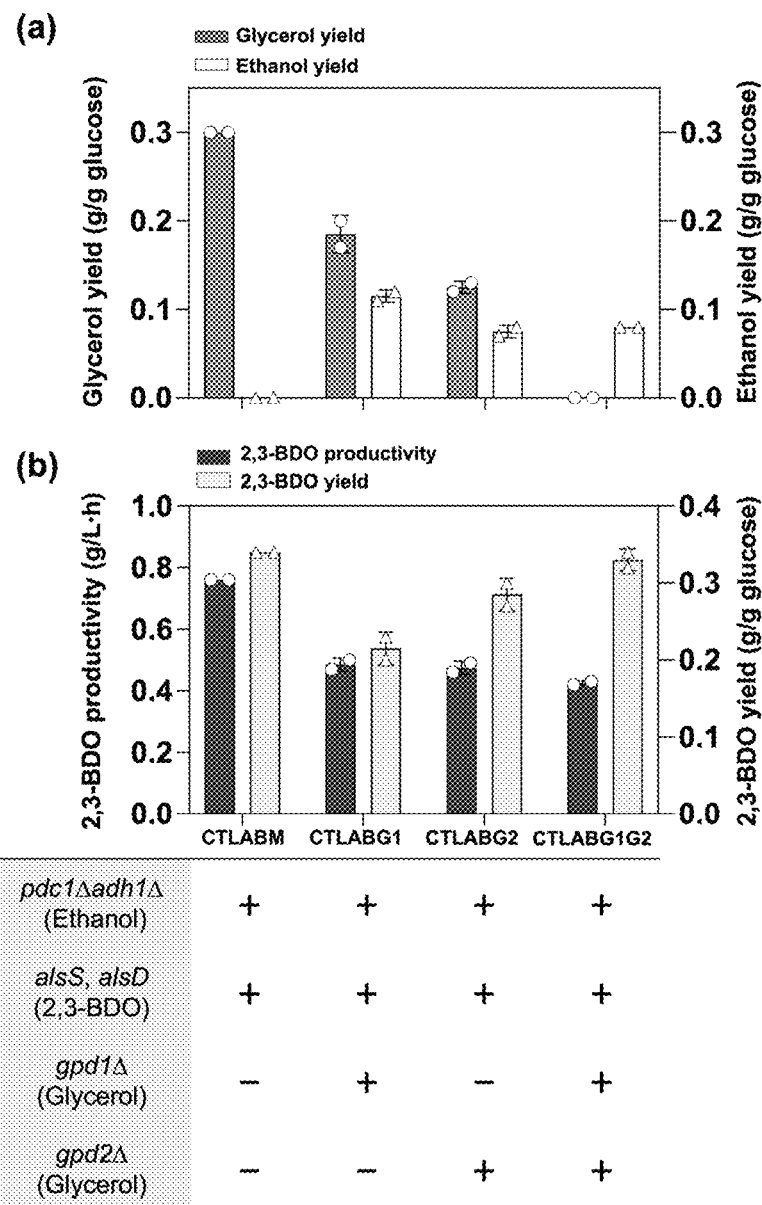

FIG. 4 panels (a)-(b) shows the effects of deletion of Gpd isozymes on (a) glycerol and ethanol yields (g/g), (b) 2,3-BDO productivities (g/L/h) and yields (g/g) of the engineered yeast strains (CTLABM, CTLABG1, CTLABG2, and CTLABG1G2) in YPD40 under oxygen-limited conditions. Results are the mean of duplicated experiments and error bars represent standard deviations.

Figure 5:
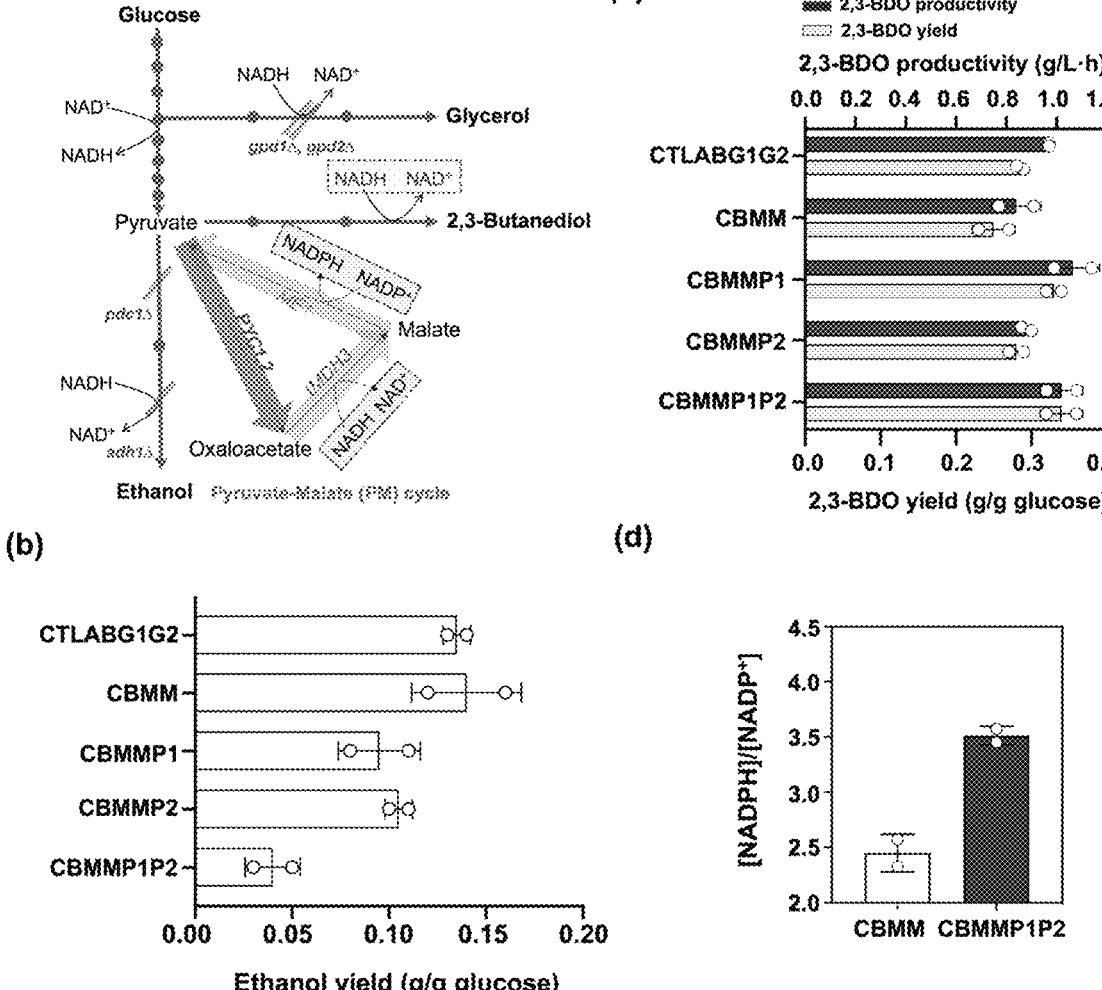

FIG. 5 panels (a)-(d) shows recovering the redox imbalance from the deletion of Pdc, Adh, and Gpd isozymes by employing a Pyruvate-Malate (PM) cycle. (a) A schematic diagram of the PM cycle, (b) ethanol yields (g/g), (c) 2,3-BDO productivities (g/L/h), and 2,3-BDO yields (g/g glucose) of the engineered yeast strains (CBMM, CBMMP1, CBMMP2, and CBMMP1P2) in YPD100 under aerobic conditions, and (d) comparison of the intracellular ratios of NADPH to $NADP^+$ in the CBMM strain and the CBMMP1P2 strain.

Figure 6:
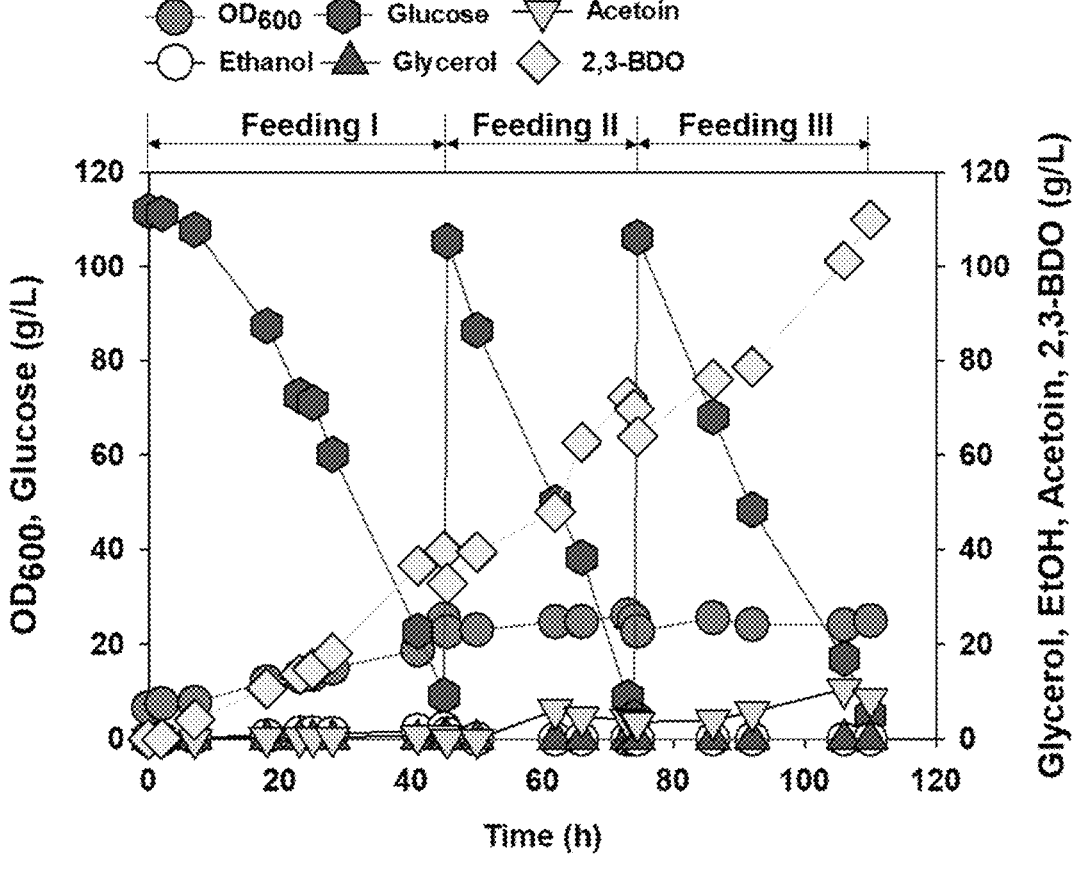

FIG. 6 shows a fed-batch fermentation profile of the CBMMP1P2 strain. Symbols: $OD_{600}$ (closed circle), glucose (hexagon), acetoin (triangle down), ethanol (open circle), glycerol (triangle up), 2,3-BDO (diamond).

Figure 7:
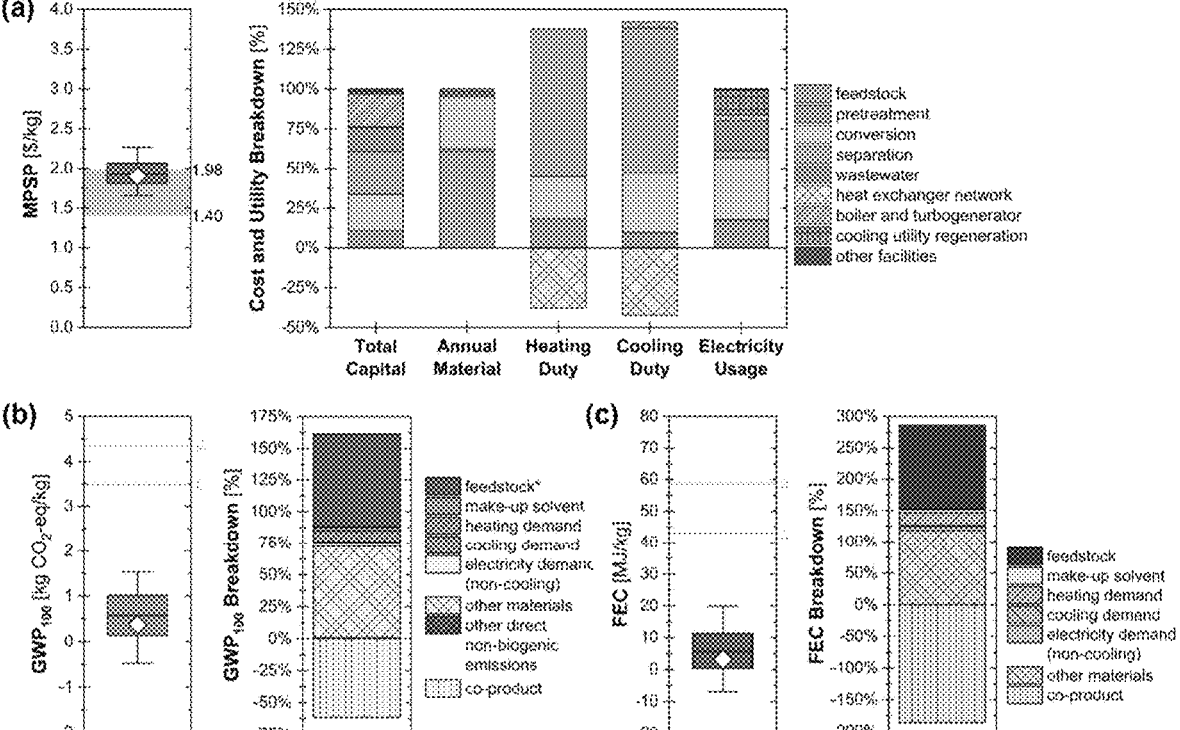

FIG. 7 panels (a)-(c) shows uncertainties (box-and-whisker plots) and breakdowns (stacked bar charts) of (a) minimum product selling price (MPSP), (b) 100-year global warming potential ($GWP_{100}$), and (c) fossil energy consumption (FEC) per kg of methyl ethyl ketone (MEK) produced via 2,3-BDO from neutral fermentation of glucose and xylose by *S. cerevisiae*. Whiskers, boxes, and the middle line represent $5^{th}/95^{th}$ $25^{th}/75^{th}$, and $50^{th}$ percentiles, respectively, from 2,000 Monte Carlo simulations. Diamonds and stacked bar charts report results for baseline values. For MPSP, the shaded gray region shows the market price range for MEK ($1.40-1.98/kg). For $GWP_{100}$ and FEC, gray lines marked with lowercase Roman numerals indicate (i.) petroleum-based MEK (GREET 2020) [55] and (ii.) petroleum-based MEK (ecoinvent 3.7.1) [56]. The breakdown method and categories are consistent with Bhagwat et al. [42]. Tabulated data breaking down capital and material costs, heating and cooling duties, electricity usage, $GWP_{100}$, and FEC are available online [41].

Figure 8:
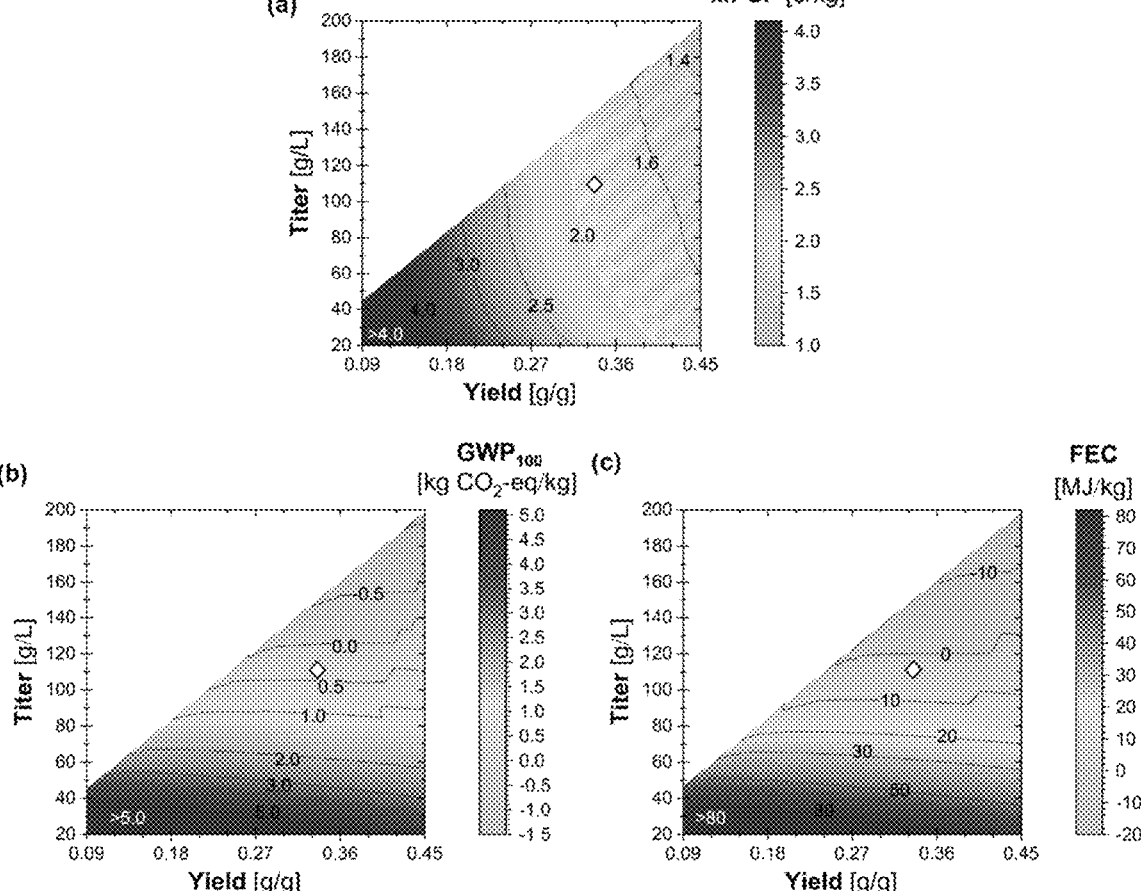

FIG. 8 panels (a)-(c) shows (a) MPSP, (b) $GWP_{100}$, and (c) FEC of MEK across a range of 2,3-BDO titer-yield combinations at a productivity of 1.0 g/L/h. The triangle indicates the baseline result from the CBMMP1P2 strain demonstrated in this study (2,3-BDO titer of 109.9 g/L and overall yield of 0.334 g/g on glucose and xylose; yield on glucose being 0.360 g/g and yield on xylose being 0.288 g/g). The blank area on the top left indicates high-titer, low-yield combinations that cannot be achieved under current design.

Figure 9:
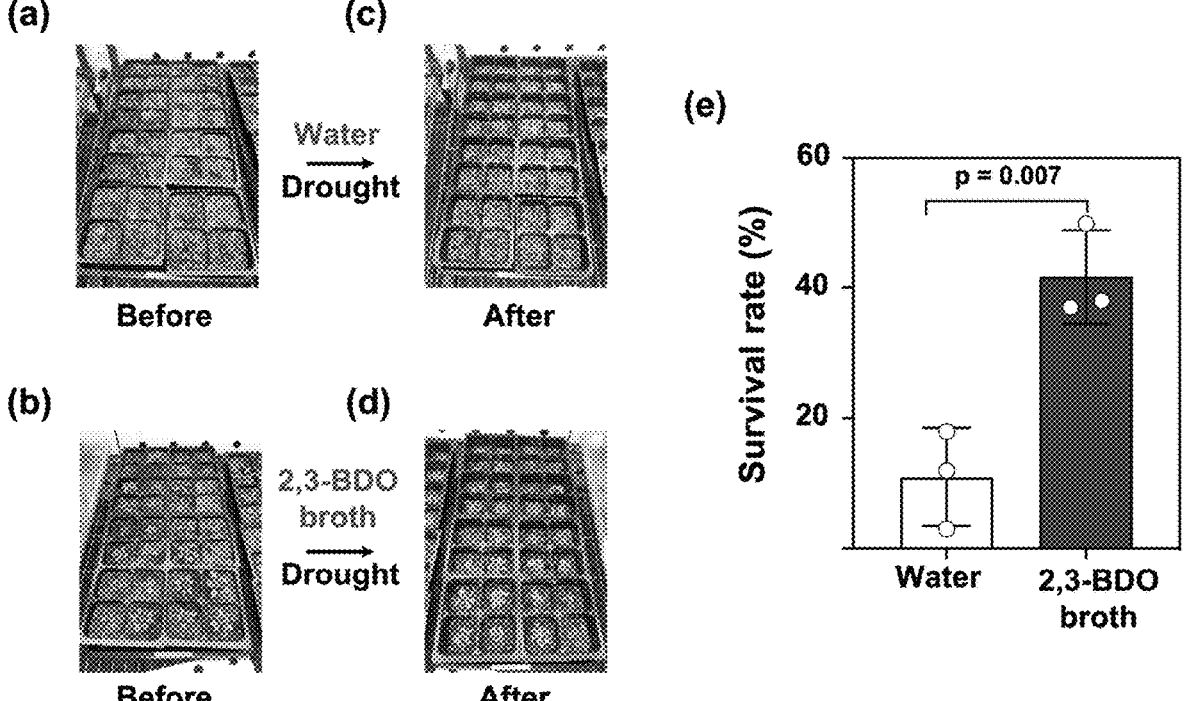

FIG. 9 panels (a)-(e) shows effect of yeast 2,3-BDO fermentation broth on drought tolerance of plants. (a)-(d) Photos of *Arabidopsis thaliana* grown in a growth chamber. (a) and (b) Plants before treatments and drought, (c) plants treated with water as a control and (d) plants treated with 2,3-BDO. (e) The box plots show the median (central line), the lower and upper quartiles (box) and the minimum and maximum values (whiskers). The p-value was calculated using one-way ANOVA (n=3).

Figure 10:
Figure 10:
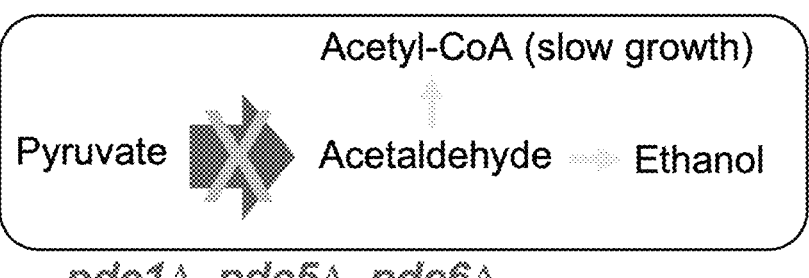
Figure 10:
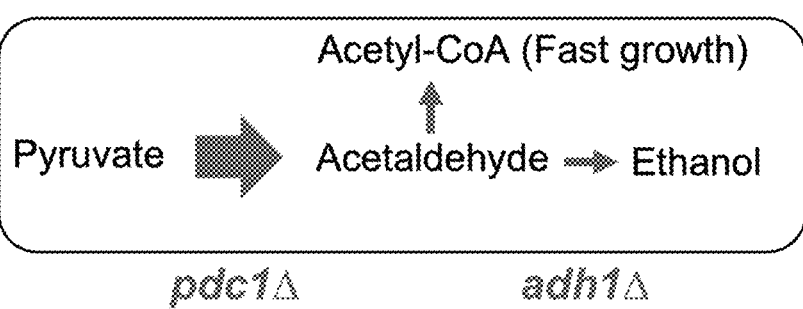

FIG. 10 panels (a)-(b) shows a schematic diagram for (a) Pdc-deficient strain and (b) Pdc1 and Adh1 (pdc1Δ and adh1Δ) deleted strain for 2,3-BDO production.

Figure 11:
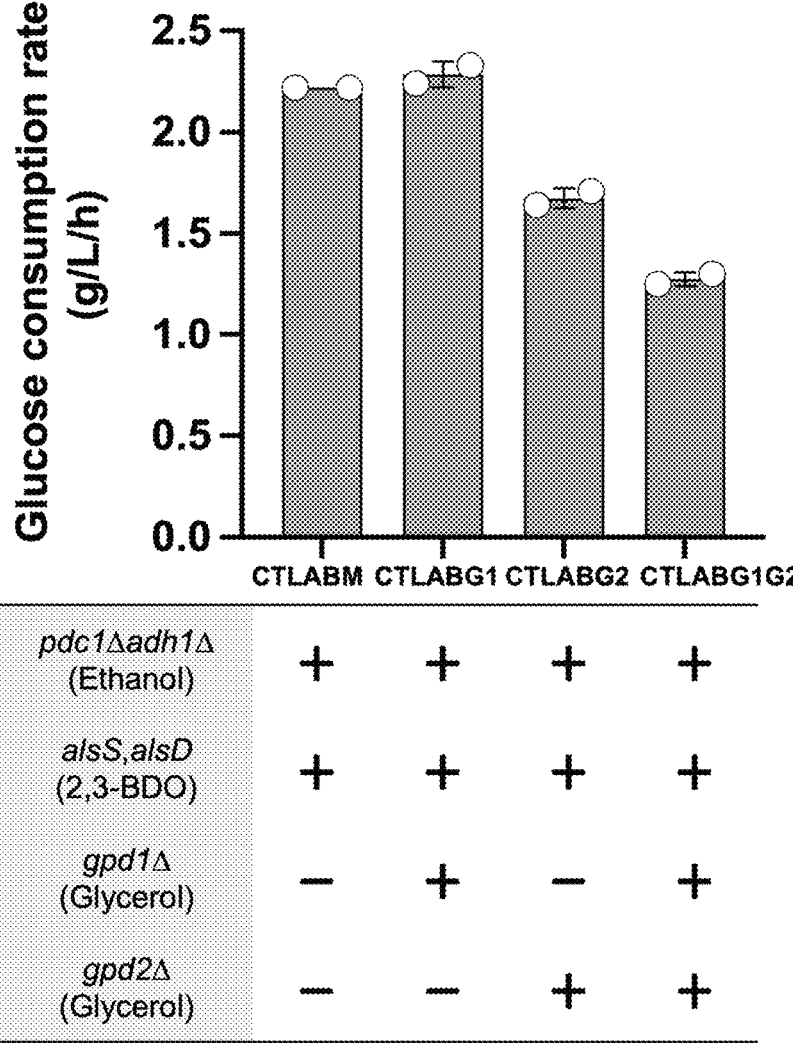

FIG. 11 shows a comparison of the glucose consumption rates of the engineered yeast strains (CTLABM, CTLABG1, CTLABG2, and CTLABG1G2). Results are the mean of duplicated experiments and error bars represent standard deviations.

Figure 12:
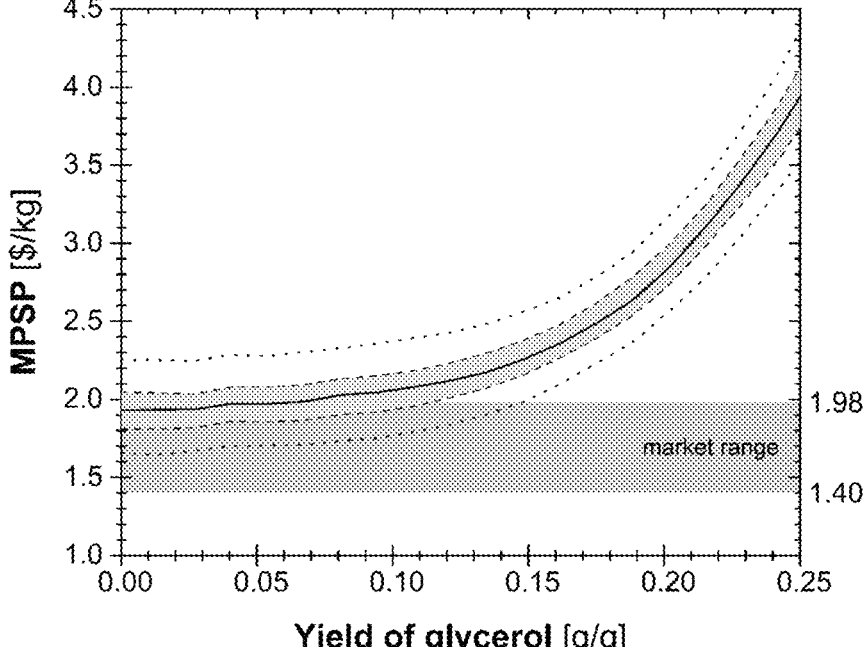

FIG. 12 shows minimum product selling price (MPSP) of methyl ethyl ketone (MEK, produced from 2,3-BDO) with uncertainty across overall yield of glycerol on glucose and xylose (x-axis). Dotted lines, dashed lines, and the middle line represent $5^{th}/95^{th}$, $25^{th}/75^{th}$ and $50^{th}$ percentiles, respectively, from 500 Monte Carlo simulations at each of 25 values for overall yield of glycerol on glucose and xylose. The region shaded gray indicates the market price range ($1.40-1.98/kg).

Figure 13:
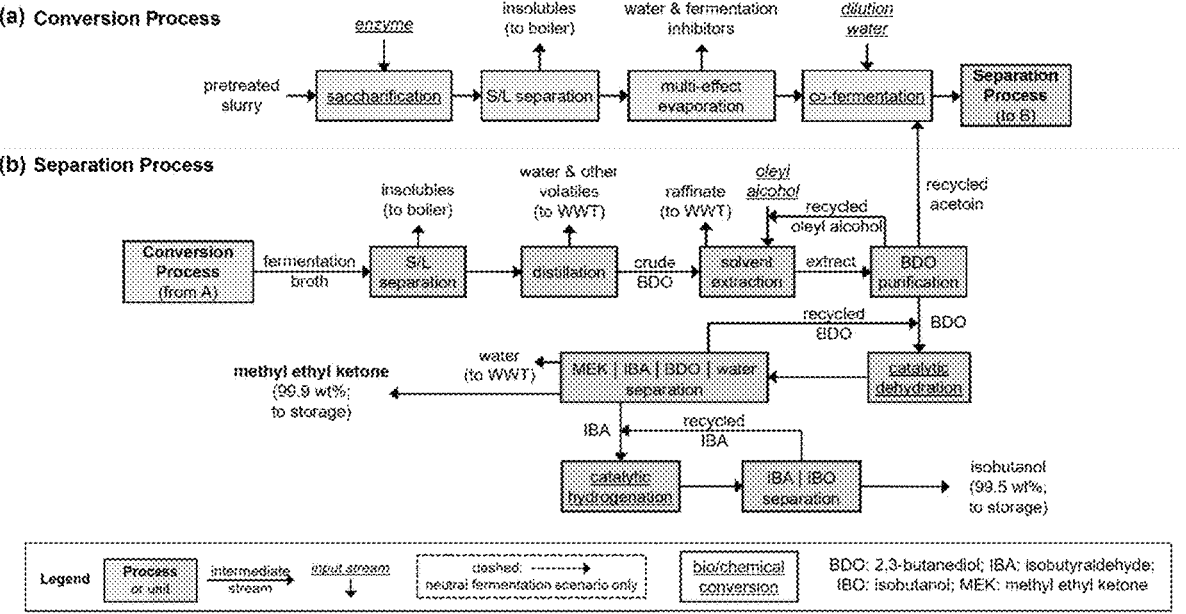

FIG. 13 shows a simplified process flow diagram for (a) conversion (saccharification and fermentation) of pretreated lignocellulosic biomass into crude 2,3-BDO and (b) separation and upgradation of 2,3-BDO to MEK and IBO. Full process flowsheets are available in the online biorefinery repository [6].

SUMMARY

Provided herein are recombinant yeast cells comprising 1, 2, 3, 4, 5, 6, 7, or 8 of the following:

(a) a genetic modification to reduce or eliminate expression of glyceraldehyde-3-phosphate dehydrogenase encoded by GPD1 and GPD2;

(b) a genetic modification to reduce or eliminate expression of pyruvate decarboxylase encoded by PDC1;

(c) a genetic modification to reduce or eliminate expression of alcohol dehydrogenase encoded by ADH1;

(d) a heterologous nucleic acid molecule encoding acetolactate synthase (alsS);

(e) a heterologous nucleic acid molecule encoding acetolactate decarboxylase (alsD);

(f) a genetic modification to increase expression of pyruvate decarboxylase encoded by PYC1 and PYC2 as compared to expression of pyruvate decarboxylase in a wild-type yeast cell;

(g) a heterologous nucleic acid molecule encoding malate dehydrogenase (Mdh3); and/or (h) a heterologous nucleic acid molecule encoding malic enzyme (Me1).

A recombinant yeast cell can further comprise 1, 2, 3, 4, or 5 of the following:

(i) a heterologous nucleic acid molecule encoding xylose reductase (Xyl1);

(j) a heterologous nucleic acid molecule encoding xylitol dehydrogenase (Xyl2);

(k) a heterologous nucleic acid molecule encoding xylulokinase (Xyl3);

(l) a genetic modification to reduce or eliminate expression of 4-nitrophenylphosphatase (Pho13); and/or (m) a genetic modification to reduce or eliminate expression cytosolic aldehyde dehydrogenase (Ald6).

A recombinant yeast cell can further comprise a heterologous nucleic acid molecule encoding butanediol dehydrogenase (Bdh1).

A heterologous nucleic acid molecule encoding a heterologous nucleic acid molecule encoding acetolactate synthase (alsS) can be derived from *Bacillus subtilis*.

A heterologous nucleic acid molecule encoding a heterologous nucleic acid molecule encoding acetolactate synthase (alsD) can be derived from *Bacillus subtilis*.

A genetic modification to increase expression of pyruvate decarboxylase encoded by PYC1 and PYC2 can comprise a strong promoter operably linked to the PYC1 and PYC2. A strong promoter can be a TEF1 promoter, a PGK1 promoter, or any other suitable promoter.

A heterologous nucleic acid molecule encoding malate dehydrogenase (Mdh3) can be derived from *Saccharomyces cerevisiae*.

A nucleic acid molecule encoding Mdh3 can encode a truncated Mdh3 (tMdh3), wherein the last three amino acids (SKL) are absent. A nucleic acid molecule encoding Mdh3 can be operably linked to a strong promoter.

A heterologous nucleic acid molecule encoding malic enzyme (Me1) can be derived from Rhodosporidium toruloides.

A heterologous nucleic acid molecule encoding xylose reductase (Xyl1), xylitol dehydrogenase (Xyl2), and xylulokinase (Xyl3) can be derived from Scheffersomyces *stipitis*.

A recombinant yeast cell can be *Saccharomyces*. The recombinant yeast cell can be capable of fermenting xylose.

An aspect provides a yeast cell culture comprising two or more of the recombinant yeast cells described herein.

Another aspect provides a method of producing 2,3-butanediol (2,3-BDO) comprising contacting a substrate with any of the recombinant yeast cells described herein. The substrate can be lignocellulosic or cellulosic feedstock.

The substrate can comprise glycose, xylose, or a combination of glucose and xylose. Substantially no glycerol or ethanol can be accumulated in the fermentation broth or fermentation media. Less than 2 g/L of ethanol and less than 2 g/L of glycerol can be accumulated in the fermentation broth or fermentation media. 2,3-BDO can be produced at more than 0.5 g/L/h or at more than 1.0 g/L/h. 2,3-BDO can be produced at a yield of 100 g/L or more.

Yet another aspect provides a method of producing methyl ethyl ketone (MEK). The method can comprise:

(a) contacting a substrate with any recombinant yeast cell described herein under fermentation conditions;

(b) collecting and purifying 2,3-BDO to form purified 2,3-BDO;

(c) subjecting the purified 2,3-BDO to catalytic dehydration such that MEK is produced. A catalyst for the catalytic dehydration can be tricalcium phosphate or other suitable catalyst. The purified 2,3-BDO can be greater than 90 wt % pure.

Even another aspect provides a fermentation broth produced by contacting any recombinant yeast cell described herein with a fermentation medium.

An aspect provides a method of inducing drought tolerance in plants comprising contacting roots of the plants with a fermentation broth produced by contacting any recombinant yeast cell described herein with a fermentation medium. The survival rate of the plants can be at least 2-fold higher than plants not contacted with the fermentation broth. The fermentation broth can contain substantially no ethanol. The fermentation broth can contain substantially no glycerol. The fermentation broth can comprise 200 µM or more of 2,3-BDO.

Rising concerns for sustainability and global climate change have driven the development of sustainable production pathways for biofuels and chemicals from lignocellulosic biomass via integrated biological and chemical processes. Therefore, provided herein are engineered yeast capable of producing 2,3-butanediol (2,3-BDO) from lignocellulosic hydrolysates, cellulosic hydrolysates, and other suitable substrates with a high yield and productivity. Also provided are methods of production of methyl ethyl ketone (MEK) through catalytic dehydration of 2,3-BDO. Engineered yeast can produce 2,3-BDO without accumulating glycerol and/or ethanol, which hinders downstream processing of 2,3-BDO. Furthermore, fermentation broth containing 2,3-BDO can be used as a biostimulant inducing drought tolerance in plants.

DETAILED DESCRIPTION

To circumvent limitations of previous attempts to produce 2,3-BDO with recombinant bacteria and yeast, engineered yeast strains were produced, which are capable of producing 2,3-BDO with a high productivity and without by-product production through extensive metabolic reprogramming (FIG. 1). First, we deleted major the isozymes of Pdc and Adh (pdc1Δ and adh1Δ) to minimize ethanol production while maintaining sufficient levels of acetyl-CoA for cell growth (FIG. 10). Second, an alsS gene coding for acetolactate synthase and alsD gene coding for acetolactate decarboxylase were overexpressed to enhance metabolic fluxes toward 2,3-BDO biosynthesis. Third, Gpd isozymes (gpd1Δ and gpd2Δ) were deleted to eliminate glycerol production. Fourth, we introduced an NAD⁺ regenerating Pyruvate-Malate (PM) cycle consisting of endogenous PYC1 and PYC2 genes coding for pyruvate carboxylase, a truncated MDH3 (tMDH3) gene coding for malate dehydrogenase and ME1 gene coding for malic enzyme, to restore the redox imbalance caused by the elimination of glycerol production. Lastly, the expression levels of PYC1 and PYC2 genes were increased to improve the NAD⁺ regenerating capability of the PM cycle. As a result, our engineered strains produced 2,3-BDO with a high productivity without ethanol or glycerol production, which paves the way toward implementation and financially viable downstream processing of 2,3-BDO.

2,3-BDO also has various benefits for plants, such as growth promotion, heat resistance, and disease resistance. Drought is one of the major threats to crop production worldwide. In the U.S., nearly 67% of crop losses reported in the last 50 years were due to drought stress. Intriguingly, evidence from many studies suggests that 2,3-BDO and acetoin trigger hormonal responses inducing systemic drought tolerance in plants. Most studies have focused on understanding the physiological role of 2,3-BDO and acetoin in plants under drought stress by either root colonization with rhizobacteria or root treatment of pure 2,3-BDO and acetoin chemicals. However, the 2,3-BDO delivery methods cannot be applied as a practical solution for field and industrial crops under severe drought stress due to economic and sustainability concerns. To solve this, we established a simple and effective strategy for inducing drought tolerance in plants using yeast 2,3-BDO fermentation broth as a biostimulant without purification processes.

Additionally, we designed, simulated, and evaluated biorefineries producing MEK from lignocellulosic hydrolysates via yeast 2,3-BDO fermentation and catalytic dehydration of 2,3-BDO using BioSTEAM [23, 24]—an open-source platform—as a tool. To efficiently produce MEK from lignocellulosic biomass, we devised an integrated conversion process comprising (i) a biological process using a metabolically engineered yeast producing high levels of 2,3-BDO without ethanol and glycerol production and (ii) a chemical process that dehydrates 2,3-BDO to MEK using a catalyst. We evaluated the financial viability and environmental benefits of MEK-producing biorefineries through design, simulation, techno-economic analysis (TEA), and life cycle assessment (LCA) under uncertainty. This study demonstrated the feasibility of cost-competitive and sustainable bio-based MEK production via yeast 2,3-BDO fermentation from lignocellulosic biomass.

Polynucleotides and Genes

Polynucleotides contain less than an entire microbial genome and can be single- or double-stranded nucleic acids. A polynucleotide can be RNA, DNA, cDNA, genomic DNA, chemically synthesized RNA or DNA or combinations thereof. A polynucleotide can comprise, for example, a gene, open reading frame, non-coding region, or regulatory element.

A gene is any polynucleotide molecule that encodes a polypeptide, protein, or fragment thereof, optionally including one or more regulatory elements preceding (5' non-coding sequences) and following (3' non-coding sequences) the coding sequence. In one embodiment, a gene does not include regulatory elements preceding and following the coding sequence. A native or wild-type gene refers to a gene as found in nature, optionally with its own regulatory elements preceding and following the coding sequence. A chimeric or recombinant gene refers to any gene that is not a native or wild-type gene, optionally comprising regulatory elements preceding and following the coding sequence, wherein the coding sequences and/or the regulatory elements, in whole or in part, are not found together in nature. Thus, a chimeric gene or recombinant gene can comprise regulatory elements and coding sequences that are derived from different sources, or regulatory elements and coding sequences that are derived from the same source, but arranged differently than is found in nature. A gene can encompass full-length gene sequences (e.g., as found in nature and/or a gene sequence encoding a full-length polypeptide or protein) and can also encompass partial gene sequences (e.g., a fragment of the gene sequence found in nature and/or a gene sequence encoding a protein or fragment of a polypeptide or protein). A gene can include modified gene sequences (e.g., modified as compared to the sequence found in nature). Thus, a gene is not limited to the natural or full-length gene sequence found in nature.

Polynucleotides can be purified free of other components, such as proteins, lipids and other polynucleotides. For example, the polynucleotide can be 50%, 75%, 90%, 95%, 96%, 97%, 98%, 99%, or 100% purified. A polynucleotide existing among hundreds to millions of other polynucleotide molecules within, for example, cDNA or genomic libraries, or gel slices containing a genomic DNA restriction digest are not to be considered a purified polynucleotide. Polynucleotides can encode the polypeptides described herein (e.g., an acetolactate synthase (AlsS) polypeptide, an acetolactate decarboxylase (AlsD) polypeptide, a malate dehydrogenase (Mdh3) polypeptide, a truncated malate dehydrogenase (tMdh3) polypeptide, a malic enzyme (Me1) polypeptide, a xylose reductase (Xyl1) polypeptide, a xylitol dehydrogenase (Xyl2) polypeptide, a xylulokinase (Xyl3) polypeptide, a (R,R)-butanediol dehydrogenase (Bdh1) polypeptide, a glyceraldehyde-3-phosphate dehydrogenase (Gpd1) polypeptide, a glyceraldehyde-3-phosphate dehydrogenase (Gpd2) polypeptide, a pyruvate decarboxylase (Pdc1) polypeptide, an alcohol dehydrogenase (Adh1) polypeptide, a 4-nitrophenylphosphatase (Pho13) polypeptide, a cytosolic aldehyde dehydrogenase (Ald6) polypeptide, a pyruvate decarboxylase (Pyc1) polypeptide, a pyruvate decarboxylase (Pyc2) polypeptide) and mutants or variants thereof.

Polynucleotides can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A.

Polynucleotides can be codon optimized for expression in yeast, such as Saccharomyces, e.g., Saccharomyces cerevisiae.

Polynucleotides can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. Polynucleotides can encode full-length polypeptides, polypeptide fragments, and variant or fusion polypeptides.

Degenerate polynucleotide sequences encoding polypeptides described herein, as well as homologous nucleotide sequences that are at least about 80, or about 85, 90, 91, 92, 93, 94, 95, 96, 97, 98, or 99% identical to polynucleotides described herein and the complements thereof are also polynucleotides. Degenerate nucleotide sequences are polynucleotides that encode a polypeptide described herein or fragments thereof, but differ in nucleic acid sequence from the wild-type polynucleotide sequence, due to the degeneracy of the genetic code. Complementary DNA (cDNA)

molecules, species homologs, and variants of polynucleotides that encode biologically functional polypeptides also are polynucleotides.

Polynucleotides can be obtained from nucleic acid sequences present in, for example, a microorganism such as a yeast or bacterium. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides can be, for example, acetolactate synthase (alsS), acetolactate decarboxylase (alsD), malate dehydrogenase (mdh3) (tmdh3), malic enzyme (ME1), xylose reductase (XYL1), xylitol dehydrogenase (XYL2), xylulokinase (XYL3), (R,R)-butanediol dehydrogenase (BDH1), glyceraldehyde-3-phosphate dehydrogenase (GPD1), glyceraldehyde-3-phosphate dehydrogenase (GPD2), pyruvate decarboxylase (PDC1), alcohol dehydrogenase (ADH1), 4-nitrophenylphosphatase (PHO13), cytosolic aldehyde dehydrogenase (ALD6), pyruvate decarboxylase (PYC1), pyruvate decarboxylase (PYC2), malate dehydrogenase (mdh3), truncated malate dehydrogenase (tmdh3), pyruvate decarboxylase (PYC1), and pyruvate decarboxylase (PYC2).

Polynucleotides can comprise coding sequences for naturally occurring polypeptides or can encode altered sequences that do not occur in nature.

Unless otherwise indicated, the term polynucleotide or gene includes reference to the specified sequence as well as the complementary sequence thereof. The expression products of genes or polynucleotides are often proteins, or polypeptides, but in non-protein coding genes such as rRNA genes or tRNA genes, the product is a functional RNA. The process of gene expression is used by all known life forms, i.e., eukaryotes (including multicellular organisms), prokaryotes (bacteria and archaea), and viruses, to generate the macromolecular machinery for life. Several steps in the gene expression process can be modulated, including the transcription, up-regulation, RNA splicing, translation, and post-translational modification of a protein.

Any process that deletes, reduces, or attenuates the expression of e.g., a Gpd1 polypeptide, a Gpd2 polypeptide, a Pdc1 polypeptide, an Adh1 polypeptide, a Pho13 polypeptide, or an Ald6 polypeptide can be used to make a microorganism described herein. Any process that adds or increases the expression of e.g., an AlsS polypeptide, an AlsD polypeptide, a Mdh3 polypeptide, a tMdh3 polypeptide, a Me1 polypeptide, a Bdh1 polypeptide, a Xyl1 polypeptide, a Xyl2 polypeptide, a Xyl3 polypeptide, a Pyc1 polypeptide, Pyc2 polypeptide, (R,R)-butanediol dehydrogenase (Bdh1) can be used to make a microorganism described herein.

Polypeptides

A polypeptide is a polymer of two or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

The term "polypeptides" can refer to one or more of one type of polypeptide (a set of polypeptides). "Polypeptides" can also refer to mixtures of two or more different types of polypeptides (a mixture of polypeptides). The terms "polypeptides" or "polypeptide" can each also mean "one or more polypeptides." As used herein, the term "polypeptide of interest" or "polypeptides of interest", "protein of interest", "proteins of interest" includes any or a plurality of any of, e.g., AlsS, AlsD, Mdh3, tMdh3, Me1, Bdh1, Xyl1, Xyl2, Xyl3, Gpd1, Gpd2, Pdc1, Adh1, Pho13, Ald6, Pyc1, Bhd1, Pyc2 and/or Pyc2 polypeptides or other polypeptides described herein.

A mutated protein or polypeptide comprises at least one deleted, inserted, and/or substituted amino acid, which can be accomplished via mutagenesis of polynucleotides encoding these amino acids. Mutagenesis includes well-known methods in the art, and includes, for example, site-directed mutagenesis by means of PCR or via oligonucleotide-mediated mutagenesis as described in Sambrook et al., Molecular Cloning—A Laboratory Manual, 2nd ed., Vol. 1-3 (1989).

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar will be sufficiently similar to the amino acid sequence of the polypeptides described herein. Such variants generally retain the functional activity of the polypeptides described herein. Variants include peptides that differ in amino acid sequence from the native and wild-type peptide, respectively, by way of one or more amino acid deletion(s), addition(s), and/or substitution(s). These may be naturally occurring variants as well as artificially designed ones.

The terms "sequence identity" or "percent identity" are used interchangeably herein. To determine the percent identity of two polypeptide molecules or two polynucleotide sequences, the sequences are aligned for optimal comparison purposes (e.g., gaps can be introduced in the sequence of a first polypeptide or polynucleotide for optimal alignment with a second polypeptide or polynucleotide sequence). The amino acids or nucleotides at corresponding amino acid or nucleotide positions are then compared. When a position in the first sequence is occupied by the same amino acid or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). In some embodiments the length of a reference sequence aligned for comparison purposes is at least 80% of the length of the comparison sequence, and in some embodiments is at least 90% or 100%. In an embodiment, the two sequences are the same length.

Ranges of desired degrees of sequence identity are approximately 70% to 100% and integer values in between. Percent identities between a disclosed sequence and a claimed sequence can be at least 70%, at least 80%, at least 83%, at least 85%, at least 90%, at least 95%, at least 98%, at least 99%, at least 99.5%, or at least 99.9%. In general, an exact match indicates 100% identity over the length of the reference sequence. Polypeptides and polynucleotides that are sufficiently similar to polypeptides (e.g., AlsS, AlsD, Mdh3, tMdh3, Me1, Bdh1, Xyl1, Xyl2, Xyl3, Gpd1, Gpd2, Pdc1, Adh1, Pho13, Ald6, Pyc1, Pyc2) and polynucleotides described herein (e.g., alsS, alsD, BDH1, mdh3, tmdh3, ME1, XYL1, XYL2, XYL3, GPD1, GPD2, PDC1, ADH1, PHO13, ALD6, PYC1, PYC2 polynucleotides) can be used herein. Polypeptides and polynucleotides that are about 70, 80, 85, 90, 91, 92, 93, 94 95, 96, 97, 98, 99 99.5% or more identical to polypeptides and polynucleotides described herein can also be used herein.

Polypeptides and polynucleotides that are about 70, 80, 85, 90, 95, 96, 97, 98, 99% or more identity to polypeptides (e.g., AlsS, AlsD, Mdh3, tMdh3, Me1, Bdh1, Xyl1, Xyl2, Xyl3, Gpd1, Gpd2, Pdc1, Adh1, Pho13, Ald6, Pyc1, Pyc2) and polynucleotides (e.g., alsS, alsD, mdh3, tmdh3, ME1, BDH1, XYL1, XYL2, XYL3, GPD1, GPD2, PDC1, ADH1, PHO13, ALD6, PYC1, PYC2 polynucleotides) described herein can also be used.

Constructs and Cassettes

A recombinant construct is a polynucleotide having heterologous polynucleotide elements. Recombinant constructs include expression cassettes or expression constructs, which refer to an assembly that is capable of directing the expression of a polynucleotide or gene of interest. An expression cassette generally includes regulatory elements such as a promoter that is operably linked to (so as to direct transcription of) a polynucleotide and often includes a polyadenylation sequence as well.

An "expression cassette" refers to a fragment of DNA comprising a coding sequence of a selected polynucleotide or gene (e.g., alsS, alsD, mdh3, tmdh3, ME1, BDH1, XYL1, XYL2, XYL3, GPD1, GPD2, PDC1, ADH1, PHO13, ALD6, PYC1, and/or PYC2 polynucleotides) and, optionally, regulatory elements preceding (5' non-coding sequences) and following (3' non-coding sequences) the coding sequence can be required for expression of the selected gene product. Thus, an expression cassette is typically composed of: 1) a promoter sequence; 2) a coding sequence ("ORF"); and optionally 3) a 3' untranslated region (i.e., a terminator). The expression cassette is usually included within a vector, to facilitate cloning and transformation. Different expression cassettes can be transformed into different organisms including bacteria, yeast, plants, and mammalian cells, as long as the correct regulatory elements are used for each host.

A recombinant construct or expression cassette can be contained within a vector. In addition to the components of the recombinant construct, the vector can include, one or more selectable markers, a signal which allows the vector to exist as single-stranded DNA (e.g., a M13 origin of replication), at least one multiple cloning site, and an origin of replication (e.g., a SV40 or adenovirus origin of replication).

Generally, a polynucleotide or gene that is introduced into a genetically engineered organism is part of a recombinant construct. A polynucleotide can comprise a gene of interest, e.g., a coding sequence for a protein, or can be a sequence that is capable of regulating expression of a gene, such as a regulatory element like a promoter, an antisense sequence, a sense suppression sequence, or a miRNA sequence. A recombinant construct can include, for example, regulatory elements operably linked 5' or 3' to a polynucleotide encoding one or more polypeptides of interest. For example, a promoter can be operably linked with a polynucleotide encoding one or more polypeptides of interest when it is capable of affecting the expression of the polynucleotide (i.e., the polynucleotide is under the transcriptional control of the promoter). Polynucleotides can be operably linked to regulatory elements in sense or antisense orientation. The expression cassettes or recombinant constructs can additionally contain a 5' leader polynucleotide. A leader polynucleotide can contain a promoter as well as an upstream region of a gene. The regulatory elements (i.e., promoters, enhancers, transcriptional regulatory regions, translational regulatory regions, and translational termination regions) and/or the polynucleotide encoding a signal anchor can be native/analogous to the host cell or to each other. Alternatively, the regulatory elements can be heterologous to the host cell or to each other. See, U.S. Pat. No. 7,205,453 and U.S. Patent Application Publication Nos. 2006/0218670 and 2006/0248616. The expression cassette or recombinant construct can additionally contain one or more selectable marker genes.

Methods for preparing polynucleotides operably linked to regulatory elements and expressing polypeptides in a host cell are well-known in the art. See, e.g., U.S. Pat. No. 4,366,246. A polynucleotide can be operably linked when it is positioned adjacent to or close to one or more regulatory elements, which direct transcription and/or translation of the polynucleotide.

A promoter is a nucleotide sequence that is capable of controlling the expression of a coding sequence or gene. Promoters are generally located 5' of the sequence that they regulate. Promoters may be derived in their entirety from a native gene, can be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell- or tissue-specific manner, in response to different environmental or physiological conditions, or in response to specific compounds. Promoters are typically classified into two classes: inducible and constitutive. A constitutive promoter refers to a promoter that allows for continual transcription of the coding sequence or gene under its control.

An inducible promoter refers to a promoter that initiates increased levels of transcription of the coding sequence or gene under its control in response to a stimulus or an exogenous environmental condition. If inducible, there are inducer polynucleotides present therein that mediate regulation of expression so that the associated polynucleotide is transcribed only when an inducer molecule is present. A directly inducible promoter refers to a regulatory region, wherein the regulatory region is operably linked to a gene encoding a protein or polypeptide, where, in the presence of an inducer of the regulatory region, the protein or polypeptide is expressed. An indirectly inducible promoter refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by inducible promoter.

A promoter can be any polynucleotide that shows transcriptional activity in the chosen host microorganism. A promoter can be naturally-occurring, can be composed of portions of various naturally-occurring promoters, or may be partially or totally synthetic. Guidance for the design of promoters is derived from studies of promoter structure, such as that of Harley and Reynolds, *Nucleic Acids Res.,* 15, 2343-61 (1987). In addition, the location of the promoter relative to the transcription start can be optimized. Many suitable promoters for use in microorganisms and yeast are well known in the art, as are polynucleotides that enhance expression of an associated expressible polynucleotide.

A selectable marker can provide a means to identify microorganisms that express a desired product. Selectable markers include, but are not limited to, ampicillin resistance for prokaryotes such as *E. coli*, neomycin phosphotransferase, which confers resistance to the aminoglycosides neomycin, kanamycin and paromycin (Herrera-Estrella, *EMBO J.* 2:987-995, (1983)); dihydrofolate reductase, which confers resistance to methotrexate (Reiss, *Plant Physiol. (Life Sci. Adv.*) 13:143-149, (1994)); trpB, which allows cells to utilize indole in place of tryptophan; hisD, which allows cells to utilize histinol in place of histidine (Hartman, *Proc. Natl. Acad. Sci., USA* 85:8047, (1988)); mannose-6-phosphate isomerase which allows cells to utilize mannose (WO 94/20627); hygro, which confers resistance to hygromycin (Marsh, *Gene* 32:481-485, (1984)); ornithine decarboxylase, which confers resistance to the ornithine decarboxylase inhibitor, 2-(difluoromethyl)-DL-ornithine (DFMO; McConlogue, In: *Current Communications in Molecular Biology*, Cold Spring Harbor Laboratory ed., (1987)); deaminase from *Aspergillus terreus*, which confers resistance to Blasticidin S (Tamura, *Biosci. Biotechnol. Biochem.* 59:2336-2338, (1995)); phosphinothricin acetyltransferase gene, which confers resistance to phosphinothricin (White et al., *Nucl. Acids Res.* 18:1062, (1990); Spencer et al., *Theor. Appl. Genet.* 79:625-633, (1990)); a mutant acetolactate synthase, which confers imidazolione or sulfonylurea resistance (Lee et al., *EMBO J.* 7:1241-1248, (1988)), a mutant EPSPV-synthase, which confers glyphosate resistance (Hinchee et al., *BioTechnology* 91:915-922, (1998)); a mutant psbA, which confers resistance to atrazine (Smeda et al., *Plant Physiol.* 103:911-917, (1993)), a mutant protoporphyrinogen oxidase (see U.S. Pat. No. 5,767,373), or other markers conferring resistance to an herbicide such as glufosinate.

A transcription termination region of a recombinant construct or expression cassette is a downstream regulatory region including a stop codon and optionally a transcription terminator sequence. Transcription termination regions that can be used can be homologous to the transcriptional initiation region, can be homologous to the polynucleotide encoding a polypeptide of interest, or can be heterologous (i.e., derived from another source). A transcription termination region or can be naturally occurring, or wholly or partially synthetic. 3' non-coding sequences encoding transcription termination regions may be provided in a recombinant construct or expression construct and may be from the 3' region of the gene from which the initiation region was obtained or from a different gene. A large number of termination regions are known and function satisfactorily in a variety of hosts when utilized in both the same and different genera and species from which they were derived. Termination regions may also be derived from various genes native to the preferred hosts. The termination region is usually selected more for convenience rather than for any particular property.

The procedures described herein employ, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., (1989); Sambrook and Russell, *Molecular Cloning*, 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, N Y (1992); Guthrie and Fink, *Guide to Yeast Genetics and Molecular Biology*, Academic Press, N Y (1991); Harlow and Lane, Antibodies, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology*, 6th Edition, Blackwell Scientific Publications, Oxford (1988); Fire, et al., *RNA Interference Technology From Basic Science to Drug Development*, Cambridge University Press, Cambridge (2005); Schepers, *RNA Interference in Practice*, Wiley-VCH (2005); Engelke, *RNA Interference (RNAi): The Nuts &Bolts of siRNA Technology*, DNA Press (2003); Gott, *RNA Interference, Editing, and Modification: Methods and Protocols (Methods in Molecular Biology)*, Human Press, Totowa, N.J. (2004); and Sohail, *Gene Silencing by RNA Interference: Technology and Application*, CRC (2004)).

Recombinant Yeast

A recombinant, transgenic, or genetically engineered yeast has been genetically modified from its native state. Thus, "recombinant yeast" or "recombinant yeast cell" refers to a yeast cell that has been genetically modified from the native state. A recombinant yeast cell can have, for example, nucleotide insertions, nucleotide deletions, nucleotide rearrangements, gene disruptions, recombinant polynucleotides, heterologous polynucleotides, deleted polynucleotides, nucleotide modifications, or combinations thereof introduced into its DNA. These genetic modifications can be present in the chromosome of the yeast, or on a plasmid in the yeast. Recombinant yeast cells disclosed herein can comprise exogenous polynucleotides on plasmids. Alternatively, recombinant cells can comprise exogenous polynucleotides stably incorporated into their chromosome.

A heterologous or exogenous polypeptide or polynucleotide refers to any polynucleotide or polypeptide that does not naturally occur or that is not present in the starting target yeast. For example, a polynucleotide from bacteria or yeast that is transformed into a yeast cell that does naturally or otherwise comprise the yeast polynucleotide is a heterologous or exogenous yeast. A heterologous or exogenous polypeptide or polynucleotide can be a wild-type, synthetic, or mutated polypeptide or polynucleotide. In an embodiment, a heterologous or exogenous polypeptide or polynucleotide is not naturally present in a starting target yeast and is from a different genus or species than the starting target yeast. In an aspect, a heterologous or exogenous polypeptide or polynucleotide is not naturally present in a starting target yeast and is from a bacterium.

A homologous or endogenous polypeptide or polynucleotide refers to any polynucleotide or polypeptide that naturally occurs or that is otherwise present in a starting target yeast. For example, a polynucleotide that is naturally present in a yeast is a homologous or endogenous polynucleotide. In an embodiment, a homologous or endogenous polypeptide or polynucleotide is naturally present in a starting target yeast.

A recombinant yeast can comprise one or more polynucleotides not present in a corresponding wild-type cell, wherein the polynucleotides have been introduced into that yeast using recombinant DNA techniques, or which polynucleotides are not present in a wild-type yeast and is the result of one or more mutations.

In an embodiment a genetically engineered or recombinant yeast comprises one or more heterologous or exogenous polynucleotides, optionally operably linked to one or more heterologous, exogenous, or endogenous regulatory elements such that one or more heterologous or exogenous biologically active polypeptides are expressed by the yeast.

The term "overexpression" or "overexpressed" as used herein refers to a level of enzyme or polypeptide expression that is greater than what is measured in a wild-type cell of the same species as the host cell that has not been genetically altered. The overexpression of the enzymes or polypeptides can be achieved by constructing inducible overexpression vectors encoding for the desired polypeptide. Strong promoters and strong constitutive promoters can be used to induce overexpression of a polypeptide as can the use of multiple copies of a polynucleotide in the recombinant microorganism. Overexpression is any expression level that is greater than wild-type expression. In an embodiment a Pyc1 polypeptide, a Pyc2 polypeptide, a Mdh3 polypeptide, a tMdh3 polypeptide, or combinations thereof can be overexpressed.

Yeast

In aspects a yeast of the genus *Saccharomyces*, e.g., *Saccharomyces cerevisiae*, is genetically engineered using any suitable technique. In some aspects one or more of alsS, alsD, mdh3, tmdh3, ME1, BDH1, XYL1, XYL2, XYL3, GPD1, GPD2, PDC1, ADH1, PHO13, ALD6, PYC1, PYC2 polynucleotides are deleted, rendered non-functional, overexpressed, or added to a yeast, such as *Saccharomyces*, e.g.,

US 12,600,992 B2

15 16

*Saccharomyces cerevisiae.* Other *Saccharomyces* species can be used such as *S. castellii, S. mikatae, S. cariocanus, S. boulardii, S. paracoxus,* and *S. kudriavzevii.* Other yeast that can be use include *Scheffersomyces* sp., e.g., *S. stipitis, Yarrowia* sp. such as *Y. lipolytica, Kluyveromyces* sp. such as *K. lactis, Dekkera* sp. such as *D. bruxellensis, Candida* sp., *Kloeckera* sp., *Hanseniaspora* sp., *Brettanomyces* sp., *Pichia* sp., and *Lanchacea* sp.

In an aspect, a recombinant yeast, *Saccharomyces,* e.g., *Saccharomyces cerevisiae,* comprises a deleted or non-functional GPD1 gene or polynucleotide. In an aspect, a recombinant yeast, *Saccharomyces,* e.g., *Saccharomyces cerevisiae,* comprises a deleted or non-functional GPD2 gene or polynucleotide. In an aspect, a recombinant yeast, *Saccharomyces,* e.g., *Saccharomyces cerevisiae,* comprises a deleted or non-functional PDC1 gene or polynucleotide. In an aspect, a recombinant yeast, *Saccharomyces,* e.g., *Saccharomyces cerevisiae,* comprises a deleted or non-functional ADH1 gene or polynucleotide. In an aspect, a recombinant yeast, *Saccharomyces,* e.g., *Saccharomyces cerevisiae,* comprises a deleted or non-functional PHO13 gene or polynucleotide. In an aspect, a recombinant yeast, *Saccharomyces,* e.g., *Saccharomyces cerevisiae,* comprises a deleted or non-functional ADH6 gene or polynucleotide.

In an aspect, a recombinant yeast, *Saccharomyces,* e.g., *Saccharomyces cerevisiae,* comprises a deleted or non-functional GPD1, GPD2, PDC1, and ADH1 gene or polynucleotide. Additionally, the recombinant yeast can additionally lack a PHO13, and/or ALD6 gene or polynucleotide. Alternatively, the recombinant yeast comprises a deleted or non-functional PHO13, and/or ALD6 gene or polynucleotide.

In an aspect, a recombinant yeast can comprise a recombinant yeast, e.g., *Saccharomyces* such as *S. cerevisiae,* comprising a recombinant nucleic acid molecule encoding AlsS. In an aspect, a recombinant yeast can comprise a recombinant yeast, e.g., *Saccharomyces* such as *S. cerevisiae,* comprising a recombinant nucleic acid molecule encoding AlsD. In an aspect, a recombinant yeast can comprise a recombinant yeast, e.g., *Saccharomyces* such as *S. cerevisiae,* comprising a recombinant nucleic acid molecule encoding Mdh3. In an aspect, a recombinant yeast can comprise a recombinant yeast, e.g., *Saccharomyces* such as *S. cerevisiae,* comprising a recombinant nucleic acid molecule encoding tMdh3. In an aspect, a recombinant yeast can comprise a recombinant yeast, e.g., *Saccharomyces* such as *S. cerevisiae,* comprising a recombinant nucleic acid molecule encoding Me1. In an aspect, a recombinant yeast can comprise a recombinant yeast, e.g., *Saccharomyces* such as *S. cerevisiae,* comprising a recombinant nucleic acid molecule encoding AlsS, AlsD, Mdh3 (and/or tMdh3), and Me1. In an aspect, a recombinant yeast can additionally comprise a recombinant nucleic acid molecule encoding Xyl1, Xyl2, and Xyl3. A recombinant yeast can additionally comprise a recombinant nucleic acid molecule encoding Bdh1.

In an aspect, a yeast culture can comprise a recombinant yeast, e.g., *Saccharomyces* such as *S. cerevisiae,* comprising recombinant nucleic acid molecules encoding alsS, alsD, mdh3, tmdh3, ME1, XYL1, XYL2, XYL3, BDH1. In an aspect, PYC1, PYC2, mdh3, tmdh3, BDH1 polynucleotides or genes are overexpressed.

Acetolactate Synthase (alsS) and Acetolactate Decarboxylase (alsD)

One or more acetolactate synthase (alsS) and acetolactate decarboxylase (alsD) polynucleotides can be genetically engineered into a target yeast, e.g., *Saccharomyces,* so that the yeast can express acetolactate synthase (AlsS) and acetolactate decarboxylase (AlsD). In an aspect, the genes encoding the proteins can be obtained from *Bacillus,* e.g., *B. subtilis* or other suitable organism.

An alsS gene can encode a polypeptide as shown in UniProtQ04789:

```
                                                          SEQ ID NO: 70

MTKATKEQKS  LVKNRGAELV  VDCLVEQGVT  HVFGIPGAKI  DAVEDALQDK  GPEIIVARHE

QNAAFMAQAV  GRLTGKPGVV  LVTSGPGASN  LATGLLTANT  EGDPVVALAG  NVIRADRLKR

THQSLDNAAL  FQPITKYSVE  VQDVKNIPEA  VINAFRIASA  GQAGAAFVSF  PQDVVNEVIN

TKNVRAVAAP  KLGPAADDAI  SAAIAKIQTA  KLPVVLVGMK  GGRPEAIKAV  RKLLKKVQLP

FVETYQAAGT  LSRDLEDQYF  GRIGLERNQP  GDLLLEQADV  VLTIGYDPIE  YDPKFWNING

DRTIIHLDEI  IADIDHAYQP  DLELIGDIPS  TINHIEHDAV  KVEFAEREQK  ILSDLKQYMH

EGEQVPADWK  SDRAHPLEIV  KELRNAVDDH  VTVTCDIGSH  AIWMSRYFRS  YEPLTLMISN

GMQTLGVALP  WAIGASLVKP  GEKVVSVSGD  GGFLESAMEL  ETAVRLKAPI  VHIVWNDSTY

DMVAFQQLKK  YNRTSAVDFG  NIDIVKYAES  FGATGLRVES  PDQLADVLRQ  GMNAEGPVII

DVPVDYSDNI  NLASDKLPKE  FGELMKTKAL
```

In an aspect an alsS polynucleotide can encode a poly-peptide having 70, 75, 80, 85, 90, 95, 96, 97, 98, 99% or more sequence identity to SEQ ID NO:70. In other aspects an alsS gene can encode AlsS polypeptides comprising 70, 75, 80, 85, 90, 95, 96, 97, 98, 99% or more sequence identity to AlsS polypeptides from *B. subtilis* (e.g., GenBank Accession numbers WP_251188357, WP_251188357.1, WP_047183300.1, WP_064816095.1, ARV46326.1) or other *Bacillus* species (e.g., *B. inaquosorum* (WP_268286106.1 and WP_268353708.1); *B. vallismortis* (WP_268529903.1 and WP_010328836.1), *B. tequilensis* (WP_024714271.1 and WP_174227748.1), *B. halotolerans* (UQZ47588.1), *B. atrophaeus* (WP_268477846.1 and WP_219946724.1), *B. velezensis* (WP_182274688.1 and WP_277507204.1), *B. amyloliquefaciens* (WP_151140090.1) or other suitable organism.

An alsD gene can encode a polypeptide as shown in UniProt Q04777:

```
                                                    SEQ ID NO: 71
MKRESNIQVL SRGQKDQPVS QIYQVSTMTS LLDGVYDGDF ELSEIPKYGD FGIGTENKLD

GELIGEDGEF YRLRSDGTAT PVQNGDRSPF CSFTFFTPDM THKIDAKMTR EDFEKEINSM

LPSRNLFYAI RIDGLFKKVQ TRTVELQEKP YVPMVEAVKT QPIFNEDNVR GTIVGELTPA

YANGIAVSGY HLHEIDEGRN SGGHVEDYVL EDCTVTISQK MNMNLRLPNT ADFFNANLDN

PDFAKDIETT EGSPE
```

In an aspect an alsD polynucleotide can encode a poly-peptide having 70, 75, 80, 85, 90, 95, 96, 97, 98, 99% or more sequence identity to SEQ ID NO:71. In other aspects an alsD gene can encode AlsD polypeptides comprising 70, 75, 80, 85, 90, 95, 96, 97, 98, 99% or more sequence identity to AlsD polypeptides from *B. subtilis* (e.g., GenBank Accession Number WP_283933836.1, WP_129134081.1, WP_232920039.1 and WP_136653839.1) or other *Bacillus* species (e.g., *B. spizizenii* (MCY7828602.1), *B. cabrialesii* (WP_129507389.1), *B. halotolerans* (WP_059353667.1), *B. mojavensis* (WP_268471631.1), *B. tequilensis* (WP_167873487.1), *B. atrophaeus* (WP_061669143), *B. nakamurai* (WP_061522606.1), *B. amyloliquefaciens* (WP_071347481.1), *B. velezensis* (WP_265624765.1)) or other suitable organism).

Malate Dehydrogenase (Mdh3)

One or more malate dehydrogenase (mdh3) polynucle-otides can be genetically engineered into a target yeast, e.g., *Saccharomyces*, so that the yeast can express malate dehy-drogenase (Mdh3). In an aspect, the genes encoding the proteins can be obtained from *Saccharomyces*, such as *S. cerevisiae* or other suitable organism. A mdh3 gene can encode a polypeptide as shown in UniProt P32419:

```
                                                    SEQ ID NO: 72
MVKVAILGAS GGVGQPLSLL LKLSPYVSEL ALYDIRAAEG IGKDLSHINT NSSCVGYDKD

SIENTLSNAQ VVLIPAGVPR KPGLTRDDLF KMNAGIVKSL VTAVGKFAPN ARILVISNPV

NSLVPIAVET LKKMGKFKPG NVMGVTNLDL VRAETFLVDY LMLKNPKIGQ EQDKTTMHRK

VTVIGGHSGE TIIPIITDKS LVFQLDKQYE HFIHRVQFGG DEIVKAKQGA GSATLSMAFA

GAKFAEEVLR SFHNEKPETE SLSAFVYLPG LKNGKKAQQL VGDNSIEYFS LPIVLRNGSV

VSIDTSVLEK LSPREEQLVN TAVKELRKNI EKGKSFILDS SKL
```

In an aspect the last three amino acids are deleted to make tMdh3 (SEQ ID NO:62). In an aspect an mdh3 or tmdh3 polynucleotide can encode a polypeptide having 70, 75, 80, 85, 90, 95, 96, 97, 98, 99% or more sequence identity to SEQ ID NO:72 or SEQ ID NO:62. In other aspects an mdh3 or tmdh3 gene can encode Mdh3 or tMdh polypeptides comprising 70, 75, 80, 85, 90, 95, 96, 97, 98, 99% or more sequence identity to Mdh3 polypeptides from *S. cerevisiae* (e.g., CA14819955 or EGA62752.1) or other *Saccharomyces* species (e.g., *S. paradoxus* (XP_033765191.1), *S. mikatae* (XP_056080942.1), *S. kudriavzevii* ((EHN03309.1), *S. arboricola* (EJS44372.1)) or other suitable organism. The tMdh3 polypeptides will have the last 3 amino acids deleted before comparison to these or other Mdh3 sequences.

Malic Enzyme

One or more malic enzyme (ME1) polynucleotides can be genetically engineered into a target yeast, e.g., *Saccharomyces*, so that the yeast can express malic enzyme (Me1). In an aspect, an ME1 polynucleotide comprises SEQ ID NO:66 or SEQ ID NO:67. In an aspect, an ME1 polynucleotide comprises 70, 75, 80, 85, 90, 95, 96, 97, 98, 99% or more sequence identity to SEQ ID NO:66 and SEQ ID NO:67. In an aspect, the genes encoding the protein can be obtained from Rhodosporidium, e.g., Rhodosporidium toruloides or other suitable organism.

An ME1 gene can encode a polypeptide as shown in UniProt A0A191UMV6

```
                                                         SEQ ID NO: 73
MPSTFAPSQP LQGGPSPSQL GPKELLIERA LTRLRSIPSD LEKYTFLAGL RCRNPDVFYG

LVGGNMKECC PIIYTPVIGL ACQNWSLIHP PPPESDPTIE ALYLSYSDLP NLPSLIKGLK

TRLPHNQMQI SVVTDGSRVL GLGDLGVGGM GISQGKLSLY VAAGGVNPKA TLPIAIDFGT

DNEKLLADPL YVGQRMRRLS EEKCLEFMDV FMRCMHETFP NMVIQHEDWQ TPLAFPLLHK

NRDLYPCEND DIQGTGAVVL AGAIRAFHLN GVALKDQKIL FFGAGSSGVG VAETICKYFE

LQGMSEQEAK SKFWLVDSKG LVAHNRGDTL PSHKKYLARS EPDAPKLRSL KEVVEHVQPT

ALLGLSTVGG TFTKEILESM ATYNKRPIVF ALSNPVAQAE CTFEEAIEGT DGRVLYASGS

PFDPVEYKEK RYEPGQGNNM YIFPGLGIGA ILARVSKIPE ELVHASAQGL ADSLTPEETA

RHLLYPDIER IREVSIKIAV TVIQAAQKLG VDRNEELRGK SSAEIEAYVR KGMYHPLLEA

EQQAQ
```

In an aspect an ME1 polynucleotide can encode a polypeptide having 70, 75, 80, 85, 90, 95, 96, 97, 98, 99% or more sequence identity to SEQ ID NO:73. In other aspects an ME1 gene can encode Me1 polypeptides comprising 80, 85, 90, 95, 96, 97, 98, 99% or more sequence identity to Me1 polypeptides from Rhodosporidium toruloides (e.g., GenBank Accession numbers KAJ8292376.1, XP_016271116.1, GEM12284.1 or KAJ8292375.1) or other Rhodosporidium species (e.g., *R. mucilaginosa* (KAG0653902.1) or other suitable organism.

Xylose Reductase

In an aspect, a recombinant yeast can ferment xylose. Where a yeast cannot ferment xylose or it desired that a yeast ferment xylose at a better rate, then one more recombinant nucleic acid molecules encoding one or more of Xly1, Xly2, and/or Xyl3 can be added to a yeast.

One or more xylose reductase (XYL1) polynucleotides can be genetically engineered into a target yeast, e.g., *Saccharomyces*, so that the yeast can express xylose reductase (Xyl1). In an aspect, the genes encoding the protein can be obtained from *Scheffersomyces*, e.g., *Scheffersomyces stipitis* or other suitable organism.

An XYL1 gene can encode a polypeptide as shown in UniProt P31867

```
                                                         SEQ ID NO: 74
MPSIKLNSGY DMPAVGFGCW KVDVDTCSEQ IYRAIKTGYR LEDGAEDYAN EKLVGAGVKK

AIDEGIVKRE DLFLTSKLWN NYHHPDNVEK ALNRTLSDLQ VDYVDLFLIH FPVTFKFVPL

EEKYPPGFYC GKGDNEDYED VPILETWKAL EKLVKAGKIR SIGVSNFPGA LLLDLLRGAT
```

-continued

```
IKPSVLQVEH HPYLQQPRLI EFAQSRGIAV TAYSSFGPQS FVELNQGRAL NTSPLFENET

IKAIAAKHGK SPAQVLLRWS SQRGIAIIPK SNTVPRLLEN KDVNSFDLDE QDFADIAKLD

INLRENDPWD WDKIPIFV
```

In an aspect an XYL1 polynucleotide can encode a polypeptide having 65, 70, 75, 80, 85, 90, 95, 96, 97, 98, 99% or more sequence identity to SEQ ID NO:74. In other aspects an XYL1 gene can encode Xyl1 polypeptides comprising 65, 70, 75, 80, 85, 90, 95, 96, 97, 98, 99% or more sequence identity to Xyl1 polypeptides from *Scheffersomyces stipitis* (e.g., GenBank Accession numbers 5Z6T_A or XP_001385181.1) or other *Scheffersomyces* species (e.g., *S. shehatae* (Q9P430.1), or other suitable organism (e.g., *Yamadazyma tenuis* (074237.1) or *Spathaspora roraimensis* (ALP00842.1)).

Xylitol Dehydrogenase

One or more xylitol dehydrogenase (XYL2) polynucleotides can be genetically engineered into a target yeast, e.g., *Saccharomyces*, so that the yeast can express xylitol dehydrogenase (Xyl2). In an aspect, the genes encoding the protein can be obtained from *Scheffersomyces*, e.g., *Scheffersomyces stipitis* or other suitable organism.

An XYL2 gene can encode a polypeptide as shown in UniProt P22144

```
                                                            SEQ ID NO: 75

MTANPSLVLN KIDDISFETY DAPEISEPTD VLVQVKKTGI CGSDIHFYAH GRIGNFVLTK

PMVLGHESAG TVVQVGKGVT SLKVGDNVAI EPGIPSRESD EYKSGHYNLC PHMAFAATPN

SKEGEPNPPG TLCKYFKSPE DFLVKLPDHV SLELGALVEP LSVGVHASKL GSVAFGDYVA

VEGAGPVGLL AAAVAKTEGA KGVIVVDIED NKLKMAKDIG AATHTENSKT GGSEELIKAF

GGNVPNVVLE CTGAEPCIKL GVDAIAPGGR FVQVGNAAGP VSFPITVEAM KELTLEGSER

YGENDYKTAV GIFDTNYQNG RENAPIDFEQ LITHRYKFKD AIEAYDLVRA GKGAVKCLID

GPE
```

In an aspect an XYL2 polynucleotide can encode a polypeptide having 65, 70, 75, 80, 85, 90, 95, 96, 97, 98, 99% or more sequence identity to SEQ ID NO:75. In other aspects an XYL2 gene can encode Xyl2 polypeptides comprising 65, 70, 75, 80, 85, 90, 95, 96, 97, 98, 99% or more sequence identity to Xyl2 polypeptides from *Scheffersomyces stipitis* (e.g., GenBank Accession numbers 7Y9P_A or XP_001386982.1) or other *Scheffersomyces* species (e.g., *S. shehatae* (AC101079.1), or other suitable organism (e.g., *Spathaspora passalidarum* (XP_007373266.1), *Spathaspora girioi* (ANG59282.1), or *Suhomyces tanzawaensis* (XP_020064684.1)).

Xylulokinase

One or more xylulokinase (XYL3) polynucleotides can be genetically engineered into a target yeast, e.g., *Saccharomyces*, so that the yeast can express xylulokinase (Xyl3). In an aspect, the genes encoding the protein can be obtained from *Scheffersomyces*, e.g., *Scheffersomyces stipitis* or other suitable organism.

An XYL3 gene can encode a polypeptide as shown in UniProt Q9P938

```
                                                            SEQ ID NO: 76

MTANPSLVLN KIDDISFETY DAPEISEPTD VLVQVKKTGI CGSDIHFYAH GRIGNEVLTK

MTTTPEDAPD KLFLGFDLST QQLKIIVTDE NLAALKTYNV EFDSINSSVQ KGVIAINDEI

SKGAIISPVY MWLDALDHVF EDMKKDGEPF NKVVGISGSC QQHGSVYWSR TAEKVLSELD

AESSLSSQMR SAFTEKHAPN WQDHSTGKEL EEFERVIGAD ALADISGSRA HYRETGLQIR

KLSTREKPEK YNRTARISLV SSFVASVLLG RITSIEEADA CGMNLYDIEK REFNEELLAI

AAGVHPELDG VEQDGEIYRA GINELKRKLG PVKPITYESE GDIASYFVTR YGENPDCKIY

SFTGDNLATI ISLPLAPNDA LISLGTSTTV LIITKNYAPS SQYHLFKHPT MPDHYMGMIC
```

```
                              -continued
YCNGSLAREK VRDEVNEKEN VEDKKSWDKF NEILDKSTDE NNKLGIYFPL GEIVPNAAAQ

IKRSVLNSKN EIVDVELGDK NWQPEDDVSS IVESQTLSCR LRTGPMLSKS GDSSASSSAS

PQPEGDGTDL HKVYQDLVKK FGDLFTDGKK QTFESLTARP NRCYYVGGAS NNGSIIXKMG

SILAPVNGNY KVDIPNACAL GGAYKASWSY ECEAKKEWIG YDQYINRLFE VSDEMNSFEV

KDKWLEYANG VGMLAKMESE LKH
```

In an aspect an XYL3 polynucleotide can encode a polypeptide having 65, 70, 75, 80, 85, 90, 95, 96, 97, 98, 99% or more sequence identity to SEQ ID NO:76. In other aspects an XYL3 gene can encode Xyl3 polypeptides comprising 65, 70, 75, 80, 85, 90, 95, 96, 97, 98, 99% or more sequence identity to Xyl3 polypeptides from *Scheffersomyces stipitis* (e.g., GenBank Accession numbers AAF72328.2, XP_001387325.2, KAG2731686.1) or other suitable organism (e.g., *Spathaspora hagerdaliae* (ANG59283.1), *Suhomyces tanzawaensis* (XP_020063646.1), or *Spathaspora gorwiae* (ANG59284.1)).

Butanediol Dehydrogenase (BDH1)

One or more butanediol dehydrogenase (BDH1) polynucleotides can be genetically engineered into a target yeast, e.g., *Saccharomyces*, so that the yeast can express butanediol dehydrogenase (Bdh1). In an aspect, the genes encoding the protein can be obtained from *Saccharomyces*, e.g., *Saccharomyces cerevisiae* or other suitable organism.

A BDH1 gene can encode a polypeptide as shown in UniProt P39714

```
                                                     SEQ ID NO: 77
MRALAYFKKG DIHFTNDIPR PEIQTDDEVI IDVSWCGICG SDLHEYLDGP IFMPKDGECH

KLSNAALPLA MGHEMSGIVS KVGPKVTKVK VGDHVVVDAA SSCADLHCWP HSKFYNSKPC

DACQRGSENL CTHAGFVGLG VISGGFAEQV VVSQHHIIPV PKEIPLDVAA LVEPLSVTWH

AVKISGEKKG SSALVLGAGP IGLCTILVLK GMGASKIVVS EIAERRIEMA KKLGVEVENP

SKHGHKSIEI LRGLTKSHDG FDYSYDCSGI QVTFETSLKA LTFKGTATNI AVWGPKPVPF

QPMDVTLQEK VMTGSIGYVV EDFEEVVRAI HNGDIAMEDC KQLITGKQRI EDGWEKGFQE

LMDHKESNVK ILLTPNNHGE MK
```

In an aspect a BHD1 polynucleotide can encode a polypeptide having 65, 70, 75, 80, 85, 90, 95, 96, 97, 98, 99% or more sequence identity to SEQ ID NO:77. In other aspects a BHD1 gene can encode Bhd1 polypeptides comprising 65, 70, 75, 80, 85, 90, 95, 96, 97, 98, 99% or more sequence identity to Bhd1 polypeptides from *Saccharomyces cerevisiae* (e.g., GenBank Accession numbers AJ093650.1, GMC37225.1, AJ094666.1, AJ095455.1) or other *Saccharomyces* species (e.g., *S. paradoxus* (XP_033764415.1), *S. mikatae* (XP_056080173.1), *S. kudriavzevii* (XP_056085817.1), *S. uvarum* (CA14055538.1, WBF10789.1), *S. eubayanus* (XP_018224053.1) or other suitable organism.

Deleted or Non-Functional Polynucleotides

In several aspects the yeast described herein have has one or more of a deleted or non-functional GPD1, GPD2, PDC1, ADH1, PHO13, and/or ALD6 gene. Deleted, non-functional, or eliminated gene or polynucleotide expression can be gene or polynucleotide expression that is eliminated or reduced to an amount that is insignificant or undetectable. Deleted, non-functional, or eliminated gene or polynucleotide expression can also be gene or polynucleotide expression that results in an RNA or protein that is nonfunctional, for example, deleted gene or polynucleotide expression can be gene or polynucleotide expression that results in a truncated RNA and/or polypeptide that has substantially no biological activity.

In an embodiment, a genetically engineered or recombinant yeast has no expression of a polynucleotide encoding one or more of Gpd1, Gpd2, Pdc1, Adh1, Pho13, Ald6 or combinations are present in the yeast. In an aspect, a genetically engineered or recombinant yeast has 50, 60, 70, 80, 90, 95, 99% or less expression of a polynucleotide encoding Gpd1, Gpd2, Pdc1, Adh1, Pho13, Ald6, or combinations thereof as compared to a wild-type yeast.

The lack of expression can be caused by at least one gene disruption or mutation of a GPD1, GPD2, PDC1, ADH1, PHO13, ALD6 gene or combinations thereof, which results in no expression of the GPD1, GPD2, PDC1, ADH1, PHO13, ALD6 gene or combinations thereof. For example, the lack of expression can be caused by a gene disruption in a GPD1, GPD2, PDC1, ADH1, PHO13, ALD6 gene or combinations thereof which results in attenuated or eliminated expression of the GPD1, GPD2, PDC1, ADH1, PHO13, ALD6 genes or combinations thereof such that the genes can be transcribed but not translated, or the genes can be transcribed and translated, but the resulting Gpd1, Gpd2, Pdc1, Adh1, Pho13, Ald6 polypeptides or combinations thereof, have substantially no biological activity.

In an embodiment, a recombinant microorganism is mutated or otherwise genetically altered such that there is substantially no expression of Gpd1, Gpd2, Pdc1, Adh1, Pho13, Ald6 polypeptides in the yeast. In an embodiment, a recombinant yeast is mutated or otherwise genetically altered such that there is substantially no expression of Gpd1, Gpd2, Pdc1, Adh1, Pho13, Ald6 polypeptides thereof in the cell.

In an aspect, a genetically engineered or recombinant yeast has 50, 60, 70, 80, 90, 95, 99% or less expression of a Gpd1, Gpd2, Pdc1, Adh1, Pho13, Ald6 polypeptide, or combinations thereof as compared to a wild-type microorganism.

The polynucleotides encoding a Gpd1, Gpd2, Pdc1, Adh1, Pho13, Ald6 polypeptide or combinations thereof can be deleted or mutated using any suitable genetic manipulation technique selected from, for example, TALEN, Zinc Finger Nucleases, and CRISPR-Cas9.

One or more regulatory elements controlling expression of the polynucleotides encoding a Gpd1, Gpd2, Pdc1, Adh1, Pho13, Ald6 polypeptide, or combinations thereof can be mutated or replaced to prevent or attenuate expression of a Gpd1, Gpd2, Pdc1, Adh1, Pho13, Ald6 polypeptide or combinations thereof, as compared to a control or wild-type yeast. For example, a promoter can be mutated or replaced such that the gene expression or polypeptide expression is attenuated or such that one or more of GPD1, GPD2, PDC1, ADH1, PHO13, ALD6 genes are not transcribed. In one embodiment, one or more promoters for a GPD1, GPD2, PDC1, ADH1, PHO13, ALD6 gene or combinations thereof are replaced with a promoter that has weaker activity than the wild-type promoter. A promoter with weaker activity transcribes the polynucleotide at a rate about 5, 10, 20, 30, 40, 50, 60, 70, 80, or 90% less than the wild-type promoter for that polynucleotide. In another embodiment, one or more promoters for GPD1, GPD2, PDC1, ADH1, PHO13, ALD6 genes or combinations thereof are replaced with an inducible promoter (e.g., TetO promoters such as TetO3, TetO7, and CUP1p; $P_{GAL1}$, $P_{GAL10}$, and $P_{GAL7}$) that can be controlled to attenuate expression of the GPD1, GPD2, PDC1, ADH1, PHO13, ALD6 gene or combinations thereof.

The reduced expression, non-expression, or expression of mutated, inactive, or reduced activity polypeptides can be affected by deletion of the polynucleotide or gene encoding Gpd1, Gpd2, Pdc1, Adh1, Pho13, and/or Ald6 polypeptide, replacement of the wild-type polynucleotide or gene with mutated forms, deletion of a portion of a GPD1, GPD2, PDC1, ADH1, PHO13, ALD6 genes or combinations thereof to cause expression of an inactive form of the polypeptides, or manipulation of the regulatory elements (e.g. promoter) to prevent or reduce expression of wild-type Gpd1, Gpd2, Pdc1, Adh1, Pho13, and/or Ald6 polypeptides. The promoter could also be replaced with a weaker promoter or an inducible promoter that leads to reduced expression of the polypeptides. Any method of genetic manipulation that leads to a lack of, or reduced expression and/or activity of Gpd1, Gpd2, Pdc1, Adh1, Pho13, and/or Ald6 polypeptides and can be used, including expression of inhibitor RNAs (e.g. shRNA, siRNA, and the like).

Wild-type refers to a yeast that is naturally occurring or which has not been recombinantly modified. A control yeast is a yeast that lacks genetic modifications of a test yeast and that can be used to test altered biological activity of genetically modified yeast.

A gene disruption is a genetic alteration in a polynucleotide or gene that renders an encoded gene product (e.g., Gpd1, Gpd2, Pdc1, Adh1, Pho13, and/or Ald6 polypeptide) inactive or attenuated (e.g., produced at a lower amount, e.g. about 50, 60, 70, 80, 90, 95, 99% or more lower amount as compared to wild-type or having lower biological activity e.g. about 50, 60, 70, 80, 90, 95, 99% or more lower biological activity as compared to wild-type). A gene disruption can include a disruption in a polynucleotide or gene that results in no expression of an encoded gene product, reduced expression of an encoded gene product, or expression of a gene product with reduced or attenuated biological activity. The genetic alteration can be, for example, deletion of the entire gene or polynucleotide, deletion of a regulatory element required for transcription or translation of the polynucleotide or gene, deletion of a regulatory element required for transcription or translation or the polynucleotide or gene, addition of a different regulatory element required for transcription or translation or the gene or polynucleotide, deletion of a portion (e.g. 1, 2, 3, 6, 9, 21, 30, 60, 90, 120 or more nucleic acids) of the gene or polynucleotide, which results in an inactive or partially active gene product, replacement of a gene's promoter with a weaker promoter, replacement or insertion of one or more amino acids of the encoded protein to reduce its activity, stability, or concentration, or inactivation of a gene's transactivating factor such as a regulatory protein. A gene disruption can include a null mutation, which is a mutation within a gene or a region containing a gene that results in the gene not being transcribed into RNA and/or translated into a functional gene product. An inactive gene product has no biological activity.

Zinc-finger nucleases (ZFNs), Talens, and CRISPR-Cas9 allow double strand DNA cleavage at specific sites in yeast chromosomes such that targeted gene insertion or deletion can be performed (Shukla et al., 2009, Nature 459:437-441; Townsend et al., 2009, Nature 459:442-445). This approach can be used to modify the promoter of endogenous genes or the endogenous genes themselves to modify expression of Gpd1, Gpd2, Pdc1, Adh1, Pho13, and/or Ald6 polypeptides, which can be present in the yeast genome. ZFNs, Talens or CRISPR/Cas9 can be used to change the sequences regulating the expression of the polypeptides to increase or decrease the expression or alter the timing of expression beyond that found in a non-engineered or wild-type yeast, or to delete the wild-type polynucleotide, or replace it with a deleted or mutated form to alter the expression and/or activity of Gpd1, Gpd2, Pdc1, Adh1, Pho13, and/or Ald6 polypeptide.

Yeast Cultures for Production of 2,3-BDO

In an aspect a yeast culture comprising two or more of the recombinant yeast described herein is provided. For example, a yeast culture can comprise a recombinant yeast, e.g., Saccharomyces such as S. cerevisiae, comprising one or more of a deleted or non-functional GPD1, GPD2, PDC1, ADH1, PHO13, and/or ALD6 gene or polynucleotide. In an aspect, a yeast culture can comprise a recombinant yeast, e.g., Saccharomyces such as S. cerevisiae, comprising one or more of recombinant nucleic acid molecules encoding alsS, alsD, mdh3, tmdh3, ME1, XYL1, XYL2, XYL3, and/or BDH1. In an aspect, one or more of PYC1, PYC2, mdh3, tmdh3, and/or BDH1 polynucleotides or genes are overexpressed.

A yeast, e.g., Saccharomyces can comprise a deleted or non-functional GPD1 polynucleotide or gene such that glyceraldehyde-3-phosphate dehydrogenase (Gpd1) is produced at a lower rate than a wild-type yeast having a functional GPD1 gene. In an aspect Gpd1 is produced or expressed at a rate or amount 20, 30, 40, 50, 60, 70 80, 90, 95, 99% less than a wild-type yeast having a functional GPD1 gene.

A yeast, e.g., *Saccharomyces* can comprise a deleted or non-functional GPD2 polynucleotide or gene such that glyceraldehyde-3-phosphate dehydrogenase (Gpd2) is produced at a lower rate than a wild-type yeast having a functional GPD2 gene. In an aspect Gpd2 is produced or expressed at a rate or amount 20, 30, 40, 50, 60, 70 80, 90, 95, 99% less than a wild-type yeast having a functional GPD2 gene.

A yeast, e.g., *Saccharomyces* can comprise a deleted or non-functional PDC1 polynucleotide or gene such that pyruvate decarboxylase (Pdc1) is produced at a lower rate than a wild-type yeast having a functional PDC1 gene. In an aspect Pdc1 is produced or expressed at a rate or amount 20, 30, 40, 50, 60, 70 80, 90, 95, 99% less than a wild-type yeast having a functional PDC1 gene.

A yeast, e.g., *Saccharomyces* can comprise a deleted or non-functional PDC2 polynucleotide or gene such that pyruvate decarboxylase (Pdc2) is produced at a lower rate than a wild-type yeast having a functional PDC2 gene. In an aspect Pdc2 is produced or expressed at a rate or amount 20, 30, 40, 50, 60, 70 80, 90, 95, 99% less than a wild-type yeast having a functional PDC1 gene.

A yeast, e.g., *Saccharomyces* can comprise a deleted or non-functional ADH1 polynucleotide or gene such that alcohol dehydrogenase (Adh1) is produced at a lower rate than a wild-type yeast having a functional ADH1 gene. In an aspect Adh1 is produced or expressed at a rate or amount 20, 30, 40, 50, 60, 70 80, 90, 95, 99% less than a wild-type yeast having a functional ADH1 gene.

A yeast, e.g., *Saccharomyces* can comprise a deleted or non-functional PHO13 polynucleotide or gene such that 4-nitrophenylphosphatase (Pho13) is produced at a lower rate than a wild-type yeast having a functional PHO13 gene. In an aspect Pho13 is produced or expressed at a rate or amount 20, 30, 40, 50, 60, 70 80, 90, 95, 99% less than a wild-type yeast having a functional PHO13 gene.

A yeast, e.g., *Saccharomyces* can comprise a deleted or non-functional ALD6 polynucleotide or gene such that cytosolic aldehyde dehydrogenase (Ald6) is produced at a lower rate than a wild-type yeast having a functional ALD6 gene. In an aspect Ald6 is produced or expressed at a rate or amount 20, 30, 40, 50, 60, 70 80, 90, 95, 99% less than a wild-type yeast having a functional ALD6 gene.

A recombinant yeast, e.g., *Saccharomyces* can comprise additional copies (e.g., 1, 2, 3 or more) of a polynucleotide encoding pyruvate decarboxylase (Pyc1), pyruvate decarboxylase (Pyc), malate dehydrogenase (Mdh3) (tMdh3), and/or butanediol dehydrogenase (Bdh1), which can be on a plasmid or integrated into the chromosome and overexpressed using a strong promoter, e.g., a strong constitutive promoter. A promoter can be operably linked to the polynucleotide or gene to be expressed. A strong promoter can be a $P_{TEF1}$ promoter (Translational elongation factor EF-1 alpha promoter) or a $P_{PGK1}$ promoter (3-phosphoglycerate kinase promoter). Other strong yeast promoters include, for example, $P_{ADH2}$, $P_{TEF2}$, $P_{SSA1}$, $P_{TDH3}$, $P_{PGK1}$, $P_{TPI1}$, $P_{CCW12}$, and $P_{ENO2}$, $P_{GAL1}$, $P_{GAL2}$, $P_{GAL7}$ and $P_{GAL10}$. Other suitable promoters are provided in Tang et al., Promoter Architecture and Promoter Engineering in *Saccharomyces cerevisiae*. Metabolites. 2020 Aug. 6; 10(8):320, which is incorporated by reference herein in its entirety.

These polynucleotides can be codon optimized and/or inserted into the chromosome by replacing a gene.

In an aspect, a recombinant yeast, e.g., *Saccharomyces* can overexpress one or more polypeptides such as pyruvate decarboxylase (Pyc1), pyruvate decarboxylase (Pyc), malate dehydrogenase (Mdh3) (tMdh3), and/or butanediol dehydrogenase (Bdh1), using a strong promoter, e.g., a strong constitutive promoter. In an aspect a mdh3 or tmdh3 gene is operably linked to a strong $P_{TDH3}$ promoter.

Methods of Production of 2,3-BDO

Methods of producing 2,3-butanediol (2,3-BDO) are provided herein. Any of the recombinant yeast described herein can be contacted a substrate. The recombinant yeast are allowed to ferment the substrate and 2,3-BDO collected from the fermentation broth. The yeast cultures and substrates can be fermented using a fed-batch process, a batch process, or any other suitable process.

A substrate can be lignocellulosic or cellulosic feedstock. Lignocellulosic and cellulosic feedstocks include crop residues like corn stover, wood residues (e.g., logging residues and forest thinning), dedicated energy crops (e.g., switchgrass, miscanthus, energy cane, sweet sorghum, high biomass sorghum, hybrid poplars, and shrub willows), algae, and industrial and other wastes (e.g., the non-recyclable organic portion of municipal solid waste, biosolids, sludges, waste food, plastics, $CO_2$, industrial waste gases, and manure slurries). These feedstocks are composed of cellulose, hemicellulose, and lignin.

A substrate can comprise glycose, xylose, or a combination of glucose and xylose.

In an aspect substantially no glycerol and/or substantially no ethanol is accumulated in the fermentation broth. Substantially no glycerol and/or substantially no ethanol is considered to be less than 5 g/L of glycerol or ethanol accumulated in the final fermentation broth. In an aspect less than 10, 7, 5, 4, 3, 2, 1, 0.5 g/L or less ethanol and/or glycerol is accumulated in the fermentation broth.

In an aspect, a cellulosic or lignocellulosic biomass/substrate can be pretreated with dilute sulfuric acid to hydrolyze most of the xylan and a small amount of glucan into xylose and glucose, respectively. The pretreated slurry can be treated by enzymatic hydrolysis (using e.g., cellobiase and cellulase) where most of the glucan is converted to glucose. The hydrolysate can then be concentrated to increase the sugar concentrations and to remove fermentation inhibitors including acetic acid, furfural, and hydroxymethyl furfural (HMF). Recovery of 2,3-BDO can be accomplished via found a hybrid extraction-distillation process or a conventional distillation process. Any suitable solvent (e.g., oleyl alcohol) can be used for recovering 2,3-BDO. The fermentation effluent can be first distilled to about 100, 200, 250, 300, 400, 500 g/L or more 2,3-BDO for a consistent recovery of 2,3-BDO across fermentation titers. The total mass flow rate of solvent sent to the multi-stage mixer-settlers can be about 1.0, 1.2, or 1.5 times the mass flow rate of water in the feed. The extract is distilled at a pressure of about 0.03, 0.04, 0.05, 0.06, 0.07, 0.08, or 0.09 atm to operate the reboiler at a temperature (e.g., about 400, 500, 524.77, 550, 600 K) at which heating agents are available and to lower the heating requirement. The water, 2,3-BDO, and acetoin are then distilled by sequential conventional distillation at about 0.1, 0.2, or 0.3 atm. The recovered acetoin can be sent back to fermentation to increase the overall conversion to 2,3-BDO.

In an aspect, methods described herein can produce 2,3-BDO at more than 0.1, 0.5, 1.0, 1.25, 1.5, 1.75 g/L/h. In an aspect, methods described herein can produce 2,3,-BDO at a yield of 50, 70, 80, 90, 100, 110, 120, 130, 140, 150 g/L or more.

Methods of Producing Methyl Ethyl Ketone (MEK)

In an aspect, methods of producing methyl ethyl ketone are provided. As discussed above, a substrate can be contacted a recombinant yeast culture as described herein under fermentation conditions. 2,3-BDO can be collected from the fermentation broth and purified from to form purified 2,3-BDO. The purified 2,3-BDO can be subjected to catalytic dehydration such that MEK is produced. A catalyst for the catalytic dehydration can be, for example, tricalcium phosphate or any other suitable catalyst. The purified 2,3-BDO can be greater than 70, 80, 90, 95, 97, 98, 99, 99.5 wt % pure or more.

In an aspect, concentrated hydrolysate can be used as a substrate for continuous fermentation to produce crude 2,3-BDO (the fermentation broth), following a series of solvent extraction and vacuum distillation unit operations which can be used to separate and purify 2,3-BDO to approximately 100 wt %. The purified 2,3-BDO can subsequently be converted to MEK (major) and isobutyraldehyde (IBA, minor) as products via catalytic dehydration (see, e.g., [6], [11], [40]). Finally, MEK can purified through vacuum distillation to >99.5 wt % and sold as the main product of the biorefinery, and IBA can be hydrogenated into isobutyl alcohol (IBO), which is purified to >99.5 wt % through distillation and sold as a co-product.

In some aspects MEK can be produced by pre-treating cellulosic or lignocellulosic biomass/substrate with dilute sulfuric acid to hydrolyze most of the xylan and a small amount of glucan into xylose and glucose, respectively. The pretreated slurry can be treated by enzymatic hydrolysis (using e.g., cellobiase and cellulase) where most of the glucan is converted to glucose. The hydrolysate can then be concentrated to increase the sugar concentrations and to remove fermentation inhibitors including acetic acid, furfural, and hydroxymethyl furfural (HMF). Hydrolysate concentration can be realized through a multi-effect evaporator (see FIG. 13; [6]), which can be included to reduce the maximum concentration of fermentation inhibitors (acetic acid, furfural, and hydroxymethyl furfural, all of which are volatile) to below 1 g/L [5]. The hydrolysate can be concentrated so that at the target titer, the steady state concentration of 2,3-BDO in the main fermenter equals the target titer. In the case that not enough inhibitors have been removed, the hydrolysate can be concentrated to a greater level than needed for the target titer (so that more inhibitors can be removed), and dilution water can be added in the fermenter to maintain the target titer. Further, a maximum sugar (glucose, xylose, mannose, arabinose, and galactose) concentration of can be about 200, 300, 400, 500, 600, 700, 800, or 900 g/L so that the viscosity of the concentrated hydrolysate will not exceed the capacity of the centrifuge pump [5].

For the fermentation units (a main fermenter and a seed train), the design algorithms as in Bhagwat et al. [5] can be used to size the reactors (based on the retention time calculated through target titer and productivity).

Recovery of 2,3-BDO can be accomplished via found a hybrid extraction-distillation process (Harvianto et al. [9]) or a conventional distillation process. Any suitable solvent (e.g., oleyl alcohol) can be used for recovering 2,3-BDO. The fermentation effluent can be first distilled to about 100, 200, 250, 300, 400, 500 g/L or more 2,3-BDO for a consistent recovery of 2,3-BDO across fermentation titers. The total mass flow rate of solvent sent to the multi-stage mixer-settlers can be about 1.0, 1.2, or 1.5 times the mass flow rate of water in the feed. The extract is distilled at a pressure of about 0.03, 0.04, 0.05, 0.06, 0.07, 0.08, or 0.09 atm to operate the reboiler at a temperature (e.g., about 400, 500, 524.77, 550, 600 K) at which heating agents are available and to lower the heating requirement. The water, 2,3-BDO, and acetoin are then distilled by sequential conventional distillation at about 0.1, 0.2, or 0.3 atm. The recovered acetoin can be sent back to fermentation to increase the overall conversion to 2,3-BDO.

The purified (around 99.7 wt %) 2,3-BDO stream can then sent to catalytic dehydration at about 200, 250, 300, 325, or 350° C. with a catalyst such as tricalcium phosphate. During the reaction, 2,3-BDO is converted to MEK and to isobutyraldehyde (IBA) [10]. After the reaction, the reactant stream is passed through a distillation column with IBA separated as the top product and MEK and 2,3-BDO in the bottom product. IBA can then be hydrogenated to isobutyl alcohol (IBO) using, e.g., a kieselguhr-supported carboxymethylcellulose-nickel catalyst or other suitable catalyst such that a >99.5 wt % pure IBO product can be obtained by removing the unreacted IBA using another distillation column, and the removed IBA can be recycled back to the hydrogenation reactor. Finally, the bottom product containing MEK and unreacted 2,3-BDO can be sent to another distillation column, where a MEK product of >99.9 wt % purity can be obtained through vacuum distillation, and the unreacted 2,3-BDO can be recycled back to the dehydration reactor.

Methods of Inducing Drought Tolerance and Improving Plant Health

In an aspect, drought tolerance can be induced in plants by contacting roots of the plants (e.g., monocotyledons or dicotyledons) with a spent fermentation broth. A fermentation broth can be produced by contacting any yeast culture described herein with a fermentation medium or substrate. The fermentation broth is the fluid remaining after a fermentation reaction.

In an aspect, plant health can be improved by contacting roots of the plants (e.g., monocotyledons or dicotyledons) with a spent fermentation broth. A spent fermentation broth can be the result of any medium that has been fermented by any yeast culture described herein. A fermentation broth can be used without any additional purification steps. In an aspect, a fermentation broth can be partially purified to remove yeast cells and fermentation debris. In an aspect, a fermentation broth can be partially purified to increase the purity of the 2,3-BDO. In an aspect, a fermentation broth or medium has substantially no glycerol and/or substantially no ethanol. Substantially no glycerol and/or substantially no ethanol is considered to be less than 5 g/L of glycerol or ethanol accumulated in the final fermentation broth or medium. In an aspect less than 10, 7, 5, 4, 3, 2, 1, 0.5 g/L or less ethanol and/or glycerol is present in the final fermentation broth or medium.

In an aspect, a fermentation broth comprises about 100, 200, 250, 300, 400, 500, 600, 700 or more μM or 2,3-BDO.

In an aspect, plants subjected to drought conditions and treated with a fermentation medium as described herein have a survival rate at least 1.1., 1.5, 1.75, 2.0, 2.5, 3.0, 4.0, 5.0-fold or more higher than plants not contacted with the fermentation medium.

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The following are provided for exemplification purposes only and are not intended to limit the scope of the embodiments described in broad terms above.

EXAMPLES

Example 1 Materials and Methods

Strains and Media

*E. coli* Top10 [F-mcrA Δ(mrr-hsdRMS-mcrBC) φ80lacZΔM15 ΔlacX74 recA1 araD139 Δ(ara-leu) 7697 galU galK rpsL (Str$^R$) endA1 nupG] was used for manipulation of plasmids. The *E. coli* strains were grown in Luria Bertani (LB) medium (1% tryptone, 0.5% yeast extract, 1% NaCl) at 37° C. with ampicillin (100 μg/mL) if necessary. A xylose-fermenting *S. cerevisiae* CT2 strain—a D452-2 derived strain with integration of two copies of expression cassettes containing XYL1, XYL2, and XYL3 in the background of PHO13 and ALD6 deletion [35]—was used as a host strain for introducing genetic modifications to produce 2,3-BDO. The CT2 strain, and its derived yeast strains were cultivated at 30° C. in YP medium (10 g/L yeast extract, 20 g/L peptone) with 20 g/L of glucose. For CRISPR-Cas9 based genome editing experiments, 120 μg/mL of nourseothricin, 300 μg/mL of geneticin, and 300 μg/mL of hygromycin B were added as necessary for selecting transformants.

Plasmid and Strain Construction

The strains used in this study are listed in Table 1. The plasmids, primers, guide RNA (gRNA) target sequences, and synthetic DNA sequences used in this study are listed in Table 2, 3, 4, and 5, respectively.

TABLE 1

Strains used or constructed in this study

| Strain | Description | Source |
|---|---|---|
| CT2 | D452-2 pho13Δ::XYL123 ald6Δ::XYL123 his3, trp1, leu2, and ura3 | Tsai et al. [35] |
| CTL | CT2 pdc1Δ::LDH from *Rhizopus oryzae* | This study |
| CTLA | CT2 pdc1Δ::LDH from *Rhizopus oryzae*, adh1Δ | This study |
| CTLAP | CTLA in which the endogenous promoter of PDC5 gene was substituted with TEX1 promoter | This study |
| CTLAB | CTLA in which the P$_{TDH3}$-alsS-T$_{CYC1}$ cassette has been integrated on chr XVI and the P$_{TDH3}$-alsD-T$_{CYC1}$ cassette has been integrated on chr VII | This study |
| CTLABM | CTLAB has a mutation on ldhA gene (117$^{th}$ amino acid was missed) | This study |
| CTLABG1 | CTLABM, gpd1Δ | This study |
| CTLABG2 | CTLABM, gpd2Δ | This study |
| CTLABG1G2 | CTLABM, gpd1Δgpd2Δ | This study |
| CBMM | CTLABG1G2 employing a Pyruvate-Malate cycle | This study |
| CBMMP1 | CBMM in which the endogenous promoter of PYC1 gene was substituted with the TEF1 promoter | This study |

TABLE 1-continued

| Strains used or constructed in this study | | |
| --- | --- | --- |
| Strain | Description | Source |
| CBMMP2 | CBMM in which the endogenous promoter of PYC2 gene was substituted with the PGK1 promoter | This study |
| CBMMP1P2 | CBMM in which the endogenous promoter of PYC1 gene was substituted with the TEF1 promoter and the endogenous promoter of PYC2 gene was substituted with the PGK1 promoter | This study |

TABLE 2

| Plasmids used in this study | | |
| --- | --- | --- |
| Name | Description of plasmids | Reference |
| pRS423GPD | HIS3, TDH3 promoter, CYC1 terminator, 2μ origin, and Amp$^R$ | Mumberg et al. [73] |
| pRS426GPD | URA3, TDH3 promoter, CYC1 terminator, 2μ origin, and Amp$^R$ | Mumberg et al. [73] |
| pRS426TEF | URA3, TEF1 promoter, CYC1 terminator, 2μ origin, and Amp$^R$ | This study |
| pRS423_alsS | pRS423GPD harboring alsS gene from *B. subtilis* | Kim et al. [74] |
| pRS426_alsD | pRS426GPD harboring alsD gene from *B. subtilis* | Kim et al. [74] |
| pRS405_LDH | pRS405PGK harboring ldhA gene from *R. oryzae* | Turner et al. [75] |
| pRS423_MDH3 | pRS423GPD harboring MDH3 gene from *S. cerevisiae* | This study |
| pCas9-NAT | Cas9 expression plasmid, NAT1 marker | Zhang et al. [57] |
| pRS42K | 2μ origin, KanMX | EUROSCARF |
| pRS42H | 2μ origin, hph | EUROSCARF |
| pRS42H-CS6 | pRS42H, gRNA cassette targeting the intergenic site on Chr VII | Kwak et al. [59] |
| pRS42K-CS8 | pRS42K, gRNA cassette targeting the intergenic site on Chr XVI | Kwak et al. [59] |
| pRS42K-CS9 | pRS42K, gRNA cassette targeting the intergenic site on Chr VIII | Lee et al. [58] |
| pRS42K-PDC1 | pRS42K, gRNA cassette targeting the PDC1 gene | This study |
| pRS42H-ADH1 | pRS42H, gRNA cassette targeting the ADH1 gene | This study |
| pRS42K-PDC5 | pRS42K, gRNA cassette targeting the promoter of the PDC5 gene | This study |
| pRS42K-GPD1 | pRS42K, gRNA cassette targeting the GPD1 gene | This study |
| pRS42H-GPD2 | pRS42H, gRNA cassette targeting the GPD2 gene | This study |
| pRS42H-LDH | pRS42H, gRNA cassette targeting the LDH gene in the PDC1 locus | This study |
| pRS42K-PYC1 | pRS42H, gRNA cassette targeting the promoter of the PYC1 gene | This study |
| pRS42H-PYC2 | pRS42H, gRNA cassette targeting the promoter of the PYC2 gene | This study |

TABLE 3

| Primers used in this study | | |
| --- | --- | --- |
| Name | Direction | Sequence |
| GPD-F | Sense | 5'-GCTGCAGGAATTCGATATCAAGCT-3' (SEQ ID NO: 1) |
| GPD-R | Antisense | 5'-CCGGGGGATCCACTAGTTCTAGAA-3' (SEQ ID NO: 2) |
| tMDH3-F | Sense | 5'-AAACACCAGAACTTAGTTTCGACGGATTCTAGAACTAGTG GATCCCCCGGATGGTCAAAGTCGCAATTCTTGGC-3'(SEQ ID NO: 3) |
| tMDH3-R | Antisense | 5'-ATGACTCGAGGTCGACGGTATCGATAAGCTTGATATCGAA TTCCTGCAGCTTAAGAGTCTAGGATGAAACTCTTGCC-3' (SEQ ID NO: 4) |
| gRNA-U | Sense | 5'-CCCGAGCTCTCTTTGAAAAGATAATGTATGATTATG-3' (SEQ ID NO: 5) |
| gRNA-D | Antisense | 5'-AACTGCAGGGATCCAGACATAAAAAACAAAAAAAGCAC-3' (SEQ ID NO: 6) |

TABLE 3-continued

Primers used in this study

| Name | Direction | Sequence |
|------|-----------|----------|
| dDNA-LDH-F | Sense | 5'tcataacctcacgcaaaataacacagtcaaatcaatcaaaATGGTATTA CACTCAAAGGT-3' (SEQ ID NO: 7) |
| dDNA-LDH-R | Antisense | 5'-tgcttataaaacttttaactaataattagagattaaatcgcTCCTCAAC AGCTACTTTTAG-3' (SEQ ID NO: 8) |
| dDNA-ADH1-F | Sense | 5'-CTGCACAATATTTCAAGCTATACCA-3' (SEQ ID NO: 9) |
| dDNA-ADH1-R | Antisense | 5'-CATAAGAAATTCGCTTATTTAGAAGTGT-3' (SEQ ID NO: 10) |
| dDNA-TEX1-F | Sense | 5'-gccaaggaaataaagcaaataacaataacaccattattttGCATAAC CTTGAAGGTTAAC-3' (SEQ ID NO: 11) |
| dDNA-TEX1-R | Antisense | 5'-tcaatctttcaaataaatatttacctaaggttatttcaGACATGCCGA ATAGTTCACTTG-3' (SEQ ID NO: 12) |
| dDNA-CS6-F | Sense | 5'-aacctcgaggagaagttttttttacccctctccacagatcCAGGAAACA GCTATGACCATG-3' (SEQ ID NO: 13) |
| dDNA-CS6-R | Antisense | 5'-taattaggtagaccgggtagattttttccgtaaccttggtgtcTGTAAA ACGACGGCCAGT-3' (SEQ ID NO: 14) |
| dDNA-CS8-F | Sense | 5'-caaaattacctacggtaattagtgaaaggccaaatctaatgttacaa taAATTAACCCTCACTAAAGGGA-3' (SEQ ID NO: 15) |
| dDNA-CS8-R | Antisense | 5'-gaccgttccttgtgttgtaccagtggtagggttcttctcggtagctt ctGTAATACGACTCACTATAGGGC-3' (SEQ ID NO: 16) |
| dDNA-GPD1-F | Sense | 5'-TTAATTTTCTTTTATCTTACTCTCC-3' (SEQ ID NO: 17) |
| dDNA-GPD1-R | Antisense | 5'-TAGTTATGAGAAATGACATAATGC-3' (SEQ ID NO: 18) |
| dDNA-GPD2-F | Sense | 5'-CGCTCCCCTTCCTTATCAATGC-3' (SEQ ID NO: 19) |
| dDNA-GPD2-R | Antisense | 5'-GGAGAGTGTCTATTCGTCATCG-3' (SEQ ID NO: 20) |
| dDNA-CS9-F | Sense | 5'-aggattcattagtggaaaagttcagtgacaaaatctagaaaataatat gaAATTAACCCTCACTAAAGGGA-3' (SEQ ID NO: 21) |
| dDNA-CS9-R | Antisense | 5'-gaatatagcgtatttttatttaatcacggtacaatggagatatttgca tgGTAATACGACTCACTATAGGGC-3' (SEQ ID NO: 22) |
| dDNA-ME-F | Sense | 5'-tctcaattattattttctactcataacctcacgcaaaataacacagtc aaatcaatcaaaATGCCAGCACATTTTGCCCC (SEQ ID NO: 23) |
| dDNA-ME-R | Antisense | 5'-tatttttcgttacataaaaatgcttataaaactttaactaataatta gagattaaatcgcCTACTGTGCCTGCTGTTCCG (SEQ ID NO: 24) |
| dDNA-PYC1-F | Sense | 5'-ccgtacttgcagcccgttgccaattgccgcctaatattgtCATAGCTT CAAAATGTTTCT (SEQ ID NO: 25) |
| dDNA-PYC1-R | Antisense | 5'-tgaagttatctctcaagccggcgaattttctttgcgacatCTTAGATT AGATTGCTATGC (SEQ ID NO: 26) |
| dDNA-PYC2-F | Sense | 5'-cctcaaacaagaattgtacgacattacgttcaagaaaattAAGAAATT ACCGTCGCTCGT (SEQ ID NO: 27) |
| dDNA-PYC2-R | Antisense | 5'-aattgtccctaagaccggccaatttcttgctactgctcatAGACATTG TTTTATATTTGT (SEQ ID NO: 28) |
| Conf-LDH-F | Sense | 5'-TTCATAATTGCATAATATTGTCCGC-3' (SEQ ID NO: 29) |
| Conf-LDH-R | Antisense | 5'-TTGCAATGTGTGTCAAGATATCG-3' (SEQ ID NO: 30) |
| Conf-ADH1-F | Sense | 5'-TTACACTGCCTCATTGATGGTGG-3' (SEQ ID NO: 31) |
| Conf-ADH1-R | Antisense | 5'-TACAATTGGGTGAAATGGGGAGCG-3' (SEQ ID NO: 32) |
| Conf-PDC5-F | Sense | 5'-GGTGAGAATCCTTCTGATGCATACT-3' (SEQ ID NO: 33) |
| Conf-PDC5-R | Antisense | 5'-GTGCTCTACTGGTGATTTTTCATCG-3' (SEQ ID NO: 34) |
| Conf-CS6-F | Sense | 5'-GTCTGCCGAAATTCTGTG-3' (SEQ ID NO: 35) |
| Conf-CS6-R | Antisense | 5'-CGGTCAGAAAGGGAAATG-3' (SEQ ID NO: 36) |

TABLE 3-continued

Primers used in this study

| Name | Direction | Sequence |
| --- | --- | --- |
| Conf-CS8-F | Sense | 5'-AGTGGAACATAGAAGGGG-3' (SEQ ID NO: 37) |
| Conf-CS8-R | Antisense | 5'-TAAGCAGCCCAGTGAAC-3' (SEQ ID NO: 38) |
| Conf-GPD1-F | Sense | 5'-CCTACTGTCCCTATGTCTCTGG-3' (SEQ ID NO: 39) |
| Conf-GPD1-R | Antisense | 5'-CCAAAGTACATCCTTGTCGAGC-3' (SEQ ID NO: 40) |
| Conf-GPD2-F | Sense | 5'-AAGAGTGTTTAGCTTACGGACCTATTGCCA-3' (SEQ ID NO: 41) |
| Conf-GPD2-R | Antisense | 5'-CAGTAGTGACTAACATAGCGCTCTTATCTC-3' (SEQ ID NO: 42) |
| Conf-CS9-F | Sense | 5'-TGGTAATGAGGAATGCGT-3' (SEQ ID NO: 43) |
| Conf-CS9-R | Antisense | 5'-CGGGCATTATGCGTAGAT-3' (SEQ ID NO: 44) |
| Conf-ME-F | Sense | 5'-TTCATAATTGCATAATATTGTCCGC-3' (SEQ ID NO: 45) |
| Conf-ME-R | Antisense | 5'-GACAGTGCAGTAATAATATGAACC-3' (SEQ ID NO: 46) |
| Conf-PYC1-F | Sense | 5'-TCGACGAATGGTAGCGCTTG-3' (SEQ ID NO: 47) |
| Conf-PYC1-R | Antisense | 5'-CTTAGATTAGATTGCTATGC-3' (SEQ ID NO: 48) |
| Conf-PYC2-F | Sense | 5'-CCTCAAACAAGAATTGTACG-3' (SEQ ID NO: 49) |
| Conf-PYC2-R | Antisense | 5'-AATTGTCCCTAAGACCGGCC-3' (SEQ ID NO: 50) |

Restriction sites are underlined, and homologous regions for Donor DNA integration are lowercased.

TABLE 4

Target sequences of gRNA used for CRISPR-Cas9 based genome editing in this study

| Name | Sequence |
| --- | --- |
| CS6 | 5'-GATACTTATCATTAAGAAAA-3' (SEQ ID NO: 51) |
| CS8 | 5'-TGATTCAATCATTCTTATTG-3' (SEQ ID NO: 52) |
| CS9 | 5'-TAACTATTACTTGTTTCTAT-3' (SEQ ID NO: 53) |
| PDC1 | 5'-TCTGTCAATTTCAGCTGGGG-3' (SEQ ID NO: 54) |
| ADH1 | 5'-CCATCTTGTGTGCTGGTATC-3' (SEQ ID NO: 55) |
| PDC5 | 5'-GGAAAAGCCTCCATATCCAA-3' (SEQ ID NO: 56) |
| GPD1 | 5'-GGCTGCCGAAAAGCCTTTCA-3' (SEQ ID NO: 57) |
| GPD2 | 5'-TGCAAACTTGGCACCGGAAG-3' (SEQ ID NO: 58) |
| LDH | 5'-AGTCACACGCCCATCCGAGC-3' (SEQ ID NO: 59) |
| PYC1 | 5'-TAGAGGGACCTGTGTTTGAC-3' (SEQ ID NO: 60) |
| PYC2 | 5'-ATTACTATATTGCAAAATAA-3' (SEQ ID NO: 61) |

TABLE 5

Synthetic DNA sequence used in this study

| Name | Sequence (5'→3') | Source |
| --- | --- | --- |
| tMDH3 | ATGGTCAAAGTCGCAATTCTTGGCGCTTCTGGTGGCGTGGG ACAACCGCTATCATTACTGCTAAAATTAAGCCCTTACGTTTCC GAGCTGGCGTTGTACGATATCCGAGCTGCGGAAGGCATTGG TAAGGATTTATCTCACATCAACACCAACTCAAGTTGTGTCGG TTATGATAAGGATAGTATTGAGAACACCTTGTCAAATGCTCA GGTGGTGCTAATACCGGCTGGTGTTCCCAGAAAGCCCGGTT TAACTAGAGATGATTTGTTCAAGATGAACGCCGGTATTGTCA AAAGCCTGGTAACCGCTGTTGGAAAGTTCGCACCAAATGCG AGGATTTTAGTCATTTCAAACCCTGTAAACAGTTTGGTCCCTA TTGCTGTGGAAACTTTGAAGAAAATGGGTAAGTTCAAACCTG GAAACGTTATGGGTGTGACGAACCTTGACCTGGTACGTGCA | MDH3 gene from *S. cerevisiae* (SEQ ID NO: 62) |

TABLE 5-continued

Synthetic DNA sequence used in this study

| Name | Sequence (5'→3') | Source |
|---|---|---|
| | GAAACCTTTTTGGTAGATTATTTGATGCTAAAAAACCCCAAAA TTGGACAAGAACAAGACAAAACTACAATGCACAGAAAGGTCA CTGTTATTGGGGGTCATTCAGGGGAAACCATTATCCCAATAA TCACCGACAAATCGCTGGTATTTCAACTTGATAAGCAGTACG AGCACTTCATTCATAGGGTCCAGTTCGGAGGTGATGAAATTG TCAAAGCTAAACAGGGCGCCGGTTCCGCCACGTTGTCCATG GCGTTCGCGGGGGCCAAGTTTGCTGAAGAAGTTTTGAGGAG CTTCCATAATGAGAAACCAGAAACGGAGTCACTTTCCGCATT CGTTTATTTACCAGGCTTAAAAAACGGTAAGAAAGCGCAGCA ATTAGTTGGCGACAACTCTATTGAGTATTTTTCCTTGCCAATT GTTTTGAGAAATGGTAGCGTAGTATCCATCGATACCAGTGTT CTGGAAAAACTGTCTCCGAGAGAGGAACAACTCGTTAATACT GCGGTCAAAGAGCTACGCAAGAATATTGAAAAAGGCAAGAG TTTCATCCTAGACTCTTCCAAGCTATGA | |
| Donor ADH1 (SEQ ID NO: 63) | CTGCACAATATTTCAAGCTATACCAAGCATACAATCAACTATC TCATATACAATGTCTATCCCAGAAACTCAAAAAGGTGTTATCT TCTACGAATCCCACGTCGGCTTGTCTACCTTGCCAGAAATT TACGAAAAGATGGAAAAGGGTCAAATCGTTGGTAGATACGTT GTTGACACTTCTAAATAAGCGAATTTCTTATG | |
| Donor GPD1 (SEQ ID NO: 64) | TTAATTTTCTTTTATCTTACTCTCCTACATAAGACATCAAGAAA CAATTGTATATTGTACACCCCCCCCCTCCACAAACACAAATA TTGATAATATAAAGATTTATTGGAGAAAGATAACATATCATAC TTTCCCCCACTTTTTTCGAGGCTCTTCTATATCATATTCATAA ATTAGCATTATGTCATTTCTCATAACTA | |
| Donor GPD2 (SEQ ID NO: 65) | CGCTCCCCTTCCTTATCAATGCTTGCTGTCAGAAGATTAACA AGATACACATTCCTTAAGCGAACGCATCCGGTGTTATATACT CGTCGTGCATATAAAAATTCGAGGCAGTCTACCAGATAGTCT ACAACAACGTCCGCATGGAAGACCTACCGGAGATGATTGAA GAGCTAGACATCGATGACGAATAGACACTCTCC | |
| ME1 (SEQ ID NO: 66) | ATGCCAGCACATTTTGCCCCATCCCAACCATTACAAGGTGG GCCAAGCCCCAGCCAACTGGGACCAAAAGAACTGCTGATTG AGAGGGCTCTTACCAGACTACGTTCCATCCCCAACGACTTA GAAAAATACACATTTTTAGCGGGGCTAAGAGGAAGAAATCCA GACGTTTTTTATGGATTAGTCGGGGGAAATATGAAAGAGTGT TGCCCGATTATATATACCCCAGTGATAGGGCTTGCCTGTCAA AATTGGTCCTTAATCCATCCGCCTCCCCCTGAATCCGACCCA ACGATTGACGCTCTTTACTTGAGTTATAGCGATCTTCCAAAC CTACCCCAGCTTATCGGTGGGTTAAAGACAAGGTTACCTCAT GATCAGATGCAGATCAGCGTTGTCACTGACGGTAGCCGTGT CCTTGGCTTAGGTGATCTGGGGGGTTGGCGGAATGGGGATAT CCCAAGGAAAGCTATCACTGTATGTCGCCGCAGGGGGTGTG AATCCTAAAGCCACTTTGCCTATAGCAATTGATTTCGGCACA GATAATGAGACTCTGCTAGCCGATCCGTTGTACGTAGGTCAA AGGATTCGTAGATTGAGCCAGGAGAAGTGCTTAGAGTTCAT GGAGGTCTTTATGCGTTGCATGCATGAGACTTTTCCCAATAT GGTAATCCAACACGAAGATTGGCAAACTCCGCTGGCCTTCC CTCTATTACACAAAAACCGTGATCTATACCCATGCTTCAACG ATGATATCCAAGGAACCGGCGCTGTAGTACTGGCCGGCGCC ATAAGAGCATTCCATCTGAACGGCGTCGCACTGAAAGACCA GAAAATTTTGTTCTTTGGCGCGGGGTCAAGTGGCGTGGGTG TCGCGGAGACGATC | |
| ME1 (SEQ ID NO: 67) | GGCGCGGGGTCAAGTGGCGTGGGTGTCGCGGAGACGATC TGCAAATACTTTGAGCTACAGGGGATGAGTGAAGATGAAGC TAAAAGCAAATTCTGGTTGGTTGATAGTAAGGGGCTAGTTGC TCACAATCGTGGCGATACTTTACCTAGCCACAAAAAGTACCT TGCCAAGAAGTGAGCCTGATGCGCCTAAATTGAGGACGCTAA AGGAAGTCGTAGAACATGTACAACCCACGGCCTTGTTAGGG CTTAGCACAGTTGGGGGTACATTCACAAAGGAAATTCTTGAA GCAATGGCCACTTATAACAAACGTCCTATTGTCTTTGCACTT AGCAATCCAGTAGCGCAAGCTGAATGCACGTTCGAGGAAGC TGTGGAGGGAACCGACGGAAGGGTCTTTATATGCCAGTGGAA GTCCCTTTGACCCCGTGGAGTACAAAGGCAAAAGGTATGAA CCAGGACAGGGCAACAATATGTACATCTTCCCCGGCCTGGG TATAGGTGCCATTTTGGCGAGGGTGAGTAAAATCCCGGAAG AGCTGGTTCATGCATCAGCACAAGGGCTTGCGGACTCATTA ACGCCGGAGGAAACGGCGCGTCATTTGCTGTATCCAGATAT AGAACGTATAAGGGAAGTTAGTATTAAGATAGCAGTTACCGT | ME1 from *R. toruloides* was codon optimized for *S. cerevisiae* |

TABLE 5-continued

Synthetic DNA sequence used in this study

| Name | Sequence (5'→3') | Source |
|---|---|---|
| | AATCCAAGCGGCACAGAAGCTTGGTGTTGATAGAAACGAGG AGCTTAGAGGGAAAAGCAGTGCTGAAATTGAAGCCTATGTA CGTAAAGGGATGTACCATCCATTACTTGAGGCGGAACAGCA GGCACAGTAG | | tMDH3 gene from *S. cerevisiae* was synthesized except for the last 9 base pairs that encode the peroxisomal targeting sequence (tripeptide SKL)

Recombinant DNA techniques were performed according to standard procedures. A lithium acetate transformation method with single strand carrier DNA and polyethylene glycerol [36] was used to introduce Cas9-NAT, gRNA expression vectors, and donor DNA fragment into yeast strains. Putative transformants on selection plates were confirmed by colony PCR.

Plasmid Construction

Construction of pRS423_MDH3: To express malate dehydrogenase (MDH) in the cytosol of *S. cerevisiae*, a truncated MDH3 (tMDH3) gene from *S. cerevisiae* was synthesized except for the last 9 base pairs (tripeptide SKL) encoding for peroxisomal targeting sequence using the gBlocks service from Integrated DNA Technologies (IDT, IA, USA). To construct a truncated MDH expression plasmid (pRS423_tMDH3), a DNA fragment (vector fraction) was amplified from pRS423GPD plasmid using GPD-F and GPD-R primers and another DNA fragment (insert fraction) was amplified from the synthetic oligomer using tMDH3-F and tMDH3-R primers. The two PCR products were *Arabidopsis* plants and be used as a biostimulant for plant health in the agriculture industry.

Example 6 Conclusion

This study combined experimental yeast 2,3-BDO production from lignocellulosic biomass with two potential downstream uses: (i) as a feedstock for MEK production via catalytic dehydration of 2,3-BDO and (ii) as a biostimulant to induce drought tolerance in plants. Our engineered yeast strain produced 109.9 g/L of 2,3-BDO with a productivity of 1.0 g/L/h without ethanol and glycerol in fed-batch fermentation through metabolic reprogramming. When a TEA was conducted based on the experimental results, the MPSP ($1.90/kg [$1.66-2.27/kg]) of produced MEK was within the market price range ($1.40-1.98/kg) of petroleum-based MEK. Regarding cradle-to-grave LCA, both $GWP_{100}$ (0.37 kg $CO_2$ eq/kg [−0.46-1.53 kg $CO_2$ eq/kg]) and FEC (3.1 MJ/kg [−6.9-19.8 MJ/kg]) impacts of the produced MEK were significantly lower than the previously reported values (3.48-4.36 kg $CO_2$ eq/kg and 43.0-58.7 MJ/kg, respectively) for petroleum-based MEK. This study demonstrated the potential for economical and sustainable bio-based MEK production from lignocellulosic biomass. In addition, as another potential application of 2,3-BDO, we demonstrated that yeast 2,3-BDO fermentation broth could be used as a biostimulant for inducing drought tolerance in *Arabidopsis* plants without a complicated purification process.

REFERENCES

[1] A.-P. Zeng, W. Sabra, Microbial production of diols as platform chemicals: Recent progresses, Curr. Opin. Biotechnol. 22(6) (2011) 749-757. doi.org/10.1016/j.copbio.2011.05.005.

[2] Y. Zhang, D. Liu, Z. Chen, Production of C2-C4 diols from renewable bioresources: new metabolic pathways and metabolic engineering strategies, Biotechnol. Biofuels 10(1) (2017) 299. doi.org/10.1186/s13068-017-0992-9.

[3] X.-J. Ji, H. Huang, P.-K. Ouyang, Microbial 2,3-butanediol production: A state-of-the-art review, Biotechnol. Adv. 29(3) (2011) 351-364. doi.org/10.1016/j.biotechadv.2011.01.007.

[4] E. Celihska, W. Grajek, Biotechnological production of 2,3-butanediol—Current state and prospects, Biotechnol. Adv. 27(6) (2009) 715-725. doi.org/10.1016/j.biotechadv.2009.05.002.

[5] N. S. Kruyer, M. J. Realff, W. Sun, C. L. Genzale, P. Peralta-Yahya, Designing the bioproduction of Martian rocket propellant via a biotechnology-enabled in situ resource utilization strategy, Nat. Commun. 12(1) (2021) 6166. doi.org/10.1038/s41467-021-26393-7.

[6] D. Penner, C. Redepenning, A. Mitsos, J. Viell, Conceptual Design of Methyl Ethyl Ketone Production via 2,3-Butanediol for Fuels and Chemicals, Ind. Eng. Chem. Res. 56(14) (2017) 3947-3957. doi.org/10.1021/acs.iecr.6b03678.

[7] F. Hoppe, B. Heuser, M. Thewes, F. Kremer, S. Pischinger, M. Dahmen, M. Hechinger, W. Marquardt, Tailor-made fuels for future engine concepts, Int. J. Engine Res. 17(1) (2016) 16-27. doi.org/10.1177/1468087415603005.

[8] Grand View Research, Methyl Ethyl Ketone Market Size, Share & Trends Analysis Report By Application (Paints & Coatings, Printing Inks, Adhesive), By Region (North America, Europe, APAC, MEA, CSA), and Segment Forecasts, 2016-2024, grandviewresearch.com/industry-analysis/methyl-ethyl-ketone-mek-market, 2016 (accessed 7 Dec. 2021).

[9] L. Torres-Vinces, G. Contreras-Zarazua, B. Huerta-Rosas, E. Sánchez-Ramirez, J. G. Segovia-Hernández, Methyl Ethyl Ketone Production through an Intensified Process, Chem. Eng. Technol. 43(7) (2020) 1433-1441. doi.org/10.1002/ceat.201900664.

[10] Z. Liu, W. Huo, H. Ma, K. Qiao, Development and Commercial Application of Methyl-ethyl-ketone Production Technology, Chin. J. Chem. Eng. 14(5) (2006) 676-684. doi.org/10.1016/S1004-9541(06)60134-1.

[11] R. R. Emerson, M. C. Flickinger, G. T. Tsao, Kinetics of dehydration of aqueous 2,3-butanediol to methyl ethyl ketone, Ind. Eng. Chem. 21(3) (1982) 473-477. doi.org/10.1021/i300007a025.

[12] J. Ishii, K. Morita, K. Ida, H. Kato, S. Kinoshita, S. Hataya, H. Shimizu, A. Kondo, F. Matsuda, A pyruvate carbon flux tugging strategy for increasing 2,3-butanediol production and reducing ethanol subgeneration in the yeast *Saccharomyces cerevisiae*, Biotechnol. Biofuels 11(1) (2018) 180. doi.org/10.1186/s13068-018-1176-y.

[13] J.-W. Kim, S.-O. Seo, G.-C. Zhang, Y.-S. Jin, J.-H. Seo, Expression of *Lactococcus lactis* NADH oxidase increases 2,3-butanediol production in Pdc-deficient *Saccharomyces cerevisiae*, Bioresour. Technol. 191 (2015) 512-519. doi.org/10.1016/j.biortech.2015.02.077.

[14] O. de Smidt, J. C. du Preez, J. Albertyn, Molecular and physiological aspects of alcohol dehydrogenases in the ethanol metabolism of *Saccharomyces cerevisiae*, FEMS Yeast Res. 12(1) (2012) 33-47. doi.org/10.1111/j.1567-1364.2011.00760.x.

[15] S. Kim, J.-S. Hahn, Efficient production of 2,3-butanediol in *Saccharomyces cerevisiae* by eliminating ethanol and glycerol production and redox rebalancing, Metab. Eng. 31 (2015) 94-101. doi.org/10.1016/j.ymben.2015.07.006.

[16] S.-J. Kim, S.-O. Seo, Y.-S. Jin, J.-H. Seo, Production of 2,3-butanediol by engineered *Saccharomyces cerevisiae*, Bioresour. Technol. 146 (2013) 274-281. doi.org/10.1016/j.biortech.2013.07.081.

[17] J.-W. Kim, J. Kim, S.-O. Seo, K. H. Kim, Y.-S. Jin, J.-H. Seo, Enhanced production of 2,3-butanediol by engineered *Saccharomyces cerevisiae* through fine-tuning of pyruvate decarboxylase and NADH oxidase activities, Biotechnol. Biofuels 9(1) (2016) 265. doi.org/10.1186/s13068-016-0677-9.

[18] Y.-G. Lee, J.-H. Seo, Production of 2,3-butanediol from glucose and cassava hydrolysates by metabolically engineered industrial polyploid *Saccharomyces cerevisiae*, Biotechnol. Biofuels 12(1) (2019) 204. doi.org/10.1186/s13068-019-1545-1.

[19] J.-W. Kim, Y.-G. Lee, S.-J. Kim, Y.-S. Jin, J.-H. Seo, Deletion of glycerol-3-phosphate dehydrogenase genes improved 2,3-butanediol production by reducing glycerol production in pyruvate decarboxylase-deficient *Saccharomyces cerevisiae*, J. Biotechnol. 304 (2019) 31-37. doi.org/10.1016/j.jbiotec.2019.08.009.

[20] J. W. Lee, Y. G. Lee, Y. S. Jin, C. V. Rao, Metabolic engineering of non-pathogenic microorganisms for 2,3-butanediol production, Appl. Microbiol. Biotechnol. 105 (2021) 5751-5767. doi.org/10.1007/s00253-021-11436-2.

[21] T. Yu, Y. J. Zhou, M. Huang, Q. Liu, R. Pereira, F. David, J. Nielsen, Reprogramming Yeast Metabolism from Alcoholic Fermentation to Lipogenesis, Cell 174(6) (2018) 1549-1558.e14. doi.org/10.1016/j.cell.2018.07.013.

[22] S. Maina, E. Dheskali, H. Papapostolou, A. M. d. Castro, D. M. Guimaraes Freire, G. J. E. Nychas, S. Papanikolaou, I. K. Kookos, A. Koutinas, Bioprocess Development for 2,3-Butanediol Production from Crude Glycerol and Conceptual Process Design for Aqueous Conversion into Methyl Ethyl Ketone, ACS Sustain. Chem. Eng. 9(26) (2021) 8692-8705. doi.org/10.1021/acssuschemeng.1c00253.

[23] Y. Cortes-Pena, D. Kumar, V. Singh, J. S. Guest, BioSTEAM: A Fast and Flexible Platform for the Design, Simulation, and Techno-Economic Analysis of Biorefineries under Uncertainty, ACS Sustain. Chem. Eng. 8(8) (2020) 3302-3310. doi.org/10.1021/acssuschemeng.9b07040.

[24] BioSTEAM Development Group, BioSTEAM: The Biorefinery Simulation and Techno-Economic Analysis Modules. github.com/BioSTEAMDevelopmentGroup/biosteam. (accessed 17 Apr. 2020).

[25] S. H. Han, S. J. Lee, J. H. Moon, K. H. Park, K. Y. Yang, B. H. Cho, K. Y. Kim, Y. W. Kim, M. C. Lee, A. J. Anderson, Y. C. Kim, GacS-dependent production of 2R, 3R-butanediol by *Pseudomonas chlororaphis O6* is a major determinant for eliciting systemic resistance against *Erwinia carotovora* but not against *Pseudomonas*

*syringae* pv. *tabaci* in tobacco, Mol Plant Microbe Interact 19(8) (2006) 924-930. doi.org/10.1094/mpmi-19-0924.

[26] M.-S. Hahm, M. Sumayo, Y.-J. Hwang, S.-A. Jeon, S.-J. Park, J. Y. Lee, J.-H. Ahn, B.-S. Kim, C.-M. Ryu, S.-Y. Ghim, Biological control and plant growth promoting capacity of rhizobacteria on pepper under greenhouse and field conditions, J. Microbiol. 50(3) (2012) 380-385. doi.org/10.1007/si2275-012-1477-y.

[27] H. G. Kong, T. S. Shin, T. H. Kim, C. M. Ryu, Stereoisomers of the Bacterial Volatile Compound 2,3-Butanediol Differently Elicit Systemic Defense Responses of Pepper against Multiple Viruses in the Field, Front. Plant Sci. 9 (2018) 90. doi.org/10.3389/fpls.2018.00090.

[28] Y. Shi, J. Zhang, H. Li, M. Li, B. Huang, Butanediol-enhanced heat tolerance in *Agrostis stolonifera* in association with alteration in stress-related gene expression and metabolic profiles, Environ. Exp. Bot. 153 (2018) 209-217. doi.org/10.1016/j. envexpbot.2018.06.002.

[29] Y. Shi, K. Niu, B. Huang, W. Liu, H. Ma, Transcriptional Responses of Creeping Bentgrass to 2,3-Butanediol, a Bacterial Volatile Compound (BVC) Analogue, Molecules 22(8) (2017). doi.org/10.3390/molecules22081318.

[30] J. L. Araus, G. A. Slafer, C. Royo, M. D. Serret, Breeding for Yield Potential and Stress Adaptation in Cereals, CRC Crit Rev Plant Sci. 27(6) (2008) 377-412. doi.org/10.1080/07352680802467736.

[31] M. Farooq, M. Hussain, A. Wahid, K. H. M. Siddique, Drought Stress in Plants: An Overview, in: R. Aroca (Ed.), Plant Responses to Drought Stress: From Morphological to Molecular Features, Springer Berlin Heidelberg, Berlin, Heidelberg, 2012, pp. 1-33. doi.org/10.1007/978-3-642-32653-0_1.

[32] L. Comas, S. Becker, V. M. Cruz, P. F. Byrne, D. A. Dierig, Root traits contributing to plant productivity under drought, Front. Plant Sci. 4(442) (2013). doi.org/10.3389/fpls.2013.00442.

[33] S. M. Cho, B. R. Kang, S. H. Han, A. J. Anderson, J.-Y. Park, Y.-H. Lee, B. H. Cho, K.-Y. Yang, C.-M. Ryu, Y. C. Kim, 2R,3R-Butanediol, a Bacterial Volatile Produced by *Pseudomonas chlororaphis O6*, Is Involved in Induction of Systemic Tolerance to Drought in *Arabidopsis thaliana*, Mol. Plant Microbe Interact. 21(8) (2008) 1067-1075. doi.org/10.1094/mpmi-21-8-1067.

[34] L. Wu, X. Li, L. Ma, R. Borriss, Z. Wu, X. Gao, Acetoin and 2,3-butanediol from *Bacillus amyloliquefaciens* induce stomatal closure in *Arabidopsis thaliana* and *Nicotiana benthamiana*, J. Exp. Bot. 69(22) (2018) 5625-5635. doi.org/10.1093/jxb/ery326.

[35] C.-S. Tsai, I. I. Kong, A. Lesmana, G. Million, G.-C. Zhang, S. R. Kim, Y.-S. Jin, Rapid and marker-free refactoring of xylose-fermenting yeast strains with Cas9/CRISPR, Biotechnol. Bioeng. 112(11) (2015) 2406-2411. doi.org/10.1002/bit.25632.

[36] R. D. Gietz, R. H. Schiestl, High-efficiency yeast transformation using the LiAc/SS carrier DNA/PEG method, Nat. Protoc. 2(1) (2007) 31-34. doi.org/10.1038/nprot.2007.13.

[37] A. Multer, N. McGraw, K. Hohn, P. Vadlani, Production of Methyl Ethyl Ketone from Biomass Using a Hybrid Biochemical/Catalytic Approach, Ind. Eng. Chem. Res. 52(1) (2013) 56-60. doi.org/10.1021/ie3007598.

[38] S.-J. Kim, S.-O. Seo, Y.-C. Park, Y.-S. Jin, J.-H. Seo, Production of 2,3-butanediol from xylose by engineered

*Saccharomyces cerevisiae*, J. Biotechnol. 192 (2014) 376-382. doi.org/10.1016/j.jbiotec.2013.12.017.

[39] J. Lian, R. Chao, H. Zhao, Metabolic engineering of a *Saccharomyces cerevisiae* strain capable of simultaneously utilizing glucose and galactose to produce enantiopure (2R,3R)-butanediol, Metab. Eng. 23 (2014) 92-99. doi.org/10.1016/j.ymben.2014.02.003.

[40] J. Zhao, D. Yu, W. Zhang, Y. Hu, T. Jiang, J. Fu, H. Huang, Catalytic dehydration of 2,3-butanediol over P/HZSM-5: effect of catalyst, reaction temperature and reactant configuration on rearrangement products, RSC Adv. 6(21) (2016) 16988-16995. doi.org/10.1039/C5RA23251A.

[41] BioSTEAM Development Group, Bioindustrial-Park: BioSTEAM's Premier Repository for Biorefinery Models and Results. github.com/BioSTEAMDevelopmentGroup/Bioindustrial-Park. (accessed 17 Apr. 2020).

[42] S. S. Bhagwat, Y. Li, Y. R. Cortes-Pena, E. C. Brace, T. A. Martin, H. Zhao, J. S. Guest, Sustainable Production of Acrylic Acid via 3-Hydroxypropionic Acid from Lignocellulosic Biomass, ACS Sustain. Chem. Eng. 9(49) (2021) 16659-16669. doi.org/10.1021/acssuschemeng.1c05441.

[43] T. Murashige, F. Skoog, A Revised Medium for Rapid Growth and Bio Assays with Tobacco Tissue Cultures, Physiol. Plant. 15(3) (1962) 473-497. doi.org/10.1111/j.1399-3054.1962.tb08052.x.

[44] N. Ishida, S. Saitoh, T. Onishi, K. Tokuhiro, E. Nagamori, K. Kitamoto, H. Takahashi, The Effect of Pyruvate Decarboxylase Gene Knockout in *Saccharomyces cerevisiae* on L-Lactic Acid Production, Biosci. Biotechnol. Biochem. 70(5) (2006) 1148-1153. doi.org/10.1271/bbb.70.1148.

[45] R. M. Zelle, E. de Hulster, W. A. van Winden, P. de Waard, C. Dijkema, A. A. Winkler, J.-M. A. Geertman, J. P. van Dijken, J. T. Pronk, A. J. A. van Maris, Malic Acid Production by *Saccharomyces cerevisiae*: Engineering of Pyruvate Carboxylation, Oxaloacetate Reduction, and Malate Export, Appl. Environ. Microbiol. 74(9) (2008) 2766. doi.org/10.1128/AEM.02591-07.

[46] M. T. Flikweert, L. van der Zanden, W. M. T. M. Janssen, H. Yde Steensma, J. P. van Dijken, J. T. Pronk, Pyruvate decarboxylase: An indispensable enzyme for growth of *Saccharomyces cerevisiae* on glucose, Yeast 12(3) (1996) 247-257. doi.org/10.1002/(SICI)1097-0061(19960315)12:3%3C247::AID-YEA911%3E3.0. CO;2-1

[47] J. T. Pronk, H. Y. Steensma, J. P. V. Dijken, Pyruvate Metabolism in *Saccharomyces cerevisiae*, Yeast 12(16) (1996) 1607-1633. doi.org/10.1002/(sici)1097-0061(199612)12:16<1607::aid-yea70>3.0.co;2-4

[48] C. D. Skory, Isolation and Expression of Lactate Dehydrogenase Genes from *Rhizopus oryzae*, Appl. Environ. Microbiol. 66(6) (2000) 2343-2348. doi.org/10.1128/aem.66.6.2343-2348.

[49] M. J. Syu, Biological production of 2,3-butanediol, Appl. Microbiol. Biotechnol. 55(1) (2001) 10-18. doi.org/10.1007/s002530000486.

[50] R. Ansell, K. Granath, S. Hohmann, J. M. Thevelein, L. Adler, The two isoenzymes for yeast NAD+-dependent glycerol 3-phosphate dehydrogenase encoded by GPD1 and GPD2 have distinct roles in osmoadaptation and redox regulation, EMBO J. 16(9) (1997) 2179-2187. doi.org/10.1093/emboj/16.9.2179.

[51] R. H. De Deken, The Crabtree effect: a regulatory system in yeast, J. Gen. Microbiol. 44(2) (1966) 149-156. doi.org/10.1099/00221287-44-2-149.

[52] J. Menendez, C. Gancedo, Regulatory regions in the promoters of the *Saccharomyces cerevisiae* PYC1 and PYC2 genes encoding isoenzymes of pyruvate carboxylase, FEMS Microbiol. Lett. 164(2) (1998) 345-352. doi.org/10.1111/j.1574-6968.1998.tb13108.x.

[53] B. Peng, T. C. Williams, M. Henry, L. K. Nielsen, C. E. Vickers, Controlling heterologous gene expression in yeast cell factories on different carbon substrates and across the diauxic shift: a comparison of yeast promoter activities, Microb. Cell Fact. 14 (2015) 91. doi.org/10.1186/s12934-015-0278-5.

[54] B. H. Silva Dias, S.-H. Jung, J. V. d. Castro Oliveira, C.-M. Ryu, C4 Bacterial Volatiles Improve Plant Health, Pathogens 10(6) (2021) 682. doi.org/10.3390/pathogens10060682

[55] Argonne National Laboratory, GREET 2020 Model, 2020.

[56] G. Wernet, C. Bauer, B. Steubing, J. Reinhard, E. Moreno-Ruiz, B. Weidema, The ecoinvent database version 3 (part 1): overview and methodology, Int. J. Life Cycle Assess. 21(9) (2016) 1218-1230. doi.org/10.1007/s11367-016-1087-8.

[57] G.-C. Zhang, I. I. Kong, H. Kim, J.-J. Liu, J. H. D. Cate, Y.-S. Jin, Construction of a quadruple auxotrophic mutant of an industrial polyploid *Saccharomyces cerevisiae* strain by using RNA-guided Cas9 nuclease, Appl. Environ. Microbiol. 80(24) (2014) 7694-7701. doi.org/10.1128/AEM.02310-14.

[58] J. W. Lee, S. Kwak, J. J. Liu, S. Yu, E. J. Yun, D. H. Kim, C. Liu, K. H. Kim, Y. S. Jin, Enhanced 2'-Fucosyllactose production by engineered *Saccharomyces cerevisiae* using xylose as a co-substrate, Metab. Eng. 62 (2020) 322-329. doi.org/10.1016/j.ymben.2020.10.003.

[59] S. Kwak, S. R. Kim, H. Xu, G. C. Zhang, S. Lane, H. Kim, Y. S. Jin, Enhanced isoprenoid production from xylose by engineered *Saccharomyces cerevisiae*, Biotechnol. Bioeng. 114(11) (2017) 2581-2591. doi.org/10.1002/bit.26369.

[60] C. D. Skory, Isolation and expression of lactate dehydrogenase genes from *Rhizopus oryzae*, Appl. Environ. Microbiol. 66(6) (2000) 2343-8. doi.org/10.1128/aem.66.6.2343-2348.2000.

[61] S. S. Bhagwat, Y. Li, Y. R. Cortes-Pena, E. C. Brace, T. A. Martin, H. Zhao, J. S. Guest, Sustainable Production of Acrylic Acid via 3-Hydroxypropionic Acid from Lignocellulosic Biomass, ACS Sustain. Chem. Eng. (2021). doi.org/10.1021/acssuschemeng.1c05441.

[62] BioSTEAM Development Group, Bioindustrial-Park: BioSTEAM's Premier Repository for Biorefinery Models and Results. github.com/BioSTEAMDevelopmentGroup/Bioindustrial-Park. (accessed 17 Apr. 2020).

[63] R. Davis, N. Grundl, L. Tao, M. J. Biddy, E. C. Tan, G. T. Beckham, D. Humbird, D. N. Thompson, M. S. Roni, Process Design and Economics for the Conversion of Lignocellulosic Biomass to Hydrocarbon Fuels and Coproducts: 2018 Biochemical Design Case Update; Biochemical Deconstruction and Conversion of Biomass to Fuels and Products via Integrated Biorefinery Pathways; NREL/TP-5100-71949, 2018. doi.org/10.2172/1483234.

[64] C.-S. Tsai, I. I. Kong, A. Lesmana, G. Million, G.-C. Zhang, S. R. Kim, Y.-S. Jin, Rapid and marker-free refactoring of xylose-fermenting yeast strains with Cas9/CRISPR, Biotechnol. Bioeng. 112(11) (2015) 2406-2411. doi.org/10.1002/bit.25632.

[65] G. R. Harvianto, J. Haider, J. Hong, N. Van Duc Long, J.-J. Shim, M. H. Cho, W. K. Kim, M. Lee, Purification of 2,3-butanediol from fermentation broth: process development and techno-economic analysis, Biotechnol. Biofuels 11(1) (2018) 18. doi.org/10.1186/s13068-018-1013-3.

[66] D. Penner, C. Redepenning, A. Mitsos, J. Viell, Conceptual Design of Methyl Ethyl Ketone Production via 2,3-Butanediol for Fuels and Chemicals, Ind. Eng. Chem. Res. 56(14) (2017) 3947-3957. doi.org/10.1021/acs.iecr.6b03678.

[67] D.-J. Zhou, D.-Q. Zhou, X.-H. Cui, F.-M. Wang, M.-Y. Huang, Y.-Y. Jiang, Hydrogenation of aldehydes catalyzed by kieselguhr-supported carboxymethylcellulose-nickel complex, Polym. Adv. Technol. 15(4) (2004) 218-220. doi.org/10.1002/pat.441.

[68] Argonne National Laboratory, GREET 2020 Model, 2020.

[69] G. Wernet, C. Bauer, B. Steubing, J. Reinhard, E. Moreno-Ruiz, B. Weidema, The ecoinvent database version 3 (part 1): overview and methodology, Int. J. Life Cycle Assess. 21(9) (2016) 1218-1230. doi.org/10.1007/s11367-016-1087-8.

[70] U.S. EPA, Lifecycle Analysis of Greenhouse Gas Emissions under the Renewable Fuel Standard. epa.gov/renewable-fuel-standard-program/lifecycle-analysis-greenhouse-gas-emissions-under-renewable-fuel (accessed 2 May 2021).

[71] F. Adom, J. B. Dunn, J. Han, N. Sather, Life-Cycle Fossil Energy Consumption and Greenhouse Gas Emissions of Bioderived Chemicals and Their Conventional Counterparts, Environ. Sci. Technol. 48(24) (2014) 14624-14631. doi.org/10.1021/es503766e.

[72] Argonne National Laboratory, J. B. Dunn, A. Felix, N. Sather, J. Han, S. Snyder, C. He, J. Gong, D. Yue, F. You, Life-cycle Analysis of Bioproducts and Their Conventional Counterparts in GREET™; ANL/ESD-14/9 Rev., 2015. doi.org/10.2172/1250468.

[73] D. Mumberg, R. Müller, M. Funk, Yeast vectors for the controlled expression of heterologous proteins in different genetic backgrounds, Gene 156(1) (1995) 119-122. doi.org/10.1016/0378-1119(95)00037-7.

[74] S.-J. Kim, S.-O. Seo, Y.-S. Jin, J.-H. Seo, Production of 2,3-butanediol by engineered *Saccharomyces cerevisiae*, Bioresour. Technol. 146 (2013) 274-281. doi.org/10.1016/j.biortech.2013.07.081.

[75] T. L. Turner, G.-C. Zhang, E. J. Oh, V. Subramaniam, A. Adiputra, V. Subramaniam, C. D. Skory, J. Y. Jang, B. J. Yu, I. Park, Y.-S. Jin, Lactic acid production from cellobiose and xylose by engineered *Saccharomyces cerevisiae*, Biotechnol. Bioeng. 113(5) (2016) 1075-1083. doi.org/10.1002/bit.25875.

[76] N. Kaliyan, R. V. Morey, D. G. Tiffany, Economic and Environmental Analysis for Corn Stover and Switchgrass Supply Logistics, Bioenergy Res. 8 (2015) 1433-1448.

[77] Idaho National Laboratory, M. S. Roni, D. S. Hartley, M. Griffel, H. Hu, Q. A. Nguyen, H. Cai, D. N. Thompson, Herbaceous Feedstock 2018 State of Technology Report; INL/EXT-18-51654-Rev000, 2020. doi.org/10.2172/1615147.

[78] U.S. Bureau of Labor Statistics, Producer Price Index by Commodity: Chemicals and Allied Products: Sulfuric Acid (WPU0613020T1), Federal Reserve Bank of St. Louis, 2020. alfred.stlouisfed.org/series?seid=WPU0613020T1.

[79] U.S. Geological Survey, Mineral Commodity Summaries 2020: U.S. Geological Survey, 200 p., 2020. doi.org/10.3133/mcs2020.

[80] U.S. Energy Information Administration, Annual Energy Outlook. eia.gov/outlooks/aeo/. (accessed 22 May 2019).

[81] Y. Li, S. S. Bhagwat, Y. R. Cortés-Peña, D. Ki, C. V. Rao, Y.-S. Jin, J. S. Guest, Sustainable Lactic Acid Production from Lignocellulosic Biomass, ACS Sustain. Chem. Eng. 9(3) (2021) 1341-1351. doi.org/10.1021/acssuschemeng.0c08055.

[82] National Renewable Energy Lab (NREL), D. Humbird, R. Davis, L. Tao, C. Kinchin, D. Hsu, A. Aden, Process Design and Economics for Biochemical Conversion of Lignocellulosic Biomass to Ethanol: Dilute-Acid Pretreatment and Enzymatic Hydrolysis of Corn Stover; NREL/TP-5100-47764, 2011. nrel.gov/docs/fy11osti/47764.pdf.

[83] National Renewable Energy Lab (NREL), A. Aden, M. Ruth, K. Ibsen, J. Jechura, K. Neeves, J. Sheehan, B. Wallace, L. Montague, A. Slayton, J. Lukas, Lignocellulosic Biomass to Ethanol Process Design and Economics Utilizing Co-Current Dilute Acid Prehydrolysis and Enzymatic Hydrolysis for Corn Stover; NREL/TP-510-32438, 2002. nrel.gov/docs/fy02osti/32438.pdf.

[84] R. R. Emerson, M. C. Flickinger, G. T. Tsao, Kinetics of dehydration of aqueous 2,3-butanediol to methyl ethyl ketone, Ind. Eng. Chem. Res. 21(3) (1982) 473-477. doi.org/10.1021/i300007a025.

[85] J. Zhao, D. Yu, W. Zhang, Y. Hu, T. Jiang, J. Fu, H. Huang, Catalytic dehydration of 2,3-butanediol over P/HZSM-5: effect of catalyst, reaction temperature and reactant configuration on rearrangement products, RSC Adv. 6(21) (2016) 16988-16995. doi.org/10.1039/C5RA23251A.

---

We claim:

1. A recombinant yeast cell comprising:

(a) a genetic modification to reduce or eliminate expression of glyceraldehyde-3-phosphate dehydrogenase encoded by GPD1 and GPD2;

(b) a genetic modification to reduce or eliminate expression of pyruvate decarboxylase encoded by PDC1;

(c) a genetic modification to reduce or eliminate expression of alcohol dehydrogenase encoded by ADH1;

(d) a heterologous nucleic acid molecule encoding acetolactate synthase (alsS);

(e) a heterologous nucleic acid molecule encoding acetolactate decarboxylase (alsD);

(f) a genetic modification to increase expression of pyruvate decarboxylase encoded by PYC1 and PYC2 as compared to expression of pyruvate decarboxylase in a wild-type yeast cell of the same species as the recombinant yeast cell;

(g) a heterologous nucleic acid molecule encoding malate dehydrogenase (Mdh3); and (h) a heterologous nucleic acid molecule encoding malic enzyme (Me1).

2. The recombinant yeast cell of claim 1, further comprising:

(i) a heterologous nucleic acid molecule encoding xylose reductase (Xyl1);

(j) a heterologous nucleic acid molecule encoding xylitol dehydrogenase (Xyl2);

(k) a heterologous nucleic acid molecule encoding xylulokinase (Xyl3);

(l) a genetic modification to reduce or eliminate expression of 4-nitrophenylphosphatase (Pho13); and (m) a genetic modification to reduce or eliminate expression cytosolic aldehyde dehydrogenase (Ald6).

3. The recombinant yeast cell of claim 1, further comprising a heterologous nucleic acid molecule encoding butanediol dehydrogenase (Bdh1).

4. The recombinant yeast cell of claim 1, wherein the genetic modification to increase expression of pyruvate decarboxylase encoded by PYC1 and PYC2 comprises a strong promoter operably linked to the PYC1 and PYC2.

5. The recombinant yeast cell of claim 4, wherein the strong promoter is a TEF1 promoter or a PGK1 promoter.

6. The recombinant yeast cell of claim 1, wherein the nucleic acid molecule encoding Mdh3 encodes a truncated Mdh3 (tMdh3), wherein the last three amino acids (SKL) are absent.

7. The recombinant yeast cell claim 6, wherein the nucleic acid molecule encoding Mdh3 is operably linked to a strong promoter.

8. The recombinant yeast cell of claim 1, wherein the recombinant yeast cell can ferment xylose.

9. A yeast cell culture comprising two or more of the recombinant yeast cells of claim 1.

10. A method of producing 2,3-butanediol (2,3-BDO) comprising contacting a substrate with the recombinant yeast cell of claim 1.

11. The method of claim 10, wherein the substrate is lignocellulosic or cellulosic feedstock.

12. The method of claim 10, wherein substantially no glycerol or ethanol is accumulated.

13. The method of claim 10, wherein less than 2 g/L of ethanol and less than 2 g/L of glycerol is accumulated.

14. The method of claim 10, wherein 2,3-BDO is produced at more than 0.5 g/L/h or at more than 1.0 g/L/h.

15. The method of claim 10, wherein 2,3-BDO is produced at a yield of 100 g/L or more.

16. A method of producing methyl ethyl ketone (MEK) comprising:

(a) contacting a substrate with the recombinant yeast cell of claim 1 under fermentation conditions;

(b) collecting and purifying 2,3-BDO to form purified 2,3-BDO;

(c) subjecting the purified 2,3-BDO to catalytic dehydration such that MEK is produced.

17. The method of claim 16, wherein, a catalyst for the catalytic dehydration is tricalcium phosphate.

18. The method of claim 16, wherein, the purified 2,3-BDO is greater than 90 wt % pure.

19. A fermentation broth produced by contacting the recombinant yeast cell of claim 1 with a fermentation medium.

20. A method of inducing drought tolerance in plants comprising contacting roots of the plants with the fermentation broth of claim 19.

* * * * *